United States Patent
Kishi et al.

(10) Patent No.: US 11,492,661 B2
(45) Date of Patent: Nov. 8, 2022

(54) MULTIPLEXED SIGNAL AMPLIFICATION

(71) Applicant: President and Fellows of Harvard College, Cambridge, MA (US)

(72) Inventors: Jocelyn Yoshiko Kishi, Boston, MA (US); Brian Beliveau, Brookline, MA (US); Peng Yin, Brookline, MA (US); Yu Wang, Cambridge, MA (US); Sinem K. Saka, Allston, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 535 days.

(21) Appl. No.: 16/464,170

(22) PCT Filed: Jan. 9, 2018

(86) PCT No.: PCT/US2018/013019
§ 371 (c)(1),
(2) Date: May 24, 2019

(87) PCT Pub. No.: WO2018/132392
PCT Pub. Date: Jul. 19, 2018

(65) Prior Publication Data
US 2020/0362398 A1    Nov. 19, 2020

Related U.S. Application Data

(60) Provisional application No. 62/546,836, filed on Aug. 17, 2017, provisional application No. 62/546,418, filed on Aug. 16, 2017, provisional application No. 62/444,734, filed on Jan. 10, 2017.

(51) Int. Cl.
*C12Q 1/6841* (2018.01)

(52) U.S. Cl.
CPC .................................. *C12Q 1/6841* (2013.01)

(58) Field of Classification Search
CPC .................. C12Q 1/6841; C12Q 1/682; C12Q 2531/119; C12Q 2537/101; C12Q 2537/143
See application file for complete search history.

(56) References Cited

U.S. PATENT DOCUMENTS

| | | | |
|---|---|---|---|
| 5,030,566 A | 7/1991 | Son et al. | |
| 5,543,507 A | 8/1996 | Cook et al. | |
| 5,635,352 A * | 6/1997 | Urdea | C12Q 1/6813 435/6.18 |
| 5,866,336 A | 2/1999 | Nazarenko et al. | |
| 6,143,495 A | 11/2000 | Lizardi et al. | |
| 7,033,758 B2 * | 4/2006 | Kenny | C12Q 1/682 435/6.11 |
| 8,623,602 B2 | 1/2014 | Kubista et al. | |
| 8,772,011 B2 | 7/2014 | De Maria et al. | |
| 8,962,241 B2 | 2/2015 | Yin et al. | |
| 9,284,602 B2 | 3/2016 | Zhang et al. | |
| 10,024,796 B2 | 7/2018 | Lin et al. | |
| 10,036,059 B2 | 7/2018 | Zhang et al. | |
| 10,876,971 B2 | 12/2020 | Lin et al. | |
| 11,098,355 B2 | 8/2021 | Heron et al. | |
| 11,286,517 B2 | 3/2022 | Kishi et al. | |
| 2002/0064772 A1 | 5/2002 | Gildea et al. | |
| 2003/0165917 A1 * | 9/2003 | Ullman | C12Q 1/6844 435/6.18 |
| 2003/0207292 A1 | 11/2003 | Notomi et al. | |
| 2005/0009050 A1 | 1/2005 | Nadeau et al. | |
| 2006/0063196 A1 | 3/2006 | Akeson et al. | |
| 2006/0188902 A1 | 8/2006 | Narayanan et al. | |
| 2007/0003950 A1 | 1/2007 | Shen et al. | |
| 2007/0026430 A1 | 2/2007 | Andersen et al. | |
| 2008/0021205 A1 * | 1/2008 | Blau | C07H 19/00 536/23.1 |
| 2011/0129834 A1 | 6/2011 | Chen et al. | |
| 2012/0021410 A1 | 1/2012 | Yin et al. | |
| 2012/0022243 A1 | 1/2012 | Yin | |
| 2013/0072390 A1 | 3/2013 | Wang et al. | |
| 2013/0261019 A1 | 10/2013 | Lin et al. | |
| 2014/0255921 A1 | 9/2014 | Moysey et al. | |
| 2014/0349288 A1 | 11/2014 | Church et al. | |
| 2016/0312272 A1 | 10/2016 | Barish et al. | |
| 2017/0327888 A1 | 11/2017 | Ong et al. | |
| 2017/0349939 A1 * | 12/2017 | Metzker | C12Q 1/686 |
| 2018/0010174 A1 * | 1/2018 | Schaus | G01N 33/5308 |
| 2018/0073068 A1 * | 3/2018 | Peter | C12Q 1/6853 |
| 2018/0148775 A1 * | 5/2018 | Wang | C12Q 1/6848 |
| 2018/0363045 A1 | 12/2018 | Zhang et al. | |
| 2019/0003973 A1 | 1/2019 | Lin et al. | |

(Continued)

FOREIGN PATENT DOCUMENTS

| | | |
|---|---|---|
| CN | 1432061 A | 7/2003 |
| CN | 1836050 A | 9/2006 |

(Continued)

OTHER PUBLICATIONS

Niisson et al., Real-time monitoring of rolling-circle amplification using a modified molecular beacon design. Nucleic Acids Research 30(14) : e66 (Year: 2002).*
Nilsson, M., Lock and roll: single-molecule genotyping in situ using padlock probes and rolling-circle ampliWcation. Histochem Cell Biology 126 :159-164 (Year: 2006).*
Zhao et al., Rolling Circle Amplification: Applications in Nanotechnology and Biodetection with Functional Nucleic Acids. Agnew. Chem. Int, Ed. 47 :6330-6337 (Year: 2008).*
Choi et al., Programmable in situ amplification for multiplexed imaging of mRNA expression. Nature Biotechnology 28(11) : 1208 (Year: 2010).*
Ge et al., A Highly Sensitive Target-Primed Rolling Circle Amplification (TPRCA) Method for Fluorescent in Situ Hybridization Detection of MicroRNA in Tumor Cells. Analytical Chemistry 86: 1808-1815 (Year: 2014).*

(Continued)

*Primary Examiner* — Ethan C Whisenant
(74) *Attorney, Agent, or Firm* — Wolf, Greenfield & Sacks, P.C.

(57) ABSTRACT

Provided herein, in some embodiments, are methods and compositions for highly multiplexed in situ signal amplification via hairpin-mediated concatemerization.

22 Claims, 23 Drawing Sheets

Specification includes a Sequence Listing.

(56) References Cited

U.S. PATENT DOCUMENTS

| | | | |
|---|---|---|---|
| 2019/0106733 A1* | 4/2019 | Kishi | C12P 19/34 |
| 2019/0285644 A1 | 9/2019 | Regev et al. | |
| 2020/0102556 A1* | 4/2020 | da Veiga Beltrame | C40B 20/04 |
| 2020/0109426 A1* | 4/2020 | Xuan | C12Q 1/6853 |
| 2021/0147902 A1* | 5/2021 | Saka | C12Q 1/682 |
| 2021/0277452 A1* | 9/2021 | Kim | C12Q 1/6818 |
| 2021/0388430 A1 | 12/2021 | Zhang et al. | |

FOREIGN PATENT DOCUMENTS

| | | | |
|---|---|---|---|
| CN | 101048505 A | | 10/2007 |
| CN | 101541975 A | | 9/2009 |
| CN | 102317471 A | | 1/2012 |
| CN | 102782158 A | | 11/2012 |
| CN | 103014168 A | | 4/2013 |
| CN | 104164488 A | | 11/2014 |
| JP | 2008-017853 A | | 1/2008 |
| JP | 2013-540451 A | | 11/2013 |
| JP | 2014-504153 A | | 2/2014 |
| JP | 2015-523864 A | | 8/2015 |
| JP | 2002-503948 A | | 5/2020 |
| WO | WO 2007/117256 A1 | | 10/2007 |
| WO | WO 2010/146349 A1 | | 12/2010 |
| WO | WO 2011/156434 A2 | | 12/2011 |
| WO | WO 2012/057689 A1 | | 5/2012 |
| WO | WO 2012/058488 A1 | | 5/2012 |
| WO | WO 2012/071428 A2 | | 5/2012 |
| WO | WO 2012/078312 A2 | | 6/2012 |
| WO | WO 2013/012434 A1 | | 1/2013 |
| WO | WO 2013/188912 A1 | | 12/2013 |
| WO | WO 2014/130388 A1 | | 8/2014 |
| WO | WO 2015/095633 A1 | | 6/2015 |
| WO | WO 2015/114469 A2 | | 8/2015 |
| WO | WO 2015/178978 A2 | | 11/2015 |
| WO | WO 2016/123419 | * | 8/2016 |
| WO | WO 2016/123419 A1 | | 8/2016 |
| WO | WO 2017/143006 A1 | | 8/2017 |
| WO | WO 2017/205719 A1 | | 11/2017 |
| WO | WO 2018/132392 | * | 7/2018 |
| WO | WO 2019/147945 A1 | | 8/2019 |

OTHER PUBLICATIONS

Urbaneck et al., Small RNA Detection by in Situ Hybridization Methods. International J. of Molecular Sciences 16 :13259-13286 (Year: 2015).*

Kishi et al.,Programmable autonomous synthesis of single-stranded DNA. Nature Chemistry (Year: 2018).*

Partial European Search Report dated Sep. 21, 2020 for Application No. EP 18739031.5.

Extended European Search Report for Application EP 18739031.5, dated Feb. 11, 2021.

[No. Author Listed], New COVID-19 Variants. Centers for Disease Control and Prevention. Updated Jan. 15, 2021. 3 pages.

Baccouche et al., Dynamic DNA-toolbox reaction circuits: a walkthrough. Methods. May 15, 2014;67(2):234-49. doi: 10.1016/j.ymeth. 2014.01.015. Epub Feb. 2, 2014.

Douglas et al., Self-assembly of DNA into nanoscale three-dimensional shapes. Nature. May 21, 2009;459(7245):414-8. doi: 10.1038/nature08016.

Fiandaca et al., Self-reporting PNA/DNA primers for PCR analysis. Genome Res. Apr. 2001;11(4):609-13. doi: 10.1101/gr.170401.

Forster et al., A human gut bacterial genome and culture collection for improved metagenomic analyses. Nat Biotechnol. 2019;37(2):186?192. doi:10.1038/s41587-018-0009-7.

Fujimo et al., Quick, Selective and Reversible Photocrosslinking Reaction between 5-Methylcytosine and 3-Cyanovinylcarbazole in DNA Double Strand. Int J Mol Sci. Mar. 12, 2013;14(3):5765-74. doi: 10.3390/ijms14035765.

Jiang et al., Real-time detection of isothermal amplification reactions with thermostable catalytic hairpin assembly. J Am Chem Soc. May 22, 2013;135(20):7430-3 and Supporting Information, doi: 10.1021/ja4023978. Epub May 9, 2013.

Montagne et al., Programming an in vitro DNA oscillator using a molecular networking strategy. Mol Syst Biol. Feb. 1, 2011;7:466. doi: 10.1038/msb.2010.120. Erratum in: Mol Syst Biol. Mar. 8, 2011;7:476. Mol Syst Biol. 2011;7. doi:10.1038/msb.2011.12.

Nazarenko et al., Multiplex quantitative PCR using self-quenched primers labeled with a single fluorophore. Nucleic Acids Res. May 1, 2002;30(9):e37(1-7). doi: 10.1093/nar/30.9.e37.

Rothemund, Folding DNA to create nanoscale shapes and patterns. Nature. Mar. 16, 2006;440(7082):297-302.

Sah et al., Complete Genome Sequence of a 2019 Novel Coronavirus (SARS-CoV-2) Strain Isolated in Nepal. Microbiol Resour Announc. Mar. 12, 2020;9(11):e00169-20. doi: 10.1128/MRA.00169-20.

Simonsson et al., A substrate for telomerase. Trends Biochem Sci. Dec. 2003;28(12):632-8. doi: 10.1016/j.tibs.2003.10.005.

Tisza et al., Discovery of several thousand highly diverse circular DNA viruses. Elife. Feb. 4, 2020;9:e51971. doi: 10.7554/eLife. 51971.

Zeberg et al., The major genetic risk factor for severe COVID-19 is inherited from Neanderthals. Nature. Nov. 2020;587(7835):610-612. doi: 10.1038/s41586-020-2818-3. Epub Sep. 30, 2020.

Zhu et al., Toehold-mediated strand displacement reaction triggered isothermal DNA amplification for highly sensitive and selective fluorescent detection of single-base mutation. Biosens Bioelectron. Sep. 15, 2014;59:276-81. doi: 10.1016/j.bios.2014.03.051. Epub Apr. 1, 2014.

Beliveau et al., Versatile design and synthesis platform for visualizing genomes with Oligopaint FISH probes. Proc Natl Acad Sci USA. Dec. 26, 2012;109(52):21301-6. doi:10.1073/pnas. 1213818110. Epub Dec. 11, 2012.

Beliveau et al., Single-molecule super-resolution imaging of chromosomes and in situ haplotype visualization using Oligopaint FISH probes. Nat Commun. May 2015;6:7147(1-13).

Chen et al., Conditionally fluorescent molecular probes for detecting single base changes in double-stranded DNA. Nat Chem. Sep. 2013;5(9):782-9. Author Manuscript, 16 pages.

Chhabra et al., DNA self-assembly for nanomedicine. Adv Drug Deliv Rev. Apr. 30, 2010;62(6):617-25. doi:10.1016/j.addr.2010.03. 005. Epub Mar. 15, 2010.

Collins et al., A branched DNA signal amplification assay for quantification of nucleic acid targets below 100 molecules/ml. Nucl Acids Res. Aug. 1997;25(15):2979-2984.

Green et al., Toehold switches: de-novo-designed regulators of gene expression. Cell. Nov. 6, 2014;159(4):925-39. doi: 10.1016/j.cell. 2014.10.002. Epub Oct. 23, 2014.

Hollenstein. DNA Synthesis by primer exchange reaction cascades. Chembiochem. Mar. 2, 2018;19(5):422-4. Epub Jan. 24, 2018.

Jungmann et al., Nanoscale imaging in DNA nanotechnology. Wiley Interdiscip Rev Nanomed Nanobiotechnol. Jan.-Feb. 2012;4(1):66-81. doi:10.1002/wnan.173. Epub Nov. 23, 2011.

Jungmann et al., Single-molecule kinetics and super-resolution microscopy by fluorescence imaging of transient binding on DNA origami. Nano Lett. Nov. 10, 2010;10(11):4756-61.

Jungmann et al., Multiplexed 3D cellular super-resolution imaging with DNA-PAINT and Exchange-PAINT. Nat Methods. Mar. 2014;11(3):313-8. doi: 10.1038/nmeth.2835. Epub Feb. 2, 2014.

Kishi et al., Programmable autonomous synthesis of single-stranded DNA. Nat Chem. Feb. 2018;10(2):155-64. Epub Nov. 6, 2017. Author Manuscript, 22 pages.

Li et al., Multiplexed detection of pathogen DNA with DNA-based fluorescence nanobarcodes. Nat Biotechnol. Jul. 2005;23(7):885-9. Epub Jun. 12, 2005.

Lin et al., Functional DNA nanotube arrays: bottom-up meets top-down. Angewandte Chemie. 2007;119(32):6201-4.

Lin et al., Self-assembled combinatorial encoding nanoarrays for multiplexed biosensing. Nano Lett. Feb. 2007;7(2):507-12.

Player et al., Single-copy gene detection using branched DNA (bDNA) in situ hybridization. J Histochem & Cytochem. May 2001;49(5):603-11.

(56) References Cited

OTHER PUBLICATIONS

Wang et al., RNAscope: A novel in situ RNA analysis platform for formalin-fixed, paraffin-embedded tissues. J Mol Diagn. Jan. 2012;14(1):22-9.

Wang et al., Proximity hybridization-regulated immunoassay for cell surface protein and protein-overexpressing cancer cells via electrochemiluminescence. Anal Chem. Mar. 6, 2018;90(5):3013-8. Epub Feb. 23, 2018.

Weibrecht et al., Proximity ligation assays: a recetn addition to the proteomics toolbox. Expert Rev of Proteomics. Jun. 2010;7(3):401-9.

Weibrecht et al., In situ deletion of individual mRNA molecules and protein complexes or post-translational modifications using padlock probes combined with the in situ proximity ligation assay. Nat Protoc. Feb. 2013;8(2):355-72.

Wharam et al., Specific detection of DNA and RNA targets using a novel isothermal nucleic acid amplification assay based on the formation of a three-way junction structure. Nucleic Acids Res. Jun. 1, 2001;29(11):E54-4.

Woehrstein et al., Sub-100 nm metafluorophores with digitally tunable optical properties self-assembled from DNA. Sci Adv. Jun. 21, 2017;3(6):e1602128.

Wu et al., A nonenzymatic hairpin DNA Cascade reaction provides high signal gain of mRNA imagin inside live cells. J Am Chem Soc. Apr. 2015;137(15):4900-3.

Yin et al., Programming biomolecular self-assembly pathways. Nature. Jan. 17, 2008;451(7176):318-22. doi:10.1038/nature06451.

Yin et al., Programming DNA tube circumferences. Science. Aug. 8, 2008;321(5890):824-6. doi:10.1126/science.1157312.

Zhang et al., Control of DNA strand displacement kinetics using toehold exchange. J Am Chem Soc. Dec. 2, 2009;131(47):17303-14. doi: 10.1021/ja906987s.

Zhang et al., Optimizing the specificity of nucleic acid hybridization. Nat Chem. Epub Jan. 22, 2012, 7 pages.

Zhang et al., Dynamic DNA nanotechnology using strand-displacement reactions. Nat Chem. 2011;3(2):103-13.

U.S. Appl. No. 16/017,570, filed Jun. 25, 2018, Published, U.S. 2018-0363045.

U.S. Appl. No. 16/008,719, filed Jun. 14, 2018, Published, U.S. 2019-0003973.

U.S. Appl. No. 15/542,953, filed Dec. 4, 2017, Published, U.S. 2018-0010174.

U.S. Appl. No. 15/622,261, filed Jun. 14, 2017, Published, U.S. 2017-0327888.

U.S. Appl. No. 15/999,245, filed Aug. 17, 2018, Published, U.S. 2019-0106733.

PCT/US2019/015161, filed Jan. 25, 2019, Published, WO 2019/147945.

PCT/US2018/013019, dated May 25, 2018, Invitation to Pay Additional Fees.

PCT/US2018/013019, dated Jul. 11, 2018, International Search Report and Written Opinion.

PCT/US2018/013019, dated Jul. 25, 2019, International Preliminary Report on Patentability.

U.S. Appl. No. 17/169,145, filed Feb. 5, 2021, Pending.

U.S. Appl. No. 16/964,527, filed Jul. 23, 2020, Published, 2021-0147902.

EP 18739031.5, dated Sep. 21, 2020, Partial European Search Report.

EP 18739031.5, dated Feb. 11, 2021, Extended European Search Report.

U.S. Appl. No. 13/882,231, filed Jul. 1, 2013, Granted, U.S. Pat. No. 9,284,602.

U.S. Appl. No. 14/553,165, filed Nov. 25, 2014, Granted, U.S. Pat. No. 10,036,059.

U.S. Appl. No. 17/169,145, filed Feb. 5, 2021, Published, 2021-0388430.

U.S. Appl. No. 13/882,223, Jun. 11, 2013, Granted, U.S. Pat. No. 10,024,796.

U.S. Appl. No. 16/008,719, filed Jun. 14, 2018, Granted, U.S. Pat. No. 10,876,971.

U.S. Appl. No. 15/999,245, filed Aug. 17, 2018, Allowed, U.S. Pat. No. 11,286,517.

U.S. Appl. No. 17/592,435, filed Feb. 3, 2022, Pending, N/A.

\* cited by examiner

Bleach fluorescence

Digest fluorescent oligos

Wash fluorescent oligos

Transient binding of fluorescent oligos

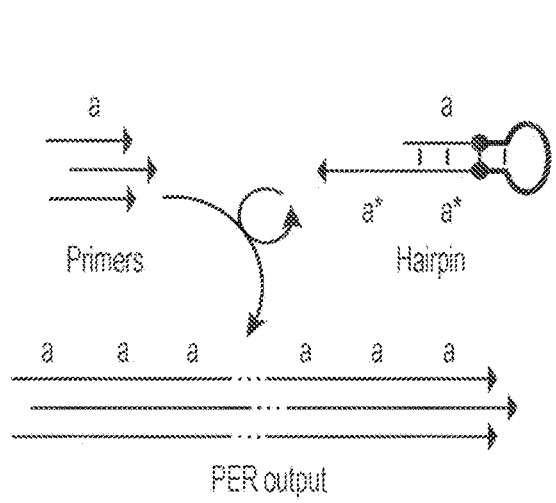
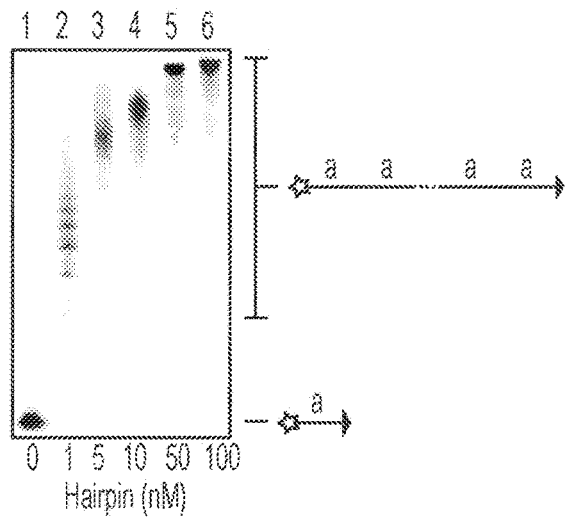
FIG. 9A  FIG. 9B
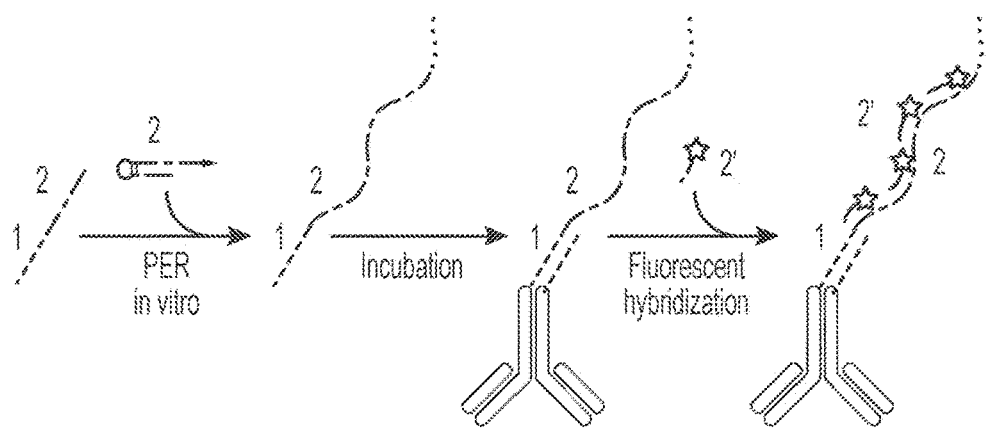
FIG. 10A
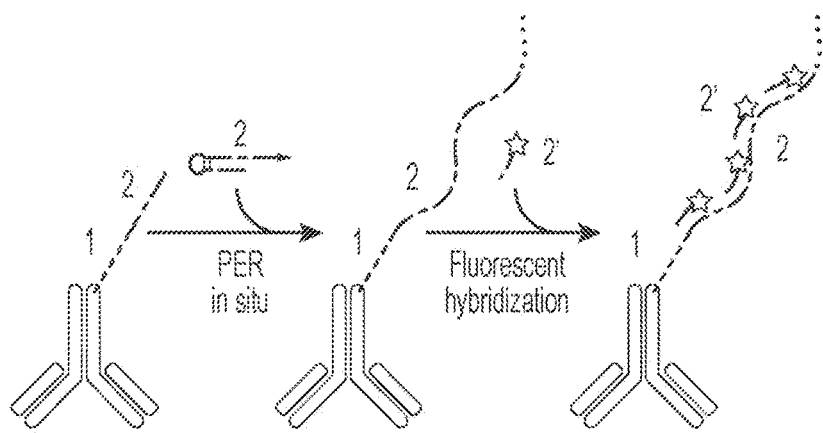
FIG. 10B

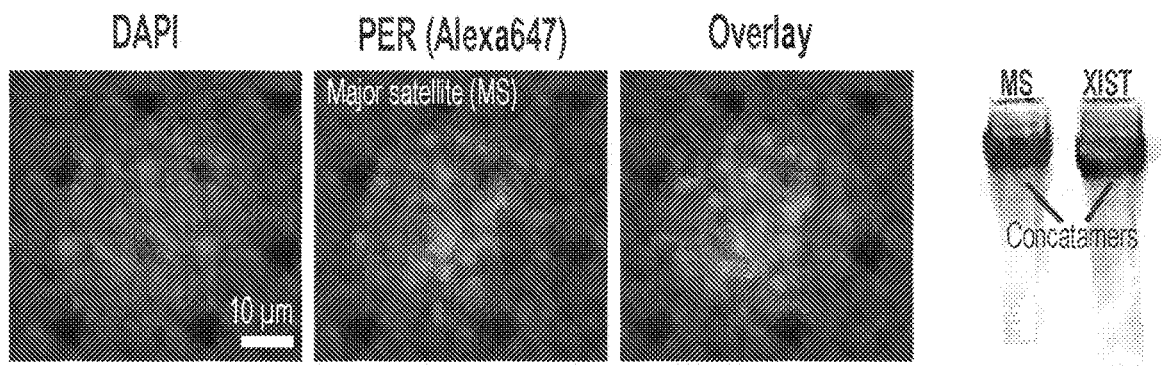
FIG. 11A
FIG. 11B
FIG. 11C
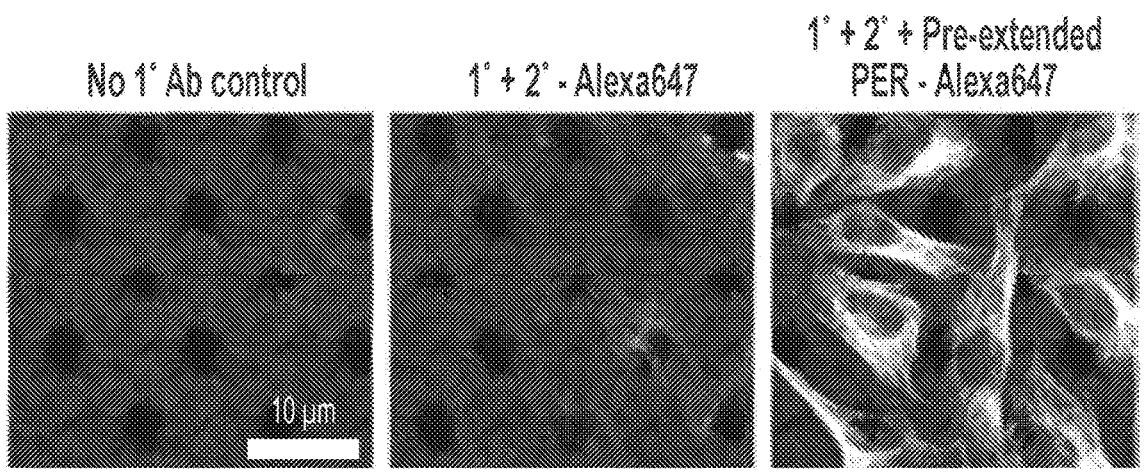
FIG. 12

MULTIPLEXED SIGNAL AMPLIFICATION

RELATED APPLICATIONS

This application is a national stage filing under 35 U.S.C. § 371 of international patent application number PCT/US2018/013019, filed Jan. 9, 2018, which claims the benefit under 35 U.S.C. § 119(e) of U.S. provisional application No. 62/444,734, filed Jan. 10, 2017, U.S. provisional application No. 62/546,418, filed Aug. 16, 2017, and U.S. provisional application No. 62/546,836, filed Aug. 17, 2017, each of which is incorporated by reference herein in its entirety.

FEDERALLY SPONSORED RESEARCH

This invention was made with government support under N00014-13-1-0593, N00014-16-1-2182, and N00014-16-1-2410 awarded by U.S. Department of Defense under MH106011 and EB018659 awarded by National Institutes of Health, and under 1317291 awarded by National Science Foundation. The government has certain rights in the invention.

BACKGROUND

Knowledge of the subcellular localization patterns of biomolecules can provide key insights into how these molecules function. Accordingly, techniques that interrogate in situ localization of biomolecules such as fluorescence in situ hybridization (FISH) and immunofluorescence (IF) play critical roles in a broad range of disciplines from basic research to clinical diagnostics. Despite the widespread use of these methods, they have limited multiplexing capability due to spectral overlap of fluorophores. Further, when the targets are of low abundance or are being examined in the context of a crowded tissue environment, it is often difficult with these techniques to achieve in situ a signal to noise ratio that is acceptable for producing clear, interpretable signals.

SUMMARY

Provided herein, in some embodiments, are robust, highly efficient imaging methods compatible with high levels of multiplexing for in situ molecular (e.g., nucleic acid and/or protein) detection, for example, in tissue samples and in bodily fluid samples. An important criterion for in situ detection is an achievable level of signal for targets of variable expression level. Especially for thick tissue samples, detection of rare targets continues to be challenging due to high auto-fluorescence background and increased scattering of the signal. This problem is worsened for multiplexed immunofluorescence detection of several targets, which requires abandoning secondary antibodies and, thus, the limited amplification that they provide through multivalent binding. This creates a clear need for signal amplification, particularly to image low abundance targets.

The multiplexing platform of the present disclosure provides a means for in situ signal amplification of multiple low abundance targets, while avoiding the obstacles, such as high auto-fluorescence background and increased scattering of signal, that accompany imaging molecules within thick tissue samples. The methods and compositions of the present disclosure enable multiplexed analyses in a variety of different context, including, but not limited to neuronal immunity factors (e.g., cytokines) and their interactions with neuronal cells in healthy and Alzheimer's disease human brain sections, for example. Such analyses performed directly in situ and at protein level are valuable to understanding the neurotoxic and neuroprotective effects of microglia on different neuronal cell types and their relevance to neurodegenerative diseases at a systems level, for example. Other multiplexed analyses in different tissue types also provide substantial benefit in understanding a variety of other disease states because many serious diseases involve multiple factors that should be studied at the same time.

The multiplexed signal amplification methods as provided herein generate long ssDNA concatemers from short ssDNA primer sequences. These concatemers are then used as scaffold strands onto which fluorescent strands are applied to generate a localized, amplified, detectable signal.

These methods offer unique advantages for in situ labeling, for example: they typically use simple and inexpensive reagents, and are compatible with in situ amplification in cells and tissues, providing high signal-to-noise (SNR); the end products are spatially compact, which enables better spatial isolation of multiple targets with better imaging quality and resolution (relative to existing methods); and the methods stipulate great flexibility for sequence design, making it feasible to design and implement simultaneous multiplexing.

Thus, some aspects of the present disclosure provide multiplexed target detection methods, comprising: (a) combining a sample containing a plurality of molecular (e.g., nucleic acid targets) with a plurality of probe strands (e.g., at a concentration of 1 nM to 1 µM), wherein each probe strand comprises (i) an unpaired 5' target domain complementary to a region of the molecular target (e.g., complementary to one of the nucleic acid targets) and (ii) an unpaired 3' primer domain, and producing a first reaction mixture comprising molecular targets bound to probe strands; (b) combining the first reaction mixture produced in step (a) with dNTPs (e.g., at a concentration of 1-500 µM), strand-displacing polymerase, and a plurality of catalytic molecules (e.g., at a concentration of 1 nM to 1 µM), wherein each catalytic molecule comprises, 5' to 3', a first domain, a second domain, and a third domain wherein the first domain is bound to the second domain, and the third domain is an unpaired 3' toehold domain complementary to the unpaired 3' primer domain of one of the probe strands, and producing a second reaction mixture comprising nucleic acid concatemers bound to molecular targets; (c) combining the second reaction mixture produced in step (b) with a plurality of signal strands (e.g., at a concentration of 1 nM to 1 µM), wherein each signal strand is linked to a different detectable molecule and comprises a domain complementary to the unpaired 3' primer domain of one of the probe strands, and producing concatemers labeled by a plurality of signal strands; and (d) optionally further comprising imaging the labeled concatemers.

Other aspects of the present disclosure provide multiplexed target detection methods, comprising: (a) combining a plurality of probe strands with dNTPs, strand-displacing polymerase, and a plurality of catalytic molecules, wherein each probe strand comprises (i) an unpaired 5' target domain complementary to a molecular (e.g., nucleic acid) target and (ii) an unpaired 3' primer domain, and wherein each catalytic molecule comprises, 5' to 3', a first domain, a second domain, and a third domain wherein the first domain is bound to the second domain, and the third domain is an unpaired 3' toehold domain complementary to the unpaired 3' primer domain of one of the probe strands, and producing a first reaction mixture comprising nucleic acid concatemers bound to probe strands; (b) combining the first reaction mixture produced in step (a) with a sample containing a plurality of molecular targets (e.g., nucleic acid targets) and producing a second reaction mixture comprising nucleic acid concatemers bound to molecular targets; (c) combining the second reaction mixture produced in step (b) with a plurality of signal strands, wherein each signal strand is linked to a different detectable molecule and comprises a domain complementary to the unpaired 3' primer domain of one of the probe strands, and producing concatemers labeled by a plurality of signal strands; and (d) optionally further comprising imaging the labeled concatemers.

In some embodiments, the catalytic molecules are comprised of DNA. In some embodiments, the catalytic molecules are comprised of RNA.

In some embodiments, the first domain of each catalytic molecule is bound to the second domain of the same catalytic molecule. In some embodiments, the first domain of each catalytic molecule comprises a sequence wholly complementary to the second domain of the same catalytic molecule. In some embodiments, the second domain of each catalytic molecule comprises a sequence identical to the third domain of the same catalytic molecule.

In some embodiments, each catalytic molecule further comprises a stopper molecule or modification that terminates polymerization located between the first and second domains of the same catalytic molecule. For example, the molecule or modification that terminates polymerization may be selected from a triethylene glycol (TEG), 18-atom hexa-ethylene glycol, adenylation, azide, digoxigenin, cholesteryl-TEG, 3-cyanovinylcarbazole (CNVK), iso-dG and iso-dC. In some embodiments, the stopper molecule is guanine and the catalytic molecule is comprised of adenine, thymine and cytosine, or in other embodiments, the stopper molecule is cytosine and the catalytic molecule is comprised of adenine, thymine and guanine.

In some embodiments, each catalytic molecule is a catalytic hairpin molecule further comprising a loop domain located between the first and second domains. In some embodiments, each catalytic hairpin molecule is comprised of a single strand of DNA having a length of 25-300 nucleotides. In some embodiments, the catalytic molecule comprises two strands of DNA bound together, whereby the first strand contains the first domain, and the second strand comprises the second and third domains.

In some embodiments, the probe strands are comprised of DNA. In some embodiments, the probe strands are comprised of RNA. In some embodiments, each probe strand has a length of 10-50 nucleotides. In some embodiments, the target domain of each probe strand has a length of 5-25 nucleotides. In some embodiments, the primer domain of each probe strand has a length of 5-25 nucleotides.

In some embodiments, the nucleic acid target comprises DNA or RNA. For example, the nucleic acid target may be chromosomal DNA, or the nucleic acid target may be mRNA or miRNA.

In some embodiments, the detectable molecule of the signal strands is a fluorophore. In some embodiments, each of the signal strands has a length of 10-30 nucleotides.

In some embodiments, the strand-displacing polymerase is selected from phi29 DNA polymerases, Bst DNA polymerases, and Bsu DNA polymerase, large fragment.

In some embodiments, a reaction mixture comprises aqueous buffer, optionally phosphate buffered saline (PBS). In some embodiments, a reaction mixture comprises $MgSO_4$, optionally at a concentration of 5-50 mM.

In some embodiments, the plurality of step (a) comprises 2-100 of the probe strands; the plurality of step (b) comprises 2-100 of the catalytic molecules; and/or the plurality of step (c) comprises 2-100 of the signal strands. In some embodiments, the plurality of step (a) comprises 2-1000 of the probe strands; the plurality of step (b) comprises 2-1000 of the catalytic molecules; and/or the plurality of step (c) comprises 2-1000 of the signal strands. In some embodiments, the plurality of step (a) comprises 2-10,000 of the probe strands; the plurality of step (b) comprises 2-10,000 of the catalytic molecules; and/or the plurality of step (c) comprises 2-10,000 of the signal strands. In some embodiments, the plurality of step (a) comprises 2-100,000 of the probe strands; the plurality of step (b) comprises 2-100,000 of the catalytic molecules; and/or the plurality of step (c) comprises 2-100,000 of the signal strands.

In some embodiments, the sample is a cell sample. In some embodiments, the sample is a tissue culture cell. In some embodiments, the sample is a tissue sample. The tissue sample may be, for example, a brain tissue sample. In some embodiments, the tissue sample is a tumor sample, In some embodiments, the sample is a bodily fluid sample. In some embodiments, the bodily fluid sample is a serum sample, a blood sample, or a saliva sample. Other bodily fluid samples may be used. In some embodiments, the sample is a fecal sample.

Some aspects of the present disclosure provide multiplexed target detection methods, comprising: (a) combining a sample containing a plurality of protein or peptide targets with a plurality of primary binding partners (e.g., antibodies), each of which binds specifically to a protein or peptide target and is linked to a probe strand, and producing a reaction mixture comprising protein or peptide bound to primary binding partners (e.g., antibodies); (b) combining the reaction mixture produced in step (a) with dNTPs, strand-displacing polymerase, and a plurality of catalytic molecules, each catalytic molecule comprising, 5' to 3', a first domain, a second domain, and a third domain wherein the first domain is bound to the second domain, and the third domain is an unpaired 3' toehold domain complementary to the probe strand of one of the antibodies, and producing a reaction mixture comprising nucleic acid concatemers bound to antibodies; (c) combining the reaction mixture produced in step (b) with a plurality of signal strands, each signal strand linked to a different detectable molecule and comprising a domain complementary to the probe strand of one of the antibodies, and producing concatemers labeled by a plurality of signal strands; and (d) optionally further comprising imaging the labeled concatemers. In some embodiments, the primary binding partner is an antibody. In some embodiments, the antibody is a full-length antibody. In some embodiments, the antibody is an antigen-binding antibody fragment.

Other aspects of the present disclosure provide multiplexed target detection methods, comprising: (a) combining a sample containing a plurality of protein or peptide targets with a plurality of primary binding partners (e.g., antibodies), each of which binds specifically to a protein or peptide target and is linked to a bridge strand, and producing a reaction mixture comprising protein or peptide bound to primary binding partners (e.g., antibodies); (b) combining the reaction mixture produced in step (a) with a plurality of probe strands, each probe strand comprising (i) an unpaired 5' target domain complementary to the of bridge strand of one of the primary binding partners (e.g., antibodies) and (ii) an unpaired 3' primer domain, and producing a reaction mixture comprising probe strands bound to primary binding partners (e.g., antibodies); (c) combining the reaction mixture produced in step (b) with dNTPs, strand-displacing polymerase, and a plurality of catalytic molecules, each catalytic molecule comprising, 5' to 3', a first domain, a second domain, and a third domain wherein the first domain is bound to the second domain, and the third domain is an unpaired 3' toehold domain complementary to the unpaired 3' primer domain of one of the probe strands, and producing a reaction mixture comprising nucleic acid concatemers bound to primary binding partners (e.g., antibodies); (d) combining the reaction mixture produced in step (c) with a plurality of signal strands, each signal strand linked to a different detectable molecule and comprising a domain complementary to the unpaired 3' primer domain of one of the probe strands, and producing concatemers labeled by a plurality of signal strands; and (e) optionally further comprising imaging the labeled concatemers.

Still other aspects of the present disclosure provide multiplexed target detection methods, comprising: (a) combining a sample containing a plurality of protein or peptide targets with a plurality of primary antibodies (or a plurality of other binding partners), each of which binds specifically to a protein or peptide target, and producing a reaction mixture comprising protein or peptide bound to primary antibodies; (b) combining the reaction mixture produced in step (a) with a plurality of secondary antibodies (or with a plurality of other secondary probes that bind to binding partners, such as protein A, protein G or antibody-specific nanobodies), each of which binds specifically to a primary antibody and is linked to a probe strand, and producing a reaction mixture comprising primary antibodies bound to secondary antibodies; (c) combining the reaction mixture produced in step (b) with dNTPs, strand-displacing polymerase, and a plurality of catalytic molecules, each catalytic molecule comprising, 5' to 3', a first domain, a second domain, and a third domain wherein the first domain is bound to the second domain, and the third domain is an unpaired 3' toehold domain complementary to the probe strand of one of the secondary antibodies, and producing a reaction mixture comprising nucleic acid concatemers bound to secondary antibodies; (c) combining the reaction mixture produced in step (c) with a plurality of signal strands, each signal strand linked to a different detectable molecule and comprising a domain complementary to the probe strand of one of the secondary antibodies, and producing concatemers labeled by a plurality of signal strands; and (d) optionally further comprising imaging the labeled concatemers.

Yet other aspects of the present disclosure provide multiplexed target detection methods, comprising: (a) combining a sample containing a plurality of protein or peptide targets with a plurality of primary binding partners (e.g., antibodies), each of which binds specifically to a protein or peptide target, and producing a reaction mixture comprising protein or peptide bound to primary binding partners (e.g., primary antibodies); (b) combining the reaction mixture produced in step (a) with a plurality of secondary binding partners (e.g., secondary antibodies), each of which binds specifically to a primary binding partners and is linked to a bridge strand, and producing a reaction mixture comprising primary binding partners bound to secondary binding partners (e.g., secondary antibodies or other secondary probes that bind to binding partners, such as protein A, protein G or antibody-specific nanobodies); (c) combining the reaction mixture produced in step (b) with a plurality of probe strands, each probe strand comprising (i) an unpaired 5' target domain complementary to the of bridge strand of one of the secondary binding partners and (ii) an unpaired 3' primer domain, and producing a reaction mixture compris-ing probe strands bound to secondary antibodies; (d) combining the reaction mixture produced in step (c) with dNTPs, strand-displacing polymerase, and a plurality of catalytic molecules, each catalytic molecule comprising, 5' to 3', a first domain, a second domain, and a third domain wherein the first domain is bound to the second domain, and the third domain is an unpaired 3' toehold domain complementary to the unpaired 3' primer domain of one of the probe strands, and producing a reaction mixture comprising nucleic acid concatemers bound to secondary binding partners; (e) combining the reaction mixture produced in step (d) with a plurality of signal strands, each signal strand linked to a different detectable molecule and comprising a domain complementary to the unpaired 3' primer domain of one of the probe strands, and producing concatemers labeled by a plurality of signal strands; and (f) optionally further comprising imaging the labeled concatemers.

Also provided herein, in some aspects are compositions comprising: (a) a catalytic molecule comprising, 5' to 3', a first domain, a second domain, and a third domain, wherein the first domain binds to the second domain, and the third domain is an unpaired 3' toehold domain; (b) a probe strand comprising (i) an unpaired 5' target domain that binds specifically to a molecular target and (ii) an unpaired 3' primer domain that binds to the unpaired 3' toehold domain of the catalytic molecule; and (c) a signal strand linked to a detectable molecule and comprising a domain that binds to the unpaired 3' primer domain of the probe strands.

In some embodiments, a composition comprises: (a) a plurality of catalytic molecules, each catalytic molecule comprising, 5' to 3', a first domain, a second domain, and a third domain, wherein the first domain binds to the second domain, and the third domain is an unpaired 3' toehold domain; (b) a plurality of probe strands, each probe strand comprising (i) an unpaired 5' target domain that binds specifically to a molecular target and (ii) an unpaired 3' primer domain that binds to the unpaired 3' toehold domain of one of the catalytic molecules; and (c) a plurality of signal strands, each signal strand linked to a different detectable molecule and comprising a domain that binds to the unpaired 3' primer domain of one of the probe strands.

Further provided herein, in some embodiments, are samples comprising a nucleic acid target to which a concatemer of tandem repeat sequence is bound, wherein a signal strand linked to a detectable label is bound to each sequence of the concatemer.

In some embodiments, a sample comprises a protein target to which an antibody (or other binding partner) is bound, wherein the antibody is linked to a concatemer of tandem repeat sequence, and a signal strand linked to a detectable label is bound to each sequence of the concatemer.

In some embodiments, a sample comprises a protein target to which a primary binding partner (e.g., primary antibody) is bound, wherein a secondary binding partner (e.g., secondary antibody) is bound to the primary binding partner, the secondary binding partner is linked to a concatemer of tandem repeat sequence, and a signal strand linked to a detectable label is bound to each sequence of the concatemer.

BRIEF DESCRIPTION OF THE DRAWINGS

(FIG. 2A) 5 hairpins mediate the stepwise elongation of a Cy5-labeled primer with domain 1. (FIG. 2B) Different subsets of hairpins included during a 4 hour incubation at 37° C. Primer sequence: /5Cy5/TTCTCTTATT (SEQ ID NO:1); Hairpin sequences: ACTAAAT-TCAGGGCCTTTTGGCCCTGAATT-TAGTAATAAGAGA/3InvdT/ (SEQ ID NO:2); ATATCC-CATAGGGCCTTTTGGCCCTATGGGATATTGAATTTAG/3InvdT/ (SEQ ID NO:3); ATTACACTACGGGCCTTTTGGCCCGTAGTGTAAT-TATGGGATA/3InvdT/ (SEQ ID NO:4); ATAT-TAAACCGGGCCTTTTGGCCCGGTT-TAATATGTAGTGTAA/3InvdT/ (SEQ ID NO:5); ATCATTTTTCGGGCCTTTTGGCCCGAAAAAT-GATGGTTTAATA/3InvdT/ (SEQ ID NO:6).

(FIG. 3A) A single hairpin (ATCTCTTATTGGGCCTTTTGGCC-CAATAAGAGATAATAAGAGA/3InvdT/ (SEQ ID NO:7) can mediate the repetitive extension of a primer (SEQ ID NO:1) with domain 1. (FIG. 3B) Primers are extended into long repetitive sequences. (FIG. 3C) Increasing the concentration of the catalytic hairpin during a 4 hour incubation at 37° C. increases the rate of telomerization.

(FIG. 5A) A target X, such as an mRNA or region of the chromosome, is identified. (FIG. 5B) The system contains three components, a probe (X' 1) that is designed to bind to the target of interest, a PER hairpin, and a fluorescent complement (1'). (FIG. 5C) First, the probe is hybridized to its target in situ following standard DNA or RNA FISH protocols. (FIG. 5D) After hybridization, the handles are extended into long telomeres (strands) by a PER hairpin. (FIG. 5E) Finally, fluorescent complement strands are hybridized to the long synthesized strands to localize fluorescent signal amplification.

(FIG. 6A) A probe (1) (/5ATTO488N/TTGCGAGGAAAACTGAAAAAGGTTTCTCTTATT; SEQ ID NO:41) was designed to bind the major satellite portion of chromosomes and labeled with the ATTO 488 fluorophore on its 5' end. A PER hairpin (2) (SEQ ID NO:41) and fluorescent probes (3) (/5ATTO565N/TTAATAAGAGATAATAAGAGAT/3InvdT/; SEQ ID NO:8) labeled with the ATTO 565 dye and complementary to extended telomere sequences were used for signal amplification and detection. (FIG. 6B) After hybridization of the probes (1), they were extended with the PER hairpins (2). After telomerization, fluorescent probes (3) were hybridized and imaged. (FIG. 6C) In the presence of the full PER system, signals from both ATTO dyes co-localize in the nucleus. Without the hairpin (2), no signal from the fluorescent probes (3) is detected, as expected. Scale bar is 10 μm.

(FIG. 7A) A target signal may be bleached by targeting the sample with a strong laser. (FIG. 7B) Signal may be removed by digesting the fluorescent oligos (nucleic acid strands), for example with a nuclease, such as a RNase enzyme if only the fluorescent strands contain RNA backbones. Examples of enzymes include USER® enzyme (Uracil-Specific Excision Reagent; NEB), DNaseI and ExoI. (FIG. 7C) Fluorescent strands may be washed from a target under low salt conditions. (FIG. 7D) Short fluorescent strands that only bind transiently can be used to localize the fluorescent signal before a wash step.

FIGS. 9A-9B: Primer Exchange Reaction. (FIG. 9A) Schematic of a PER reaction that copies that repeatedly copies the same short sequence "a", generating a long concatemer of ssDNA. (FIG. 9B) A PAGE denaturing gel showing extension under different hairpin concentrations. 100 nM primers were incubated with Bst Polymerase and the given hairpin concentrations for 4 hours at 37° C. with dATP, dTTP, and dCTP at 100 μM.

FIGS. 10A-10B: PER-based amplification of IF signal. (FIG. 10A) In vitro extension of the concatemer: the pre-extended concatemer can be hybridized to a bridge sequence on the Ab. (FIG. 10B) In situ extension: the PER primer is presented on the Ab directly, and extended in situ by PER.

FIGS. 11A-11C: FISH with PER-based signal amplification using pre-extended strands. (FIG. 11A) Oligo probes with pre-extended PER sequences used in a FISH experiment targeting the mouse major satellite (MS) in embryonic fibroblasts. (FIG. 11B) A set of 48 oligo probes with pre-extended PER sequences used in a FISH experiment targeting the non-repeat single-copy X-inactivation center (Xist) region on X-chromosome. Maximum projection of the z-stacks taken with an epifluorescence microscope are shown. (FIG. 11C) Visualization of the pre-extended strands on 15% PAGE denaturing gel prior to FISH experiment. Thick bands correspond to approximately 2 kb. Probe for top panels (major satellite): CCACTGTAGGACGTG-GAATATGGCAAGAAAACTGAAAATCATGGTTCAT-CATCAT (SEQ ID NO:9); hairpin for top and bottom panels: ACATCATCATGGGCCTTTTGGCCCATGAT-GATGTATGATGATG/3InvdT/ (SEQ ID NO:10).

FIG. 12: Signal amplification in IF using PER. Mouse embryonic fibroblasts were stained with anti-beta-tubulin primaries. Secondary antibody staining was either performed with Alexa647-conjugated secondary antibodies (middle) or DNA-conjugated secondary antibodies which present a docking site for binding of pre-extended PER strands where Alexa647-conjugated complementary signal strands can bind (right). Negative control (left) was prepared by omitting the primary antibody but otherwise treating the sample same as the PER condition. No significant unspecific background was detected. Hairpin: ACCAATAATAGGGCCTTTTGGCCCTATTATTGGTT-ATTATTGG/3InvdT/ (SEQ ID NO:11); Primer (bridge complement/B38*+p25 for priming): CTAGATCGAACT-ATTCGAACACTAAATATTCCAATAATA (SEQ ID NO:12); B38 bridge sequence conjugated to the secondary antibody: /5ThioMC6-D/TATTTAGTGTTCGAATAGTTC-GATCTAG (SEQ ID NO:13); Fluorescent (25*): /5Alex647N/TTTATTATTGGTTATTATTGGT/3InvdT/ (SEQ ID NO:14).

(FIG. 14A) The original approach uses strands that are extended in situ, that is the probe strands are first bound to their target (DNA/RNA/proteins) within a fixed sample and then extended in place. (FIG. 14B) The in vitro approach instead pre-extends the concatemers in vitro and then hybridizes them to the target.

(FIG. 15A) Schematic for two color experiment, which used primers 19 and 22 attached to probes targeting the minor satellite and major satellite regions, respectively. The p22' p22' p22' strand targeting the major satellite contained an ATTO 565 dye, and the p19' p19' p19' strand contained an Alexa 647 dye. (FIG. 15B) Imaging results for individual channels, showing expected morphology of the two targets in the proper fluorescence channels. Cells were also DAPI stained as a control. Minor satellite with primer 19 probe: AGATGAGTGAGTTACACTGAAAAACACATTCGTTGGAAACGGTTTCTCTTATT (SEQ ID NO:15); Major satellite with primer 22 probe: CCACTGTAGGACGTGGAATATGGCAAGAAAACTGAAAATCATGGTTTTACACTAC (SEQ ID NO:16); Hairpin 19: ATCTCTTATTGGGCCTTTTGGCCCAATAAGAGATAATAAGAGA/3InvdT/ (SEQ ID NO:17); Hairpin 22: ATTACACTACGGGCCTTTTGGCCCGTAGTGTAATGTAGTGTAA/3InvdT/ (SEQ ID NO:18); Fluorescent p19': /5Alex647N/TTAATAAGAGATAATAAGAGATAATAAGAGAT/3InvdT/ (SEQ ID NO:19); Fluorescent p22': /5ATTO565N/TTGTAGTGTAATGTAGTGTAATGTAGTAAT/3InvdT/ (SEQ ID NO:20).

DETAILED DESCRIPTION

Knowledge of the subcellular localization patterns of biomolecules can provide key insights into how these molecules function. Accordingly, techniques that interrogate the in situ localization of biomolecules such as fluorescence in situ hybridization (FISH) and immunofluorescence (IF) play critical roles in a broad range of disciplines from basic research to clinical diagnostics. Despite the widespread use of these methods, however, technical limitations can still limit their utility. Specifically, these techniques often struggle to produce clear, interpretable signals, especially when the targets are of low abundance or are being examined in the context of a crowded tissue environment. Provided herein is a method for amplifying in situ imaging signals to, inter alia, address this limitation.

The underlying amplification process of the present disclosure is referred to as the Primer Exchange Reaction (PER). PER has several advantages for in situ labeling, including, for example: the use of simple and inexpensive reagents that are compatible with in situ amplification in cells and tissues, providing high signal-to-noise ratio (SNR); the production of spatially compact products, which enable higher spatial resolution of multiple targets with higher imaging quality and resolution; and flexibility of sequence design, facilitating design and implementation of simultaneous multiplexing.

Figure 3A:
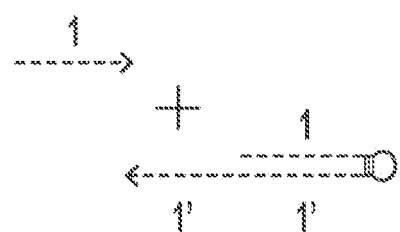
FIGS. 3A-3C: Synthetic "telomerase" reaction.
Figure 3B:
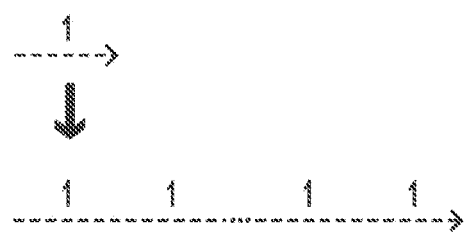
Figure 3C:
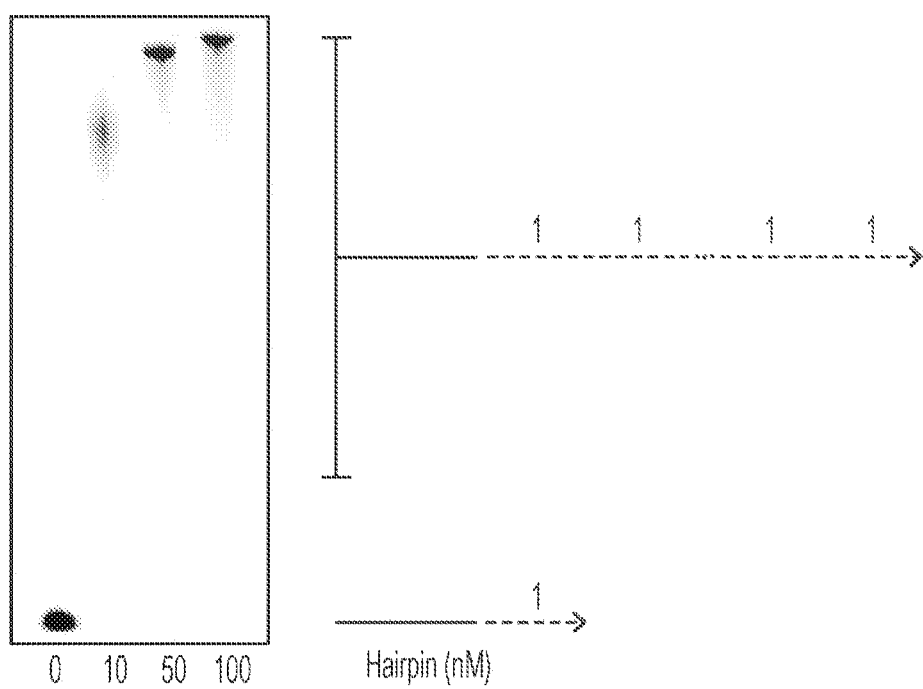

PER pathways involve dynamic synthesis of arbitrary single-stranded DNA (ssDNA) sequences onto a growing primer strand with the aid of a strand-displacing DNA polymerase in an isothermal and autonomous manner. Using a strand-displacing polymerase and a hairpin species that acts catalytically, a primer exchange reaction elongates a primer sequence in an order patterned by the hairpins in solution (FIGS. 3A-3C). Each PER hairpin uses a stop sequence to halt polymerization (29-31). For example, the stop sequence can be a G-C pair if sequence 'a' comprises a three-letter code of A's, T's, and C's, and dGTP is excluded from the mixture of dNTPs. Other stop sequences include chemical modifications and synthetic base pairs, which permit all four letters to be synthesized. For example, synthetic non-DNA linkers which terminate polymerization or iso-dG or iso-dC may be used. Primers can be labeled with a dye on their 5' ends for easy tracking in gel electrophoresis experiments. Hairpins may also include an inverted dT or other modification on their 3' ends to prevent extension on primer strands that could cause the primers to become irreversibly bound. The linear ssDNA structure produced by PER presents an excellent docking platform for binding of short fluorescent oligonucleotides complementary to the repeatedly copied sequence and hence offers a robust way for efficient signal amplification in DNA-based detection. PER signal amplification is both time-efficient and target-specific for effective multiplexing.

Figure 1:
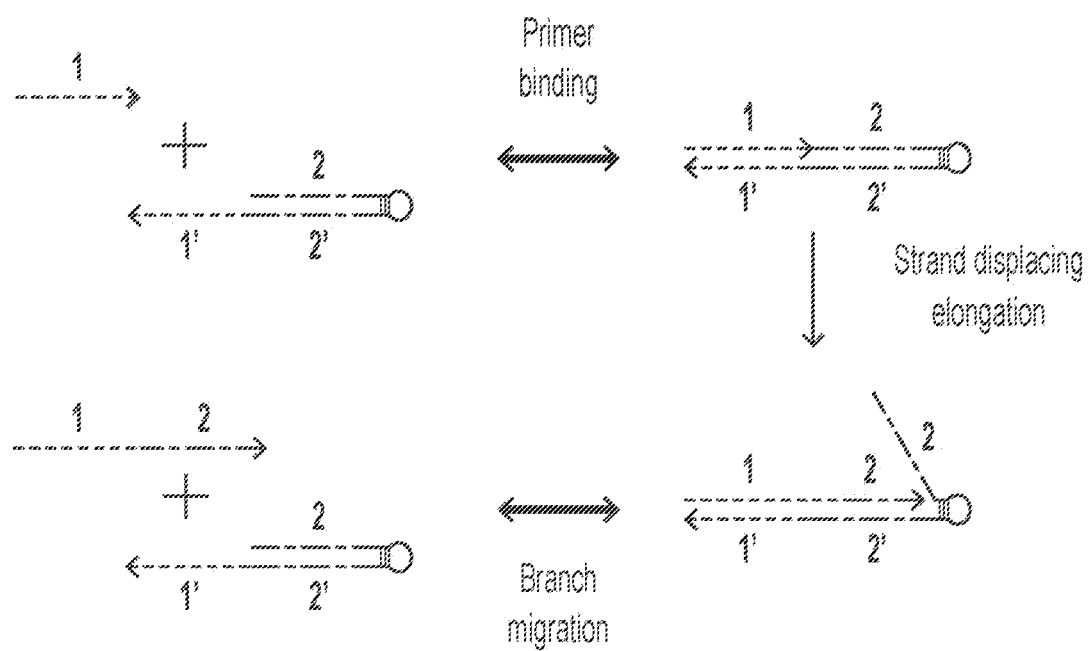
FIG. 1: Basic Primer Exchange Reaction (PER) cycle. A primer with domain 1 first binds to a catalytic hairpin species. Then, a strand displacing polymerase synthesizes domain 2, appending it to the original primer to create the transcript 1+2. Spontaneous dissociation of the primer from the hairpin releases the new transcript into solution, and the hairpin is recycled and available for use in another reaction.

A primer exchange reaction of the present disclosure comprises three general steps (see, e.g., FIG. 1 and FIGS. 3A-3B). First, a probe strand containing a primer domain (carrying sequence "1" on its 3' end) in solution binds to a complementary exposed unpaired (single-stranded) toehold binding region ("1'") on a catalytic molecule (e.g., catalytic hairpin molecule). A strand displacing polymerase subsequently copies the primer sequence ('1') until it reaches a stop sequence (three black lines). In the last step, a branch migration process can displace the extended primer sequence from the catalytic molecule, and the remaining bound region can spontaneously dissociate. The catalytic molecule is then free to interact with another primer domain (is recycled) in another cycle of primer exchange. Although the primer binding and dissociation steps in this copy-and-release procedure are both reversible, the dNTP fueled polymerization step is effectively irreversible. This results in an overall driven reaction process, with dNTPs being consumed but hairpins not. Repetition of this extension process through several reaction cycles produces a long linear single-stranded concatemer of sequence "1" (FIGS. 3A and 3B). A single catalytic hairpin molecule can be used to generate arbitrary length strands by continually concatenating the same domain onto a growing primer strand. In this synthetic "telomerase" PER system, increasing the concentration of the catalytic hairpin molecule in solution increases the rate of telomerization (FIG. 3C). Several telomerization reactions can be performed in parallel, using primers that are sufficiently orthogonal as to not bind and extend on the wrong hairpin.

Figure 2A:
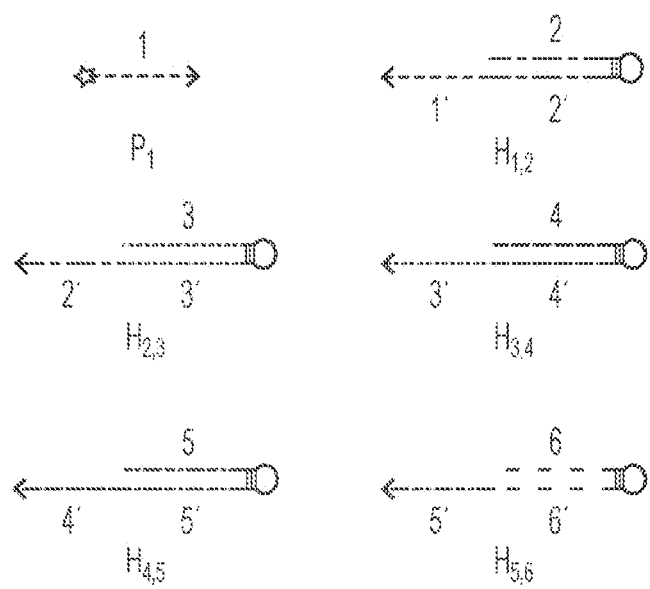
FIGS. 2A-2B: Stepwise synthesis through PER cascades.
Figure 2B:
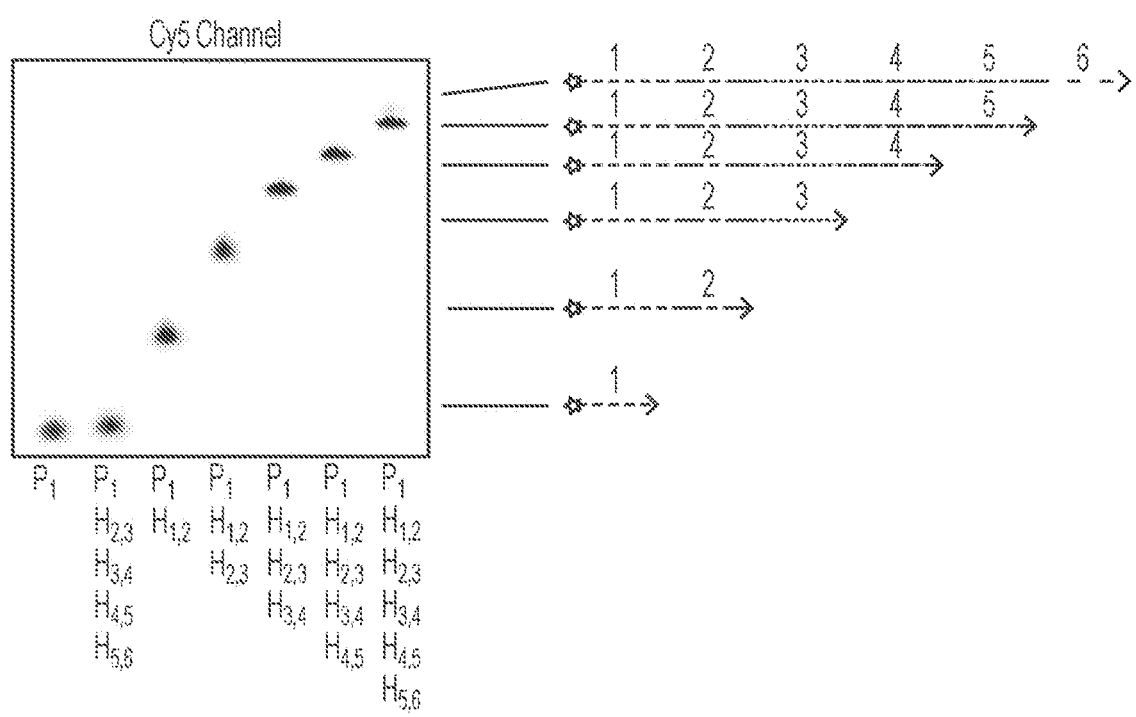

A 5-step PER cascade system depicted in FIGS. 2A and 2B shows how different subsets of five catalytic hairpin molecules mediate different numbers of extension steps.

A typical multi-step multiplexed PER reaction includes, orthogonal probe strands (each containing a different target domain and a different primer domain), catalytic hairpins (each containing a different toehold domain that can bind a primer domain of one of the probe strands), strand-displacing polymerase, buffer, dNTPs and orthogonal signal strands (each containing a domain complementary to a primer domain of a probe strand and each labeled with a spectrally-distinct fluorophore).

As non-limiting examples, the probe strands having a length of 5-50 nucleotides (e.g., 5, 10, 15, 20, 25, 30, 35, 40, 45, or 50 nucleotides, or 5-30, 5-40, 5-60, 10-30, 10-40, 10-50, 15-30, 15-40, 15-50, 20-30, 20-40, 20-50, 25-30, 25-40, or 25-50 nucleotides) may be present in a reaction at a concentration of 1 nM to 1 μM (primers should not extend on non-cognate hairpins); the catalytic hairpins may be also present in a reaction at a concentration of 1 nM to 1 μM; the signal strands having a length of 5-30 nucleotides (e.g., 5, 6, 7, 8, 9, 10, 12, 14, 16, 18, 20, 22, 24, 26, 28, or 30 nucleotides or 5-10, 5-15, 5-30, 10-15, 10-20, 10-25, 10-30, 15-20, 15-25, 15-30, or 20-30 nucleotides) and labeled on their 5' end with a fluorophore (e.g., Cy5) may be present in a reaction at a concentration of 1 nM to 1 μM; the strand-displacing polymerase may be one or more of the non-exonuclease polymerases Bst, Bsm, Klenow (others may be used); the dNTP concentration may be present in a reaction at a concentration of 1 μM to 500 μM; and the buffer may be phosphate buffered saline that includes a $MgSO_4$ concentration of 5 mM to 50 mM (to adjust the speed of the reaction while maintaining specificity) and, in some reactions, dextran sulfate and/or polyacrylic acid to maximize SNR. A working example of a primer exchange reaction is described in Example 2 below.

Figure 4:
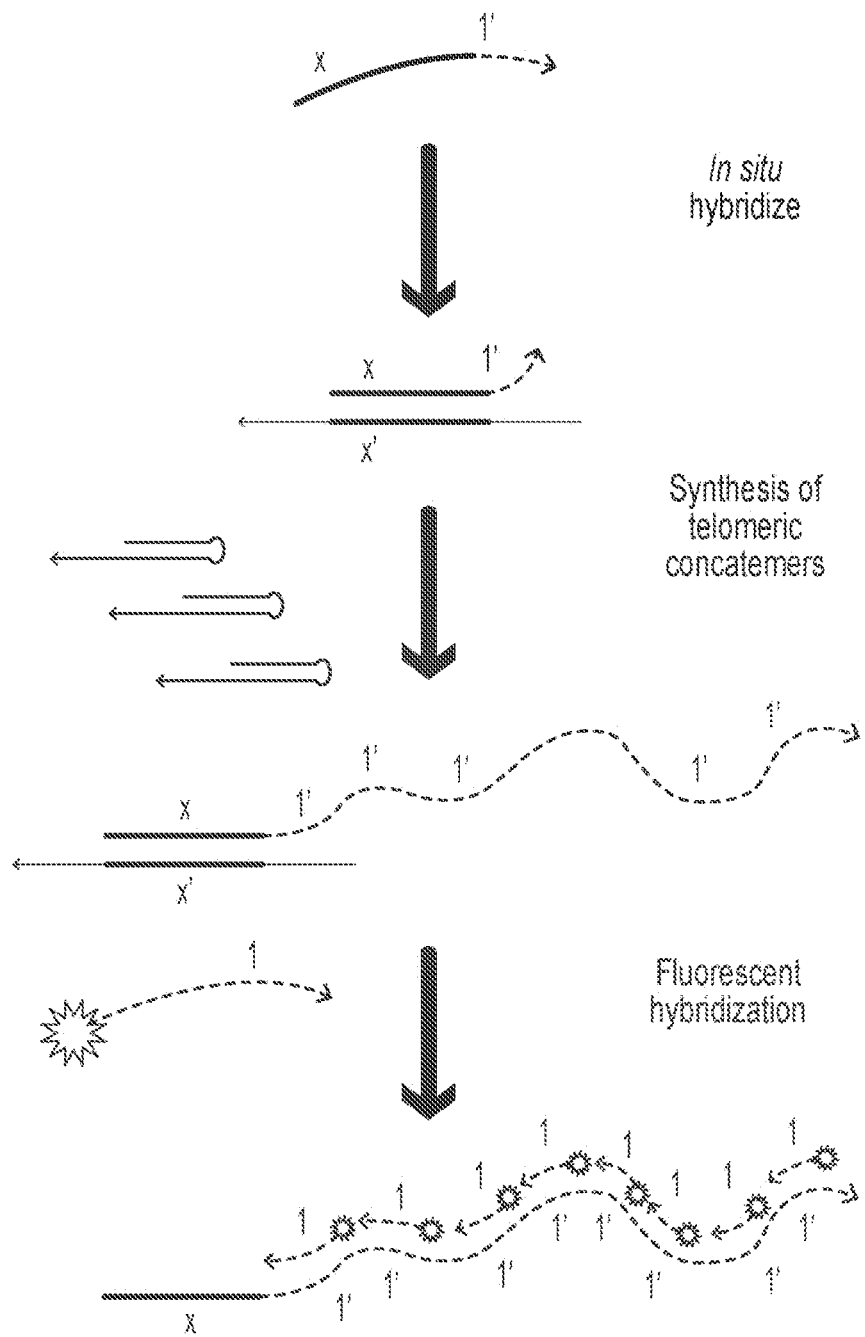
FIG. 4: Basic strategy for in situ amplification. After a probe in hybridized in situ, PER hairpins are used to generate a long repetitive concatemer scaffold sequence. Then, fluorescent strands are hybridized with this scaffold to create a localized amplified signal.
Figure 5A:
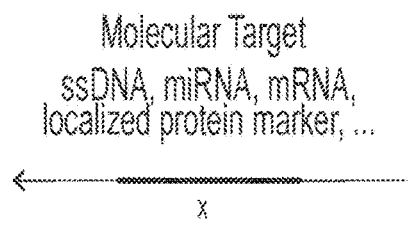
FIGS. 5A-5E: Schematic for localized signal amplification in fixed cells.

The general strategy for amplifying a signal in situ, e.g., for a multiplexed PER reaction, is to grow long fluorescent telomere scaffolds (growing DNA strands) as depicted in FIG. 4. After incubation with catalytic molecules (e.g., catalytic hairpin molecules) to grow a long strand, complementary signal strands (e.g., nucleic acid strands linked to fluorophores) are allowed to bind. This creates an amplified localized fluorescent signal, as several fluorophores can aggregate along a single telomere scaffold. A more detailed schematic of the imaging workflow is shown in FIG. 5. First, a target is chosen (FIG. 5A). If this target is a nucleic acid such as chromosomal DNA, mRNAs, or miRNAs, then a probe (with domain X') that is complementary to the target (domain X) is designed to localize to the target's location in a fixed cell through an in situ hybridization procedure. This probe is fitted with a primer on its 3' end (domain 1), which can be extended using catalytic molecules (e.g., catalytic hairpin molecules). If the target is a protein, then instead of the X domain, the primer may be conjugated to an antibody (or other binding partner) that binds the target protein.

Figure 5B:
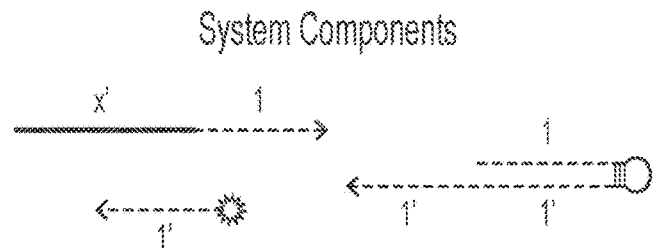
Figure 5C:
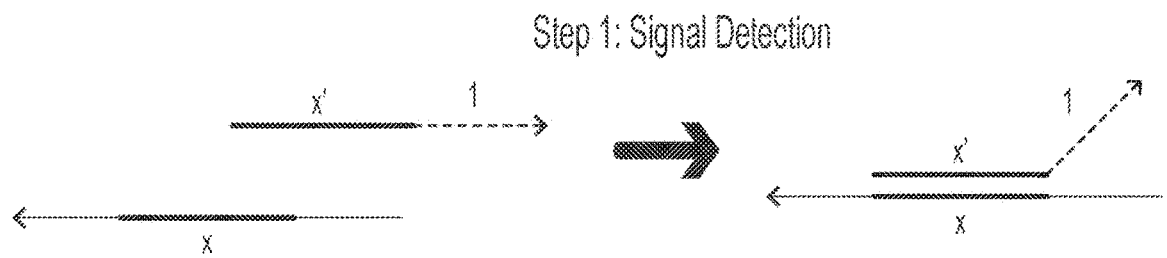

The multiplexed amplification system as provided herein uses a catalytic molecule (e.g., catalytic hairpin molecule) and a fluorescent probe complementary to the repetitive extension domain 1 (FIG. 5B). Imaging is done in a stepwise manner by first localizing the probe to its target (FIG. 5C), then introducing the PER components to grow telomere scaffolds in situ (FIG. 5D), and finally by binding fluorescent signal strands (e.g., complementary oligonucleotides) to these repetitive transcripts (tandem repeat sequences) in order to aggregate several fluorophores in a single localized point (FIG. 5E).

Figure 6A:
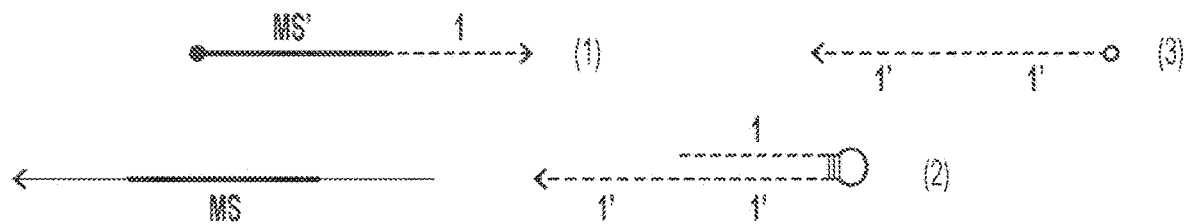
FIGS. 6A-6C: Preliminary experiments for signal amplification in fixed cells.
Figure 6B:
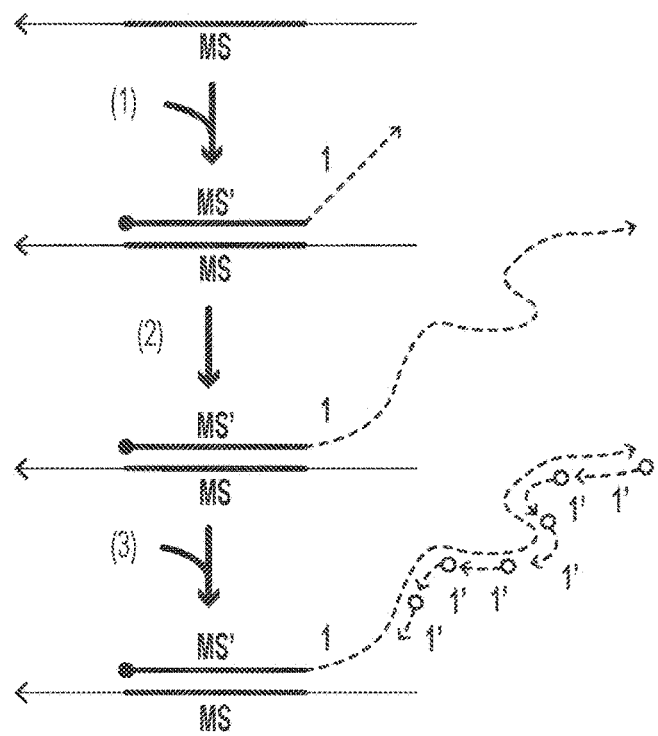
Figure 6C:
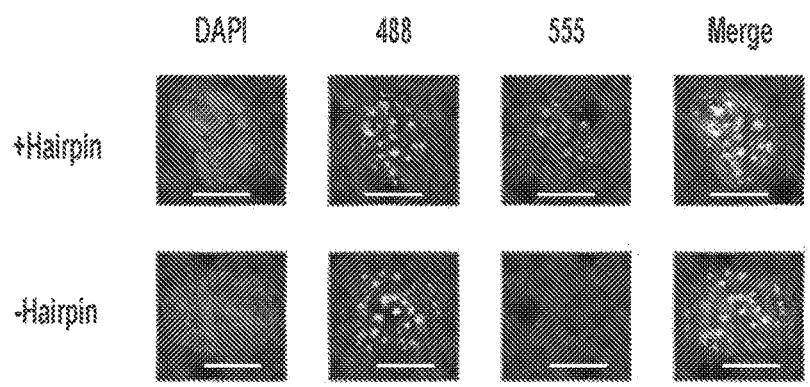

An initial test of the system was performed on fixed immortalized mouse embryonic fibroblast cells using DNA FISH (FIG. 6). The major satellite repeat region of chromosomes was targeted, and a control experiment indicated that telomere induced fluorescence was only present when the PER hairpin was included in the reaction solution.

The molecular components described herein include one or more domains. A domain of a molecule is simply a discrete segment of the molecule. A domain of a nucleic acid molecule (comprising or consisting of nucleotides) is a discrete, contiguous sequence of nucleotides or nucleotide base pairs, depending on whether the domain is unpaired (single-stranded nucleotides) or paired (double-stranded nucleotide base pairs), respectively. In some embodiments, a domain is described as having multiple subdomains for the purpose of defining intramolecular (within the same molecular species) and intermolecular (between two separate molecular species) complementarity. One domain (or one subdomain) is complementary to another domain if one domain contains nucleotides that base pair (hybridize/bind through Watson-Crick nucleotide base pairing) with nucleotides of the other domain such that the two domains form a paired (double-stranded) or partially-paired molecular species/structure. Complementary domains need not be perfectly/wholly (100%) complementary to form a paired structure, although perfect complementarity is provided, in some embodiments. Thus, a primer domain that is complementary to a particular domain, such as the 3' toehold domain of a catalytic molecule, binds to that domain, for example, for a time sufficient to initiate polymerization in the presence of polymerase. FIG. 1, for example, shows primer domain '1' binding to toehold domain '1'' of a catalytic hairpin molecule.

A paired domain (considered a "stem domain" with reference to hairpins) of a catalytic molecule comprised of nucleic acid refers to a paired sequence of nucleotides (e.g., Watson-Crick nucleobase pairing) located 5' from (and, in some embodiments, directly adjacent to) the unpaired toehold domain of a catalytic molecule. The paired domain of a catalytic molecule is formed by nucleotide base pairing between a "displacement strand" and a "template strand" containing a toehold domain. The paired domain (stem domain) of a catalytic hairpin molecule is formed by intramolecular base pairing (base pairing between nucleotides within the same molecule) of two subdomains of a catalytic hairpin molecule: e.g., an internal/central subdomain located 5' from the toehold domain bound (hybridized) to a subdomain located at the 5' end of the catalytic hairpin. The length of a paired domain of a catalytic molecule comprised of nucleic acid may vary. In some embodiments, a paired domain has a length of 5-40 nucleotides. For example, a paired domain may have a length of 5-35, 5-30, 5-25, 5-20, 5-15, 5-10, 10-40, 10-35, 10-30, 10-25, 10-20, 10-15, 15-40, 15-35, 15-30, 15-25, 15-20, 20-40, 20-35, 20-30, 20-25, 25-40, 25-35, 25-30, 30-40, 30-35 or 35-40 nucleotides. In some embodiments, a paired domain has a length of 5, 10, 15, 20, 25, 30, 35 or 40 nucleotides. In some embodiments, a paired domain has a length of 10, 11, 12, 13, 14, 15, 16, 17, 18, 19, 20, 21, 22, 23, 24 or 25 nucleotides. A paired domain, in some embodiments, is longer than 40 nucleotides, or shorter than 5 nucleotides.

While a paired domain is generally formed by intramolecular base pairing of two subdomains of a catalytic molecule, it should be understood that this paired domain may contain at least one mismatch pair (e.g., pairing of A with C or G, or pairing of T with C or G). In some embodiments, the paired domain has 1-5 mismatch nucleotide base pairs. For example, a paired domain may have 1, 2, 3, 4 or 5 mismatch nucleotide base pairs.

A catalytic molecule generally includes an unpaired (single-stranded) 3' toehold domain and a paired (double-stranded) domain 5' from (and, in some embodiments, directly adjacent to) the 3' toehold domain. A catalytic molecule may be comprised of DNA, RNA or a combination of DNA and RNA. Catalytic hairpin molecules further include a loop domain at the end of the molecule opposite to the 3' toehold domain. The kinetics of multiplexed primer exchange reactions can be controlled by modifying the length, composition and concentration of the catalytic molecules (e.g., one or more domains of the catalytic molecules), for example.

A catalytic hairpin molecule (see FIG. 1A as an illustrative example) includes a 3' toehold domain ("1'") linked to a paired stem domain (e.g., formed by intramolecular binding of subdomain "2" to subdomain "2'") linked to a hairpin loop domain (loop-like structure). Thus, in some embodiments, a catalytic hairpin molecule comprises a single nucleic acid strand formed into a hairpin structure through intramolecular base pairing. Catalytic molecules without a loop domain ("duplexes") are also provided herein. The length of a catalytic molecule (e.g., catalytic hairpin molecule) may vary. In some embodiments, a catalytic molecule comprised of nucleic acid has a length (5' to 3') of 25-300 nucleotides. For example, a catalytic molecule comprised of nucleic acid may have a length of 25-250, 25-200, 25-150, 25-100, 25-50, 50-300, 50-250, 50-200, 50-150 or 50-100 nucleotides. In some embodiments, a catalytic molecule comprised of nucleic acid has a length of 30-50, 40-60, 50-70, 60-80, 70-90, 80-100, 100-125, 100-150 or 100-200 nucleotides. In some embodiments, a catalytic molecule comprised of nucleic acid has a length of 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 nucleotides. A catalytic molecule comprised of nucleic acid, in some embodiments, is longer than 300 nucleotides, or shorter than 25 nucleotides.

A toehold domain is an unpaired domain located at the 3' end of the catalytic molecule (an unpaired 3' domain) and binds to a primer domain of a probe strand. In some embodiments, a toehold domain (and thus the catalytic molecule) comprise a nucleotide sequence complementary to (wholly or partially, e.g., in length and/or nucleotide composition) a primer domain of a probe strand. In some embodiments, the toehold domain nucleotide sequence is longer or shorter than the primer domain of the probe strand. In other embodiments, the toehold domain nucleotide sequence is the same length as the primer domain of the probe strand. The length of a toehold domain may vary. In some embodiments, a toehold domain has a length of 5-40 nucleotides. For example, a toehold domain may have a length of 2-35, 2-30, 2-25, 2-20, 2-15, 2-10, 5-35, 5-30, 5-25, 5-20, 5-15, 5-10, 10-40, 10-35, 10-30, 10-25, 10-20, 10-15, 15-40, 15-35, 15-30, 15-25, 15-20, 20-40, 20-35, 20-30, 20-25, 25-40, 25-35, 25-30, 30-40, 30-35 or 35-40 nucleotides. In some embodiments, a toehold domain has a length of 5, 10, 15, 20, 25, 30, 35 or 40 nucleotides. In some embodiments, a toehold domain has a length of 10, 11, 12, 13, 14, 15, 16, 17, 18, 19, 20, 21, 22, 23, 24 or 25 nucleotides. A toehold domain, in some embodiments, is longer than 40 nucleotides, or shorter than 5 nucleotides.

A loop domain of a catalytic hairpin molecule refers to a primarily unpaired sequence of nucleotides that form a loop-like structure at the end (adjacent to) of the stem domain (opposite the 3' toehold domain). The length of a loop domain may vary. In some embodiments, a loop domain of a catalytic hairpin molecule comprised of nucleic acid has a length 3-200 nucleotides. For example, a loop domain may have a length of 3-175, 3-150, 3-125, 3-100, 3-75, 3-50, 3-25, 4-175, 4-150, 4-125, 4-100, 4-75, 4-50, 4-25, 5-175, 5-150, 5-125, 5-100, 5-75, 5-50 or 5-25 nucleotides. In some embodiments, a loop domain has a length of 3-10, 3-15, 32-10, 3-25, 3-30, 3-35, 3-40, 3-35, 3-40, 3-45, 3-50, 4-10, 4-15, 4-10, 4-25, 4-30, 4-35, 4-40, 4-35, 4-40, 4-45 or 4-50 nucleotides. In some embodiments, a loop domain has a length of 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 45, 46, 47, 48, 49 or 50 nucleotides. A loop domain, in some embodiments, is longer than 300 nucleotides.

In some embodiments, a catalytic molecule does not contain a hairpin loop domain. For example, a catalytic molecule may simply be a duplex comprising a 3' unpaired toehold domain adjacent to a paired domain, similar to a stem domain (without the adjacent loop domain). Catalytic molecules that do not include a loop domain may be stabilized at the end opposite the 3' toehold domain through crosslinking or nucleotide base complementarity between a stretch (e.g., 10 or more) nucleotide base pairs.

A probe strand, in some embodiments, includes an unpaired 5' target domain that binds to a molecular target and an unpaired 3' primer domain that binds to the unpaired 3' toehold domain of a catalytic molecule to initiate a multiplexed primer exchange reaction. A probe strand, in some embodiments, is comprised of DNA, RNA or a combination of DNA and RNA. In a multiplexed PER reaction (see probe strand in FIG. 5B and simplified version without target domain in FIG. 1 as an illustrative example), the primer domain ("1") of a probe strand binds to the toehold domain of a catalytic molecule ("1'"), and extension of the primer by a strand displacement polymerase present in the reaction solution displaces one of the subdomains ("2") of the stem domain of the catalytic molecule through a branch migration process. The overall effect is that one of the subdomains ("2") of the hairpin stem domain is replaced with the extended (newly synthesized) primer domain.

In some embodiments, a probe strand (comprising a target domain and primer domain) has a length of 10-50 nucleotides. For example, a probe strand may have a length of 10-45, 10-40, 10-35, 10-30, 10-25, 10-20, 10-15, 15-50, 15-45, 15-40, 15-35, 15-30, 15-25, 15-20, 20-50, 20-45, 20-40, 20-35, 20-30, 20-25, 25-50, 25-45, 25-40, 25-35, 25-30, 30-50, 30-45, 30-40, 30-35, 35-50, 35-45, 35-40, 40-50, 40-45 or 45-50 nucleotides. In some embodiments, a probe strand has a length of 10, 15, 20, 25, 30, 35, 40, 45 or 50 nucleotides. In some embodiments, a probe strand has a length of 15, 16, 17, 18, 19, 20, 21, 22, 23, 24 or 25 nucleotides. A probe strand, in some embodiments, is longer than 50 nucleotides, or shorter than 10 nucleotides.

In some embodiments, a primer domain (the nucleotide sequence that binds to the toehold domain of a catalytic molecule) has a length of 10-30 nucleotides. For example, a primer domain may have a length of 10-25, 10-20, 10-15, 15-30, 15-25, 15-20, 20-30, 20-25, or 25-30, nucleotides. In some embodiments, a primer domain has a length of 10, 15, 20, 25, or 30 nucleotides. In some embodiments, a primer domain has a length of 15, 16, 17, 18, 19, 20, 21, 22, 23, 24 or 25 nucleotides.

In some embodiments, extension of a primer domain (bound to a primer-binding site) by a displacing polymerase is terminated by the presence of a molecule or modification in the catalytic molecule that terminates polymerization. Thus, in some embodiments, catalytic molecules of the present disclosure comprise a molecule or modification that terminates polymerization. A molecule or modification that terminates polymerization ("stopper") is typically located in a paired domain (e.g., stem domain) of a catalytic molecule such that polymerization terminates extension of the primer through the paired domain. For catalytic molecules arranged in the form of a hairpin, a molecule or modification that terminates polymerization may be located between the paired stem domain and the loop domain (see 3 straight black lines in catalytic hairpin molecule of FIG. 1, for example). In some embodiments, the molecule that terminates polymerization is a synthetic non-DNA linker, for example, a triethylene glycol spacer, such as the Int Spacer 9 (iSp9) or Spacer 18 (Integrated DNA Technologies (IDT)). It should be understood that any non-native linker that terminates polymerization by a polymerase may be used as provided herein. Other non-limiting examples of such molecules and modifications include a three-carbon linkage (Int C3 Spacer, iSpC3) (IDT), ACRYDITE™ (IDT), adenylation, azide, digoxigenin (NHS ester), cholesteryl-TEG (IDT), I-LINKER™ (IDT), and 3-cyanovinylcarbazole (CNVK) and variants thereof. Typically, but not always, short linkers (e.g., iSp9) lead to faster reaction times.

In some embodiments, the molecule that terminates polymerization is a single or paired non-natural nucleotide sequence, such as iso-dG and iso-dC (IDT), which are chemical variants of cytosine and guanine, respectively.

Iso-dC will base pair (hydrogen bond) with Iso-dG but not with dG. Similarly, Iso-dG will base pair with Iso-dC but not with dC. By incorporating these nucleotides in a pair on opposite sides of the hairpin, at the stopper position, the polymerase will be halted, as it does not have a complementary nucleotide in solution to add at that position.

In some embodiments, the efficiency of performance of a "stopper" modification is improved by lowering dNTP concentrations (e.g., from 200 µM) in a reaction to 100 µM, 10 µM, 1 µM, or less.

Inclusion of a molecule or modification that terminates polymerization often creates a bulge in a paired domain of catalytic molecule (e.g., a stem domain for hairpin structures), because the molecule or modification is not paired. Thus, in some embodiments, catalytic molecules are designed to include, opposite the molecule or modification, a single nucleotide (e.g., thymine), at least two of same nucleotide (e.g., a thymine dimer (TT) or trimer (TTT)), or a non-natural modification.

A target domain of a probe strand binds, directly or indirectly, to a molecular target. For example, when a molecular target is a nucleic acid target (e.g., chromosomal DNA, mRNA or miRNA), the target domain may be designed to include a nucleotide sequence complementary to a domain of the nucleic acid target such that the target domain (and thus the probe strand) binds directly to the nucleic acid target (see, e.g., FIGS. 5A-5E). When the molecule target is a protein or peptide, however, binding of the probe strand to the protein or peptide target may be indirect. In such embodiments, a primary and/or secondary antibody(ies) (or other binding partner(s)) may be used to first locate the protein or peptide target, and then (1) a "prefabricated" concatemer is appended to the antibody (see, e.g., FIG. 10A) or (2) the probe strand binds to the primary or secondary antibody (or other binding partner) via an intermediate bridge strand appended to the antibody. For example, a primary antibody may be modified with a "bridge strand" (an unpaired nucleic acid strand) that include a domain complementary to the 5' target domain of the probe strand such that the probe strand can bind to the bridge strand of the primary antibody to initiate a multiplexed primer exchange reaction in the presence of a catalytic molecule and polymerase. Alternatively, a (an unmodified) primary antibody (specific to the molecule target) may be used to locate the protein or peptide target, and then a secondary antibody (specific to the primary antibody) modified with a bridge strand is used to locate the primary antibody. The probe strand then binds to the bridge strand of the secondary antibody to initiate a multiplexed primer exchange reaction in the presence of a catalytic molecule and polymerase. In yet other embodiments, the probe strand appended to an antibody may itself function as a primer (primer domain) to initiate a primer exchange reaction by binding directly to the toehold domain of the catalytic molecule (see, e.g., FIG. 10B).

In some embodiments, the methods comprise combining a sample containing a plurality of protein or peptide targets with a plurality of binding partners to form a first reaction mixture before combining the first reaction mixture with dNTPs, strand-displacing polymerase, a plurality of catalytic molecules, and a plurality of probe strands encompasses both stepwise and simultaneous addition of the various elements (dNTPs, polymerase, catalytic molecules, and probe strands). For example, in some instances, a user may prefer to add the probe to the reaction mixture to prehybridize the probe before adding the dNTPs, polymerase, and catalytic molecules.

Some embodiments described herein employ a primary binding partner that binds to the molecular target (i.e., a protein or peptide target). The primary binding partner may be an antibody, or any other binding partner that can bind specifically to the molecular target. It should be understood that the term antibody encompasses full-length antibodies and antigen-binding antibody fragments, unless otherwise noted. Thus, in some embodiments, a primary binding partner may be a full-length antibody, and in other embodiments, a primary binding partner may be an antigen-binding antibody fragment. Additionally, some embodiments employ a secondary binding partner that binds to the primary binding partner. The secondary binding partner, in some embodiments, is an antibody, such as a full-length antibody or an antigen-binding antibody fragment. Other binding partners may be used as a secondary binding partner.

When the molecular target is a protein or peptide, the molecule that binds to the molecule target need not be an antibody. Any molecule (any 'binding partner') that can bind specifically to the molecular target may be used. Thus, a binding partners includes target binding antibodies or any type of antigen-binding fragment thereof. Additionally, for example, if a molecular target is a protein ligand, then the molecule modified with a bridge strand may be a receptor to that ligand. In some embodiments, fusion proteins, peptides, protein fragments, toxins, lipids, or affinity probes including but not limited to nanobodies, affibodies, single-chain variable fragments and aptamers may be used to locate (bind to) a molecular target. Other binding partner (e.g., protein-binding partner) interactions are encompassed herein. Likewise, other secondary probes that bind to binding partners including but not limited to protein A, protein G or antibody-specific nanobodies may be used, in some embodiments, to locate (bind to) binding partners.

Figure 5D:
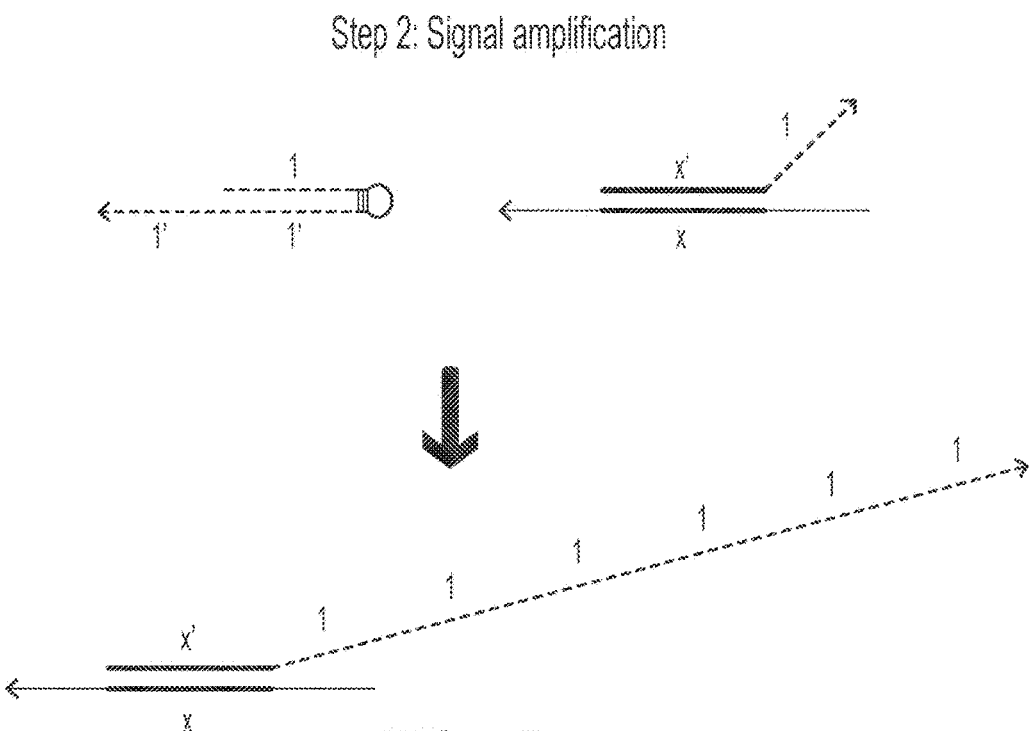
Figure 5E:
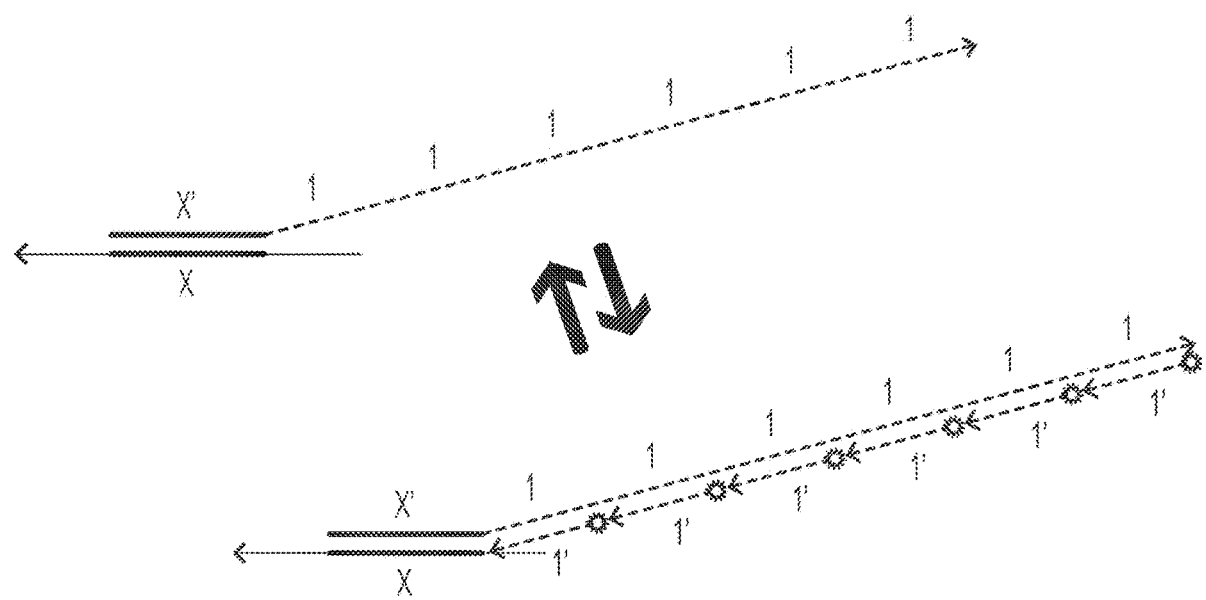

A multiplexed primer exchange reaction, as shown in FIGS. 5A-5E results in the production of a long nucleic acid concatemer (see, e.g., FIG. 5D). A probe strand bound to a molecular target (in the presence of polymerase) interacts with catalytic molecules to produce a growing strand of, in some embodiments, tandem repeat sequences. This concatemer of tandem repeat sequences serves as the foundation for the amplified signal. Once the concatemer is produced, signal strands can bind to the concatemer to produce amplified signal (FIG. 5E).

A signal strand thus binds to a concatemer. A signal strand, in some embodiments, includes a sequence complementary to the primer domain of a probe strand such that the signal strand can bind to the concatemer produced from the growing probe strand. A signal strand is linked to (labeled with) a detectable molecule (e.g., a molecule that emits a detectable signal, such as a fluorescent or chemiluminescent signal). In some embodiments, the label is a fluorophore. A primer linked to a fluorophore or other fluorescent/chemiluminescent molecule is referred to simply as a "fluorescent primer." Examples of fluorophores that may be used herein include, without limitation, hydroxycoumarin, methoxycoumarin, Alexa fluor, aminocoumarin, Cy2, FAM, Alexa fluor 405, Alexa fluor 488, Fluorescein FITC, Alexa fluor 430, Alexa fluor 532, HEX, Cy3, TRITC, Alexa fluor 546, Alexa fluor 555, R-phycoerythrin (PE), Rhodamine Red-X, Tamara, Cy3.5 581, Rox, Alexa fluor 568, Red 613, Texas Red, Alexa fluor 594, Alexa fluor 633, Allophycocyanin, Alexa fluor 647, Cy5, Alexa fluor 660, Cy5.5, TruRed, Alexa fluor 680, Cy7 and Cy7.5. Other fluorophores and molecules that emit a detectable signal are encompassed by the present disclosure.

Multiplexed primer exchange reactions require the use of a polymerase. In some embodiments, the polymerase is a DNA polymerase (DNAP), such as a DNA polymerase having DNA strand displacement activity (a strand displacement polymerase). "Strand displacement" describes the ability to displace downstream DNA encountered during synthesis. Examples of polymerases having DNA strand displacement activity (a strand-displacing polymerase) that may be used as provided herein include, without limitation, phi29 DNA polymerase (e.g., NEB #M0269), Bst DNA polymerase, large fragment (e.g., NEB #M0275), or Bsu DNA polymerase, large fragment (e.g., NEB #M0330). Other polymerases having strand displacement activity may be used. In some embodiments, the polymerase is a RNA polymerase.

In some embodiments, the polymerase is phi29 DNA polymerase. In such embodiments, the reaction conditions may be as follows: 1× reaction buffer (e.g., 50 mM Tris-HCl, 10 mM MgCl$_2$, 10 mM (NH$_4$)$_2$SO$_4$, 4 mM DTT) supplement with purified bovine serum albumin (BSA), pH 7.5, incubated at 30° C.

In some embodiments, the polymerase is Bst DNA polymerase, large fragment. In such embodiments, the reaction conditions may be as follows: 1× reaction buffer (e.g., 20 mM Tris-HCl, 10 mM (NH$_4$)$_2$SO$_4$, 10 mM KCl, 2 mM MgSO$_4$, 0.1% TRITON® X-100), pH 8.8, incubated at 65° C.

In some embodiments, the polymerase is Bsu DNA polymerase. In such embodiments, the reaction conditions may be as follows: 1× reaction buffer (e.g., 50 mM NaCl, 10 mM Tris-HCl, 10 mM MgCl$_2$, 1 mM DTT), pH 7.9, incubated at 37° C.

The concentration of primer, catalytic molecules and dNTPs in a multiplexed primer exchange reaction system may be varied depending, for example, on the particular application and kinetics required for that particular application.

The concentration of primer in a multiplexed primer exchange reaction may be, for example, 10 nM to 1000 nM. In some embodiments, the primer concentration in a multiplexed primer exchange reaction is 10-20, 10-30, 10-40, 10-50, 10-60, 10-70, 10-80, 10-90, 10-100, 10-125, 10-150, 10-200, 25-50, 25-75, 25-100, 25-150, 25-200, 50-75, 50-100, 50-150 or 50-200 nM. In some embodiments, the primer concentration in a multiplexed primer exchange reaction is 100-200, 100-300, 100-400, 100-500, 100-600, 100-70, 100-800, 100-900 or 100-1000 nM. In some embodiments, the primer concentration in a multiplexed primer exchange reaction is 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195 or 200 nM. In some embodiments, the primer concentration in a multiplexed primer exchange reaction is 100, 200, 300, 400, 500, 600, 700, 800, 900 or 1000 nM. The concentration of primer in a multiplexed primer exchange reaction may be less than 10 nM or greater than 1000 nM.

The concentration of catalytic molecules (e.g., catalytic hairpins) in a multiplexed primer exchange reaction may be, for example, 5 nM to 1000 nM. In some embodiments, the catalytic molecule concentration in a multiplexed primer exchange reaction is 5-10, 5-20, 5-30, 5-40, 5-50, 5-60, 5-70, 5-80, 5-90, 5-100, 5-125, 5-150, 5-200, 10-50, 10-75, 10-100, 10-150, 10-200, 25-75, 25-100, 25-125 or 25-200 nM. In some embodiments, the catalytic molecule concentration in a multiplexed primer exchange reaction is 10-200, 10-300, 10-400, 10-500, 10-600, 10-70, 10-800, 10-900 or 10-100 nM. In some embodiments, the catalytic molecule concentration in a multiplexed primer exchange reaction is 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195 or 200 nM. In some embodiments, the catalytic molecule concentration in a multiplexed primer exchange reaction is 10, 20, 30, 40, 50, 60, 70, 80, 90 or 100 nM. The concentration of catalytic molecule in a multiplexed primer exchange reaction may be less than 5 nM or greater than 1000 nM.

The ratio of primer to catalytic molecule in multiplexed primer exchange reaction may be 2:1 to 100:1. In some embodiments, the ratio of primer to catalytic molecule is 2:1, 3:1, 4:1, 5:1, 6:1, 7:1, 8:1, 9:1, 10:1, 11:1, 12:1, 13:1, 14:1, 15:1, 16:1, 17:1, 18:1, 19:1 or 20:1. In some embodiments, the ratio of primer to catalytic molecule is 30:1, 40:1, 50:1, 60:1, 70:1, 80:1 or 90:1.

The number of different catalytic molecules in a multiplexed primer exchange reaction in non-limiting. A multiplexed primer exchange reaction may comprise 1-10$^{10}$ different catalytic molecules (each with a specific toehold domain sequence, for example). In some embodiments, a multiplexed primer exchange reaction comprises 1-10, 1-10$^2$, 1-10$^3$, 1-10$^4$, 1-10$^5$, 1-10$^6$, 1-10$^7$, 1-10$^8$, 1-10$^9$, 1-10$^{10}$, or more, different catalytic molecules. In some embodiments, a multiplexed primer exchange reaction comprises 1-5, 1-10, 1-15, 1-20, 1-25, 1-30, 1-35, 1-40, 1-45, 1-50, 1-55, 1-60, 1-65, 1-70, 1-75, 1-80, 1-85, 1-90, 1-95, 1-100, 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 10-15, 10-20, 10-25, 10-30, 10-35, 10-40, 10-45, 10-50, 10-55, 10-60, 10-65, 10-70, 10-75, 10-80, 10-85, 10-90, 10-95 or 10-100 different catalytic molecules. In some embodiments, a multiplexed primer exchange reaction comprises 1, 2, 3, 4, 5, 6, 7, 8, 9, 10, 11, 12, 13, 14, 15, 16, 17, 28, 19, 20, 21, 22, 23, 24 or 25 different catalytic molecules. Catalytic molecules are different from each other if their toehold domains differ from each other, for example.

The kinetics of a multiplexed primer exchange reaction may be controlled by varying temperature, time, buffer/salt conditions, and deoxyribonucleotide triphosphate (dNTP) concentrations, for example. Polymerases, like most enzymes, are sensitive to many buffer conditions, including ionic strength, pH and types of metal ions present (e.g., sodium ions vs. magnesium ions). Thus, the temperature at which a multiplexed primer exchange reaction is performed may vary from, for example, 4° C. to 65° C. (e.g., 4° C., 25° C., 37° C., 42° C. or 65° C.). In some embodiments, the temperature at which a multiplexed primer exchange reaction is performed is 4-25° C., 4-30° C., 4-35° C., 4-40° C., 4-45° C., 4-50° C., 4-55° C., 4-60° C., 10-25° C., 10-30° C., 10-35° C., 10-40° C., 10-45° C., 10-50° C., 10-55° C., 10-60° C., 25-30° C., 25-35° C., 25-40° C., 25-45° C., 25-50° C., 25-55° C., 25-60° C., 25-65° C., 35-40° C., 35-45° C., 35-50° C., 35-55° C., 35-60° C., or 35-65° C. In some embodiments, a multiplexed primer exchange reaction is performed at room temperature, while in other embodiments, a multiplexed primer exchange reaction is performed at 37° C.

A multiplexed primer exchange reaction may be performed (incubated) for 30 minutes (min) to 24 hours (hr). In some embodiments, a multiplexed primer exchange reaction is carried out for 10 min, 35 min, 40 min, 45 min, 50 min, 55 min, 60 min, 1 hr, 2 hr, 3 hr, 4 hr, 5 hr, 6 hr, 7 hr, 8 hr, 9 hr, 10 hr, 11 hr, 12 hr, 18 hr or 24 hr.

Deoxyribonucleotides (dNTPs) are the "fuel" that drives a multiplexed primer exchange reaction. Thus, the kinetics of a multiplexed primer exchange reaction, in some embodiments, depends heavily on the concentration of dNTPs in a reaction. The concentration of dNTPs in a multiplexed primer exchange reaction may be, for example, 2-1000 µM. In some embodiments, the dNTP concentration in a multiplexed primer exchange reaction is 2-10 µM, 2-15 µM, 2-20 µM, 2-25 µM, 2-30 µM, 2-35 µM, 2-40 µM, 2-45 µM, 2-50 µM, 2-55 µM, 2-60 µM, 2-65 µM, 2-70 µM, 2-75 µM, 2-80 µM, 2-85 µM, 2-90 µM, 2-95 µM, 2-100 µM, 2-110 µM, 2-120 µM, 2-130 µM, 2-140 µM, 2-150 µM, 2-160 µM, 2-170 µM, 2-180 µM, 2-190 µM, 2-200 µM, 2-250 µM, 2-300 µM, 2-350 µM, 2-400 µM, 2-450 µM, 2-500 µM, 2-600 µM, 2-700 µM, 2-800 µM, 2-900 µM or 2-1000 µM. For example, the dNTP concentration in a multiplexed primer exchange reaction may be 2 µM, 5 µM, 10 µM, 15 µM, 20 µM, 25 µM, 30 µM, 35 µM, 40 µM, 45 µM, 50 µM, 55 µM, 60 µM, 65 µM, 70 µM, 75 µM, 80 µM, 85 µM, 90 µM, 95 µM, 100 µM, 105 µM, 110 µM, 115 µM, 120 µM, 125 µM, 130 µM, 135 µM, 140 µM, 145 µM, 150 µM, 155 µM, 160 µM, 165 µM, 170 µM, 175 µM, 180 µM, 185 µM, 190 µM, 195 µM or 200 µM. In some embodiments, the dNTP concentration in a multiplexed primer exchange reaction is 10-20 µM, 10-30 µM, 10-40 µM, 10-50 µM, 10-60 µM, 10-70 µM, 10-80 µM, 10-90 µM or 10-100 µM.

In some embodiments, dNTP variants are used. For example, PER systems may use hot start/clean amp dNTPs, phosphorothioate dNTPs, or fluorescent dNTPs. Other dNTP variants may be used. Because some modified dNTPs are less favorable than normal (unmodified) DNA-DNA binding, the hairpin back displacement process may be increased with their usage. Similarly, a hairpin comprised of a different type of nucleic acid (e.g., LNA, RNA or interspersed modified bases such as methyl dC or super T IDT modifications) may be used in some embodiments to increase the speed of a PER by forming stronger bonds than the synthesized primer with respect to the catalytic molecule.

In some embodiments, catalytic molecules are covalently linked to biomolecules such as fluorophores or proteins. In some embodiments, catalytic molecules contain a biotin modification, so they may be tethered to surfaces by a biotin-streptavidin bond. In some embodiments, catalytic molecules contain a modification such as an azide modification within one of the subdomains that allows them to be covalently linked to other molecules such as an alkyne through click chemistry. Other chemical and biological linkages are encompassed by the present disclosure.

It should be understood that the nucleic acids of the present disclosure do not occur in nature. Thus, the nucleic acids may be referred to as "engineered nucleic acids." An engineered nucleic acid is a nucleic acid (e.g., at least two nucleotides covalently linked together, and in some instances, containing phosphodiester bonds, referred to as a phosphodiester backbone) that does not occur in nature. Engineered nucleic acids include recombinant nucleic acids and synthetic nucleic acids. A recombinant nucleic acid is a molecule that is constructed by joining nucleic acids (e.g., isolated nucleic acids, synthetic nucleic acids or a combination thereof) and, in some embodiments, can replicate in a living cell. A synthetic nucleic acid is a molecule that is amplified or chemically, or by other means, synthesized. A synthetic nucleic acid includes those that are chemically modified, or otherwise modified, but can base pair with (also referred to as "binding to," e.g., transiently or stably) naturally-occurring nucleic acid molecules. Recombinant and synthetic nucleic acids also include those molecules that result from the replication of either of the foregoing.

While an engineered nucleic acid, as a whole, is not naturally-occurring, it may include wild-type nucleotide sequences. In some embodiments, an engineered nucleic acid comprises nucleotide sequences obtained from different organisms (e.g., obtained from different species). For example, in some embodiments, an engineered nucleic acid includes a murine nucleotide sequence, a bacterial nucleotide sequence, a human nucleotide sequence, a viral nucleotide sequence, or a combination of any two or more of the foregoing sequences. In some embodiments, an engineered nucleic acid contains one or more random bases.

In some embodiments, an engineered nucleic acid of the present disclosure may comprise a backbone other than a phosphodiester backbone. For example, an engineered nucleic acid, in some embodiments, may comprise phosphoramide, phosphorothioate, phosphorodithioate, O-methylphosphoroamidite linkages, peptide nucleic acids or a combination of any two or more of the foregoing linkages. An engineered nucleic acid may be single-stranded (ss) or double-stranded (ds), as specified, or an engineered nucleic acid may contain portions of both single-stranded and double-stranded sequence. In some embodiments, an engineered nucleic acid contains portions of triple-stranded sequence, or other non-Watson-Crick base pairing such as G-quartets, G-quadruplexes, and i-motifs. An engineered nucleic acid may comprise DNA (e.g., genomic DNA, cDNA or a combination of genomic DNA and cDNA), RNA or a hybrid molecule, for example, where the nucleic acid contains any combination of deoxyribonucleotides and ribonucleotides (e.g., artificial or natural), and any combination of two or more bases, including uracil, adenine, thymine, cytosine, guanine, inosine, xanthine, hypoxanthine, isocytosine and isoguanine. It should also be understood that engineered nucleic acids may by modified with functional groups (e.g., crosslinking chemistries, e.g., azide functional group, alkyne functional group, biotin functional group, 6-FAM functional group, 5-TAMRA functional group and/or 5-Bromo dU).

Engineered nucleic acids of the present disclosure may be produced using standard molecular biology methods (see, e.g., *Green and Sambrook, Molecular Cloning*, A Laboratory Manual, 2012, Cold Spring Harbor Press). In some embodiments, nucleic acids are produced using GIBSON ASSEMBLY® Cloning (see, e.g., Gibson, D. G. et al. *Nature Methods,* 343-345, 2009; and Gibson, D. G. et al. *Nature Methods,* 901-903, 2010, each of which is incorporated by reference herein). GIBSON ASSEMBLY® typically uses three enzymatic activities in a single-tube reaction: 5' exonuclease, the 3' extension activity of a DNA polymerase and DNA ligase activity. The 5' exonuclease activity chews back the 5' end sequences and exposes the complementary sequence for annealing. The polymerase activity then fills in the gaps on the annealed domains. A DNA ligase then seals the nick and covalently links the DNA fragments together. The overlapping sequence of adjoining fragments is much longer than those used in Golden Gate Assembly, and therefore results in a higher percentage of correct assemblies. Other methods of producing engineered nucleic acids are known in the art and may be used in accordance with the present disclosure. For example, a subset of strands may be amplified from a microarray library containing many (e.g., hundreds or thousands) of unique strands.

Branched Variants

Figure 17:
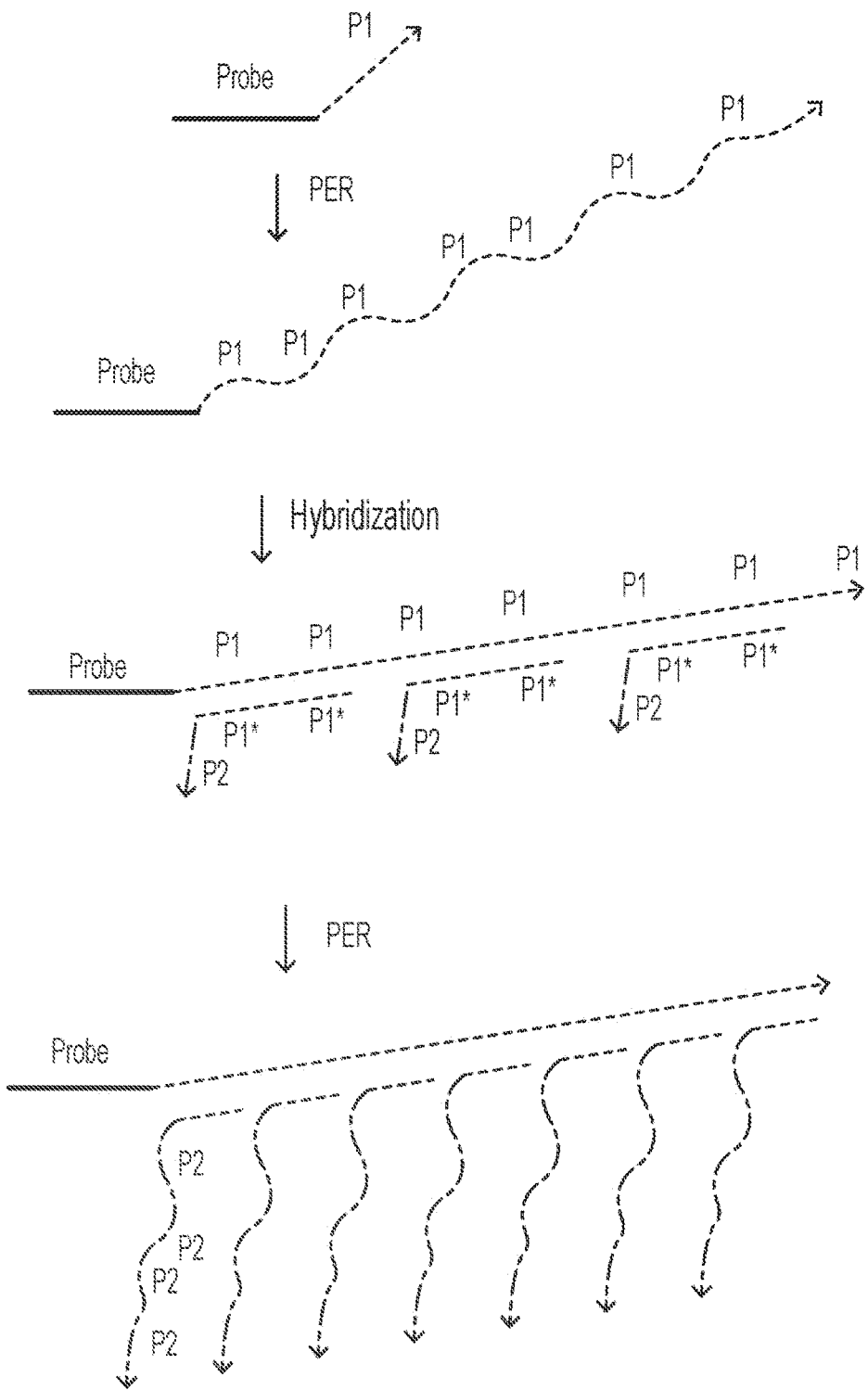
FIG. 17: PER branching variants. The PER-generated concatemers may be used as probe binding sites to form branched structures.
Figure 18:
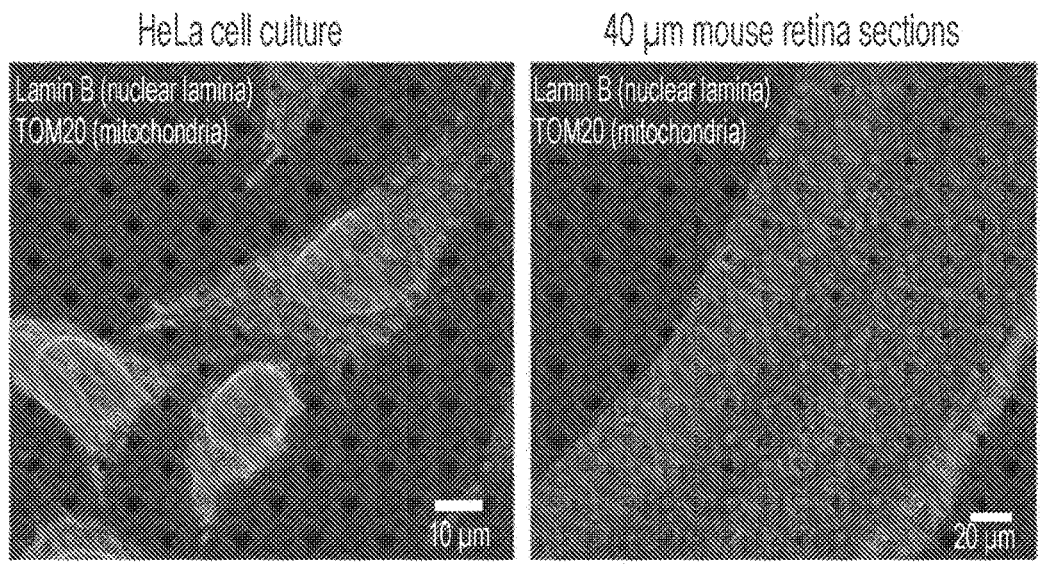
FIG. 18: Example of spectral multiplexing. Two-color immunostaining (cells on the left, retina tissue on the right) using secondary antibodies conjugated to oligos, which are then hybridized to in vitro extended PER strands.
Figure 22A:
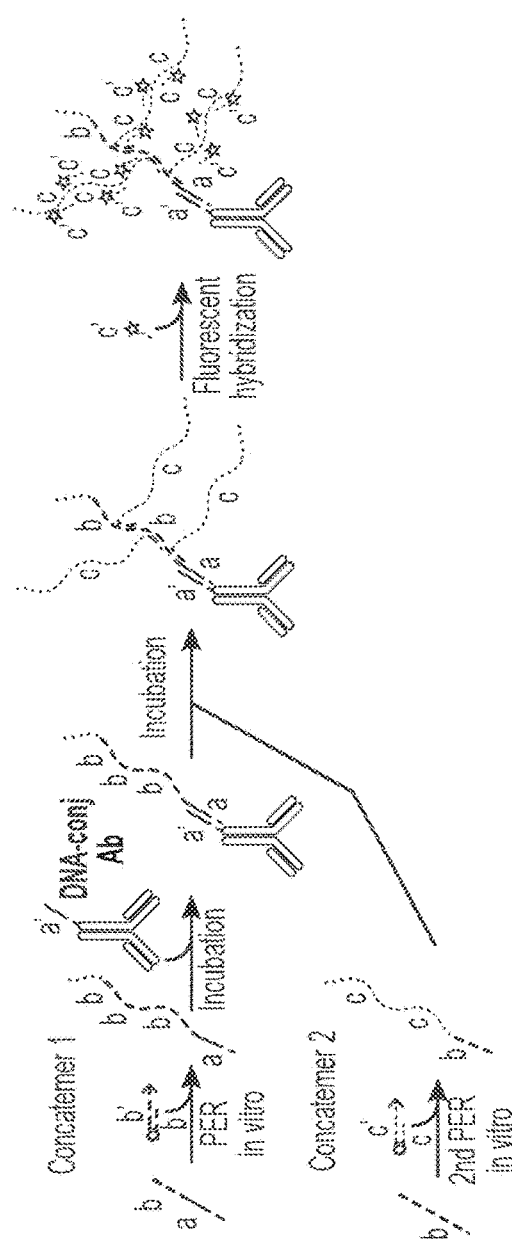
FIG. 22A: Pre-extension workflow for branching. Two sets of concatemers were pre-synthesized in solution, and applied onto the sample sequentially. The primer for the second concatemer was appended with a complementary sequence to the first concatemer.

Also provided herein are methods that results in the production for branched concatemers, which further amplify detection of the probes. The compositions produced using these methods are also provided. Further provided herein are kits for performing these methods. Examples of branch variants are provided in FIG. 17, FIG. 22A, and FIG. 22E. Branched structures may be produced, for example, by linking multiple copies of a first species of concatemer (all having the same sequence) to a second species of concatemer (having a sequence different from the first species), as depicted in FIGS. 17 and 22A in a branch-like pattern. Branched structures may also be produced, for example, by linking multiple different species of concatemer together in a branch-like pattern.

Thus, in some embodiments, multiplexed target detection methods comprise: (a) combining a sample containing a plurality of nucleic acid targets with a first plurality of probe strands, each probe strand of the first plurality comprising (i) an unpaired 5' target domain complementary to one of the nucleic acid targets and (ii) an unpaired 3' primer domain, and producing a reaction mixture comprising molecular targets bound to probe strands; (b) combining the reaction mixture produced in step (a) with dNTPs, strand-displacing polymerase, and a first plurality of catalytic molecules, each catalytic molecule of the first plurality comprising, 5' to 3', a first domain, a second domain, and a third domain wherein the first domain is bound to the second domain, and the third domain is an unpaired 3' toehold domain complementary to the unpaired 3' primer domain of one of the probe strands, and producing a reaction mixture comprising a first plurality of nucleic acid concatemers bound to molecular targets; (c) combining the reaction mixture produced in step (b) with a second plurality of probe strands, each probe strand of the second plurality comprising (i) an unpaired 5' domain complementary to a sequence of the concatemers and (ii) an unpaired 3' primer domain, and producing a reaction mixture comprising concatemers bound to probe strands; (d) combining the reaction mixture produced in step (c) with dNTPs, strand-displacing polymerase, and a second plurality of catalytic molecules, each catalytic molecule of the second plurality comprising, 5' to 3', a first domain, a second domain, and a third domain wherein the first domain is bound to the second domain, and the third domain is an unpaired 3' toehold domain complementary to the unpaired 3' primer domain of one of the probe strands of the second plurality of probe strands, and producing a reaction mixture comprising nucleic acid concatemers of the first plurality of nucleic acid concatemers bound to a second plurality of nucleic acid concatemers; (e) combining the reaction mixture produced in step (d) with a plurality of signal strands, each signal strand linked to a different detectable molecule and comprising a domain complementary to the unpaired 3' primer domain of one of the probe strands of the second plurality of probe strands, and producing concatemers labeled by a plurality of signal strands; and (f) optionally further comprising imaging the labeled concatemers. See, e.g., FIG. 17.

In some embodiments, multiplexed target detection methods comprise: (a) combining a sample containing a plurality of nucleic acid targets with a first plurality of probe strands, each probe strand of the first plurality comprising (i) an unpaired 5' target domain a complementary to one of the nucleic acid targets and (ii) an unpaired 3' primer domain b, and producing a reaction mixture comprising molecular targets bound to probe strands; (b) combining the reaction mixture produced in step (a) with dNTPs, strand-displacing polymerase, and a first plurality of catalytic molecules, each catalytic molecule of the first plurality comprising, 5' to 3', domain $a_1$, domain x, domain $a_2$, domain $b_1$, domain $b_1^*$, domain $a_2^*$, domain $x^*$, domain $a_1^*$, domain $b_2^*$, and domain $a_3^*$, wherein domain $a_1$, domain x, domain $a_2$, and domain $b_1$ respectively bind to (are complementary to) domain $b_1^*$, domain $a_2^*$, domain $x^*$, and domain $a_1^*$, and domains $b_2^*$ and domain $a_3^*$ form an unpaired 3' toehold domain complementary to the probe strand of the first plurality, and producing a reaction mixture comprising a first plurality of nucleic acid concatemers bound to molecular targets; (c) combining the reaction mixture produced in step (b) with a second plurality of probe strands, each probe strand of the second plurality comprising (i) an unpaired 5' domain $x^*$ complementary to domain x of the catalytic molecules and (ii) an unpaired 3' primer domain b complementary to domains b1 and $b_2^*$ of the catalytic molecules, and producing a reaction mixture comprising concatemers bound to probe strands; (d) combining the reaction mixture produced in step (c) with dNTPs, strand-displacing polymerase, and a second plurality of catalytic molecules, each catalytic molecule of the second plurality comprising, 5' to 3', domain $a_1$, domain x, domain $a_2$, domain $b_1$, domain $b_1^*$, domain $a_2^*$, domain $x^*$, domain $a_1^*$, domain $b_2^*$, and domain $a_3^*$, wherein domain $a_1$, domain x, domain $a_2$, and domain $b_1$ respectively bind to (are complementary to) domain $b_1^*$, domain $a_2^*$, domain $x^*$, and domain $a_1^*$, and domains $b_2^*$ and domain $a_3^*$ form an unpaired 3' toehold domain complementary to the probe strand of the first plurality, and producing branched concatemers. In some embodiments, the methods further comprise (e) combining the reaction mixture produced in step (d) with a plurality of signal strands, each signal strand linked to a different detectable molecule and comprising a domain complementary to the unpaired 3' primer domain b of the probe strands of the first and/or second plurality of probe strands, and producing concatemers labeled by a plurality of signal strands. In some embodiments, the methods further comprise imaging the labeled concatemers. See, e.g., FIGS. 22D and 22E.

In some embodiments, the catalytic molecules are comprised of DNA. In some embodiments, the catalytic molecules are comprised of RNA.

In some embodiments, the first domain of each catalytic molecule is bound to the second domain of the same catalytic molecule. In some embodiments, the first domain each catalytic molecule comprises a sequence wholly complementary to the second domain of the same catalytic molecule. In some embodiments, the second domain of each catalytic molecule comprises a sequence identical to the third domain of the same catalytic molecule.

In some embodiments, each catalytic molecule further comprises a stopper molecule or modification that terminates polymerization located between the first and second domains of the same catalytic molecule. For example, the molecule or modification that terminates polymerization may be selected from a triethylene glycol (TEG), 18-atom hexa-ethylene glycol, adenylation, azide, digoxigenin, cholesteryl-TEG, 3-cyanovinylcarbazole (CNVK), iso-dG and iso-dC. In some embodiments, the stopper molecule is guanine and the catalytic molecule is comprised of adenine, thymine and cytosine, or wherein the stopper molecule is cytosine and the catalytic molecule is comprised of adenine, thymine and guanine.

In some embodiments, each catalytic molecule is a catalytic hairpin molecule further comprising a loop domain located between the first and second domains. In some embodiments, each catalytic hairpin molecule is comprised of a single strand of DNA having a length of 25-300 nucleotides.

In some embodiments, the catalytic molecules are present in a reaction mixture at a concentration of 1 nM to 1 μM. Other concentrations are provided elsewhere herein.

In some embodiments, the probe strands are comprised of DNA. In some embodiments, the probe strands are comprised of RNA.

In some embodiments, each probe strand has a length of 10-50 nucleotides. In some embodiments, the target domain of each probe strand has a length of 5-25 nucleotides. In some embodiments, the primer domain of each probe strand has a length of 5-25 nucleotides. Other probe strand lengths and domain lengths are provided elsewhere herein.

In some embodiments, the composition comprises the probe strands at a concentration of 1 nM to 1 μM. Other concentrations are provided elsewhere herein.

In some embodiments, the nucleic acid target comprises DNA or RNA. For example, the nucleic acid target may be chromosomal DNA. In some embodiments, the nucleic acid target is mRNA or miRNA.

In some embodiments, the detectable molecule of the signal strands is a fluorophore. In some embodiments, each of the signal strands has a length of 10-30 nucleotides. Other signal strand lengths are provided elsewhere herein.

In some embodiments, a reaction mixture comprises signal strands at a concentration of 1 nM to 1 μM. Other concentrations are provided elsewhere herein.

In some embodiments, the strand-displacing polymerase is selected from phi29 DNA polymerases, Bst DNA polymerases, and Bsu DNA polymerase, large fragment.

In some embodiments, the reaction mixture of step (a) comprises aqueous buffer, optionally phosphate buffered saline (PBS).

In some embodiments, a reaction mixture comprises dNTPs at a concentration of 1-500 μM. In some embodiments, a reaction mixture comprises $MgSO_4$ at a concentration of 5-50 mM.

Imaging Variants

Multiplexing is achieved by designing several orthogonal PER extension reactions. By using different fluorophores on the complementary oligonucleotides to these strands, up to 3-4 targets can be imaged. Another possibility is to use fluorophore-labeled dNTPs during PER extension to barcode each extension reaction, either by using different fluorophores for each of sequentially grown probe strands or by relying on the differential fluorescent colors arising from the different sequences to map each fluorescent point color to a specific target.

Figure 7A:
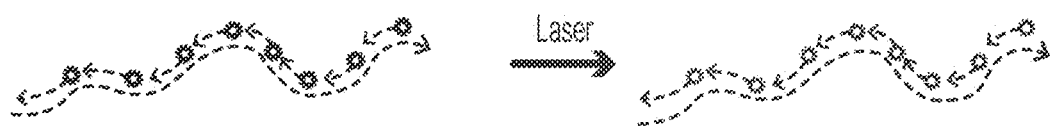
FIGS. 7A-7D: Strategies for multiplexing via signal destruction.
Figure 7B:
Figure 7C:
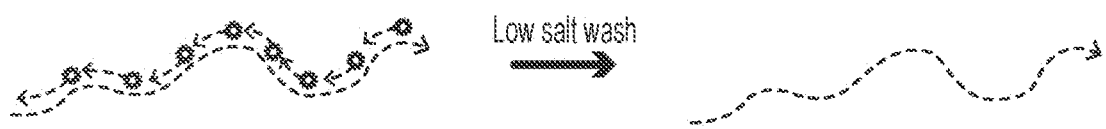
Figure 7D:
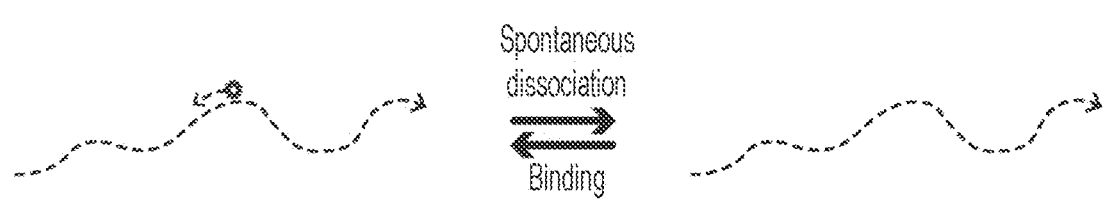

With the above approaches, spectral overlap of the fluorescence spectra limits the ability to multiplex target detection, but there are also several strategies that can be used to overcome this. In general, each of these strategies requires a way to activate a single target's fluorescence at a time, which also requires the ability to disable or destroy previously imaged targets. Several ways to achieve this are depicted in FIG. 7. One option is to bleach the fluorescent signal of each target once it has been imaged using a strong laser directed at the sample (FIG. 7A). If the fluorescent oligonucleotides are RNA, then they may be digested with an RNase (FIG. 7B). By designing the fluorescent oligonucleotides to be stably bound under high salt conditions but unstable under low salt conditions, individual fluorescent signals can be washed off of a target strand through a simple buffer exchange (FIG. 7C). Finally, the fluorescent oligonucleotides may be designed to be transiently bound to the PER-synthesized scaffolds. This strategy can be used to localize fluorescent signal for either diffraction-limited or super-resolution imaging.

Thus, in some embodiments, the methods comprise sequential imaging, whereby a first set of fluorophore-labeled signal strands are applied to a target or multiple targets, imaged, then removed (e.g., bleached, digested, washed away, or dissociated), and then a second set of fluorophore-labeled signal stands are applied to a different target or targets, imaged, and then removed, and so on with different sets of fluorophore-labeled signal strands specific for different targets.

Because all of these strategies allow individual targets to be imaged and then deactivated one at a time, they are all compatible with highly multiplexed imaging. In theory, an arbitrary number of targets could be imaged using as few as one laser if all the fluorescence is in the same channel. Not only does this overcome the challenge of different fluorophores' spectral overlap, but it could also mean a cheaper imaging setup as only one laser is required.

Imaging DNA, RNA, and proteins in their native conformation can help elucidate the structures and functions of these biomolecules that are foundational to life. Above, we introduced a new method for synthesizing long polymers for in situ amplification imaging and highlight some of the ways it can be used to image many targets in a single sample.

The present disclosure further encompasses the following numbered paragraphs:

1. A multiplexed target detection method, comprising:
(a) combining a sample containing a plurality of nucleic acid targets with a plurality of probe strands, each probe strand comprising (i) an unpaired 5' target domain complementary to one of the nucleic acid targets and (ii) an unpaired 3' primer domain, and producing a first reaction mixture comprising molecular targets bound to probe strands;
(b) combining the first reaction mixture produced in step (a) with dNTPs, strand-displacing polymerase, and a plurality of catalytic molecules, each catalytic molecule comprising, 5' to 3', a first domain, a second domain, and a third domain wherein the first domain is bound to the second domain, and the third domain is an unpaired 3' toehold domain complementary to the unpaired 3' primer domain of one of the probe strands, and producing a second reaction mixture comprising nucleic acid concatemers bound to molecular targets;
(c) combining the second reaction mixture produced in step (b) with a plurality of signal strands, each signal strand linked to a different detectable molecule and comprising a domain complementary to the unpaired 3' primer domain of one of the probe strands, and producing concatemers labeled by a plurality of signal strands; and
(d) optionally further comprising imaging the labeled concatemers.

1A. A multiplexed target detection method, comprising:
(a) combining a plurality of probe strands with dNTPs, strand-displacing polymerase, and a plurality of catalytic molecules, wherein each probe strand comprises (i) an unpaired 5' target domain complementary to a nucleic acid target of a plurality of nucleic acid targets and (ii) an unpaired 3' primer domain, and wherein each catalytic molecule comprises, 5' to 3', a first domain, a second domain, and a third domain wherein the first domain is bound to the second domain, and the third domain is an unpaired 3' toehold domain complementary to the unpaired 3' primer domain of one of the probe strands, and producing a first reaction mixture comprising nucleic acid concatemers bound to probe strands;
(b) combining the first reaction mixture produced in step (a) with a sample containing the plurality of nucleic acid targets and producing a second reaction mixture comprising nucleic acid concatemers bound to molecular targets;

(c) combining the second reaction mixture produced in step (b) with a plurality of signal strands, wherein each signal strand is linked to a different detectable molecule and comprises a domain complementary to the unpaired 3' primer domain of one of the probe strands, and producing concatemers labeled by a plurality of signal strands; and (d) optionally further comprising imaging the labeled concatemers.

2. The method of paragraph 1 or 1A, wherein the catalytic molecules are comprised of DNA.

3. The method of any one of paragraphs 1, 1A, or 2, wherein the catalytic molecules are comprised of RNA.

4. The method of any one of paragraphs 1-3, wherein the first domain of each catalytic molecule is bound to the second domain of the same catalytic molecule.

5. The method of any one of paragraphs 1-4, wherein the first domain each catalytic molecule comprises a sequence wholly complementary to the second domain of the same catalytic molecule.

6. The method of any one of paragraphs 1-5, wherein the second domain of each catalytic molecule comprises a sequence identical to the third domain of the same catalytic molecule.

7. The method of any one of paragraphs 1-6, wherein each catalytic molecule further comprises a stopper molecule or modification that terminates polymerization located between the first and second domains of the same catalytic molecule.

8. The method of paragraph 7, wherein the molecule or modification that terminates polymerization is selected from a triethylene glycol (TEG), 18-atom hexa-ethylene glycol, adenylation, azide, digoxigenin, cholesteryl-TEG, 3-cyanovinylcarbazole (CNVK), iso-dG and iso-dC.

9. The method of paragraph 7, wherein the stopper molecule is guanine and the catalytic molecule is comprised of adenine, thymine and cytosine, or wherein the stopper molecule is cytosine and the catalytic molecule is comprised of adenine, thymine and guanine.

10. The method of any one of paragraphs 1-9, wherein each catalytic molecule is a catalytic hairpin molecule further comprising a loop domain located between the first and second domains.

11. The method of paragraph 10, wherein each catalytic hairpin molecule is comprised of a single strand of DNA having a length of 25-300 nucleotides.

12. The method of any one of paragraphs 1-11, wherein the reaction mixture of step (b) comprises the catalytic molecules at a concentration of 1 nM to 1 µM.

13. The method of any one of paragraphs 1-12, wherein the probe strands are comprised of DNA.

14. The method of any one of paragraphs 1-13, wherein the probe strands are comprised of RNA.

15. The method of any one of paragraphs 1-14, wherein each probe strand has a length of 10-50 nucleotides.

16. The method of any one of paragraphs 1-15, wherein the target domain of each probe strand has a length of 5-25 nucleotides.

17. The method of any one of paragraphs 1-16, wherein the primer domain of each probe strand has a length of 5-25 nucleotides.

18. The method of any one of paragraphs 1-17, wherein the composition comprises the probe strands at a concentration of 1 nM to 1 µM.

19. The method of any one of paragraphs 1-18, wherein the nucleic acid target comprises DNA or RNA.

20. The method of paragraph 19, wherein the nucleic acid target is chromosomal DNA.

21. The method of paragraph 19, wherein the nucleic acid target is mRNA or miRNA.

22. The method of any one of paragraphs 1-22, wherein the detectable molecule of the signal strands is a fluorophore.

23. The method of any one of paragraphs 1-23, wherein each of the signal strands has a length of 10-30 nucleotides.

24. The method of any one of paragraphs 1-22, wherein the reaction mixture of (c) comprises the signal strands at a concentration of 1 nM to 1 µM.

25. The method of any one of paragraphs 1-24, wherein the strand-displacing polymerase is selected from phi29 DNA polymerases, Bst DNA polymerases, and Bsu DNA polymerase, large fragment.

26. The method of any one of paragraphs 1-25, wherein the reaction mixture of step (a) comprises aqueous buffer, optionally phosphate buffered saline (PBS).

27. The method of any one of paragraphs 1-26, wherein the reaction mixture of step (b) and/or step (a) comprises dNTPs at a concentration of 1-500 µM.

28. The method of any one of paragraphs 1-22, wherein the reaction mixture of step (b) and/or step (c) comprises MgSO4 at a concentration of 5-50 mM.

29. The method of any one of paragraphs 1-28, wherein:
the plurality of probe strands of step (a) comprises 2-10,000 probe strands;
the plurality of catalytic molecules of step (b) comprises 2-10,000 catalytic molecules; and
the plurality of signal strands of step (c) comprises 2-10,000 signal strands.

30. The method of any one of paragraphs 1-29, wherein the sample is a cell sample.

31. The method of any one of paragraphs 1-29, wherein the sample is a tissue sample.

32. The method of paragraph 31, wherein the tissue sample is a brain tissue sample.

33. The sample of paragraph 31, wherein the tissue sample is a tumor tissue sample.

34. A multiplexed target detection method, comprising:
(a) combining a sample containing a plurality of protein or peptide targets with a plurality of primary binding partners, each of which binds specifically to a protein or peptide target and is linked to a probe strand, and producing a first reaction mixture comprising protein or peptide bound to primary binding partners;

(b) combining the first reaction mixture produced in step (a) with dNTPs, strand-displacing polymerase, and a plurality of catalytic molecules, each catalytic molecule comprising, 5' to 3', a first domain, a second domain, and a third domain wherein the first domain is bound to the second domain, and the third domain is an unpaired 3' toehold domain complementary to the probe strand of one of the primary binding partners, and producing a second reaction mixture comprising nucleic acid concatemers bound to primary binding partners;

(c) combining the second reaction mixture produced in step (b) with a plurality of signal strands, each signal strand linked to a different detectable molecule and comprising a domain complementary to the bridge strand of one of the primary binding partners, and producing concatemers labeled by a plurality of signal strands; and (d) optionally further comprising imaging the labeled concatemers.

35. A multiplexed target detection method, comprising:
(a) combining a sample containing a plurality of protein or peptide targets with a plurality of primary binding partners, each of which binds specifically to a protein or peptide target and is linked to a bridge strand, and producing a first reaction mixture comprising protein or peptide bound to primary binding partners;

(b) combining the first reaction mixture with a plurality of probe strands, wherein each probe strand comprises (i) an unpaired 5' target domain complementary to the bridge strand of one of the primary binding partners and (ii) an unpaired 3' primer domain, and producing a second reaction mixture comprising primary binding partners bound to probe strands;

(c) combining the second reaction mixture with dNTPs, strand-displacing polymerase, and a plurality of catalytic molecules, wherein each catalytic molecule comprising, 5' to 3', a first domain, a second domain, and a third domain wherein the first domain is bound to the second domain, and the third domain is an unpaired 3' toehold domain complementary to one of the probe strands, and producing a third reaction mixture comprising nucleic acid concatemers bound to primary binding partners;

(d) combining the third reaction mixture produced in step (b) with a plurality of signal strands, each signal strand linked to a different detectable molecule and comprising a domain complementary to the bridge strand of one of the primary binding partners, and producing concatemers labeled by a plurality of signal strands; and (e) optionally further comprising imaging the labeled concatemers.

35A. A multiplexed target detection method, comprising:

(a) combining a sample containing a plurality of protein or peptide targets with a plurality of primary binding partners, each of which binds specifically to a protein or peptide target and is linked to a bridge strand, and producing a first reaction mixture comprising protein or peptide bound to primary binding partners;

(b) combining the first reaction mixture with concatemers bound to probe strands produced by combining in a second reaction mixture dNTPs, strand-displacing polymerase, a plurality of probe strands, and a plurality of catalytic molecules, wherein each probe strand comprises (i) an unpaired 5' target domain complementary to the bridge strand of one of the primary binding partners and (ii) an unpaired 3' primer domain, and wherein each catalytic molecule comprising, 5' to 3', a first domain, a second domain, and a third domain wherein the first domain is bound to the second domain, and the third domain is an unpaired 3' toehold domain complementary to one of the probe strands, and producing a third reaction mixture comprising nucleic acid concatemers bound to primary binding partners;

(c) combining the third reaction mixture produced in step (b) with a plurality of signal strands, each signal strand linked to a different detectable molecule and comprising a domain complementary to the bridge strand of one of the primary binding partners, and producing concatemers labeled by a plurality of signal strands; and (d) optionally further comprising imaging the labeled concatemers.

35B. A multiplexed target detection method, comprising:

(a) combining a plurality of primary binding partners with dNTPs, strand-displacing polymerase, and a plurality of catalytic molecules, wherein each binding partner binds specifically to a protein or peptide target and is linked to a probe strand, wherein each probe strand comprises (i) an unpaired 5' target domain complementary to the bridge strand of one of the primary binding partners and (ii) an unpaired 3' primer domain, and wherein each catalytic molecule comprising, 5' to 3', a first domain, a second domain, and a third domain wherein the first domain is bound to the second domain, and the third domain is an unpaired 3' toehold domain complementary to one of the probe strands, and producing a first reaction mixture comprising primary binding partners bound to nucleic acid concatemers (BP-concatemer complexes);

(b) combining the BP-concatemer complexes of the first reaction mixture with a sample containing a plurality of protein or peptide targets, and producing a second reaction mixture comprising protein or peptide bound to BP-concatemer complexes;

(c) combining the second reaction mixture produced in step (b) with a plurality of signal strands, each signal strand linked to a different detectable molecule and comprising a domain complementary to the probe strand of one of the primary binding partners, and producing concatemers labeled by a plurality of signal strands; and (d) optionally further comprising imaging the labeled concatemers.

36. A multiplexed target detection method, comprising:

(a) combining a sample containing a plurality of protein or peptide targets with a plurality of primary binding partners (e.g., primary antibodies), each of which binds specifically to a protein or peptide target, and producing a reaction mixture comprising protein or peptide bound to primary binding partners (e.g., primary antibodies);

(b) combining the reaction mixture produced in step (a) with a plurality of secondary binding partners (e.g., secondary antibodies), each of which binds specifically to a primary binding partner (e.g., primary antibody) and is linked to a bridge strand, and producing a reaction mixture comprising primary antibodies bound to secondary binding partners (e.g., secondary antibodies);

(c) combining the reaction mixture produced in step (b) with dNTPs, strand-displacing polymerase, and a plurality of catalytic molecules, each catalytic molecule comprising, 5' to 3', a first domain, a second domain, and a third domain wherein the first domain is bound to the second domain, and the third domain is an unpaired 3' toehold domain complementary to the bridge strand of one of the secondary binding partners (e.g., secondary antibodies), and producing a reaction mixture comprising nucleic acid concatemers bound to secondary binding partners (e.g., secondary antibodies);

(d) combining the reaction mixture produced in step (c) with a plurality of signal strands, each signal strand linked to a different detectable molecule and comprising a domain complementary to the bridge strand of one of the secondary binding partners (e.g., secondary antibodies), and producing concatemers labeled by a plurality of signal strands; and (e) optionally further comprising imaging the labeled concatemers.

37. A multiplexed target detection method, comprising:

(a) combining a sample containing a plurality of protein or peptide targets with a plurality of primary binding partners (e.g., primary antibodies), each of which binds specifically to a protein or peptide target, and producing a reaction mixture comprising protein or peptide bound to primary binding partners (e.g., primary antibodies);

(b) combining the reaction mixture produced in step (a) with a plurality of secondary antibodies, each of which binds specifically to a primary binding partner (e.g., primary antibody) and is linked to a bridge strand, and producing a reaction mixture comprising primary antibodies bound to secondary binding partners (e.g., secondary antibodies);

(c) combining the reaction mixture produced in step (b) with a plurality of probe strands, each probe strand comprising (i) an unpaired 5' target domain complementary to the of bridge strand of one of the secondary binding partners (e.g., secondary antibodies) and (ii) an unpaired 3' primer domain, and producing a reaction mixture comprising probe strands bound to secondary binding partners (e.g., secondary antibodies);

(d) combining the reaction mixture produced in step (c) with dNTPs, strand-displacing polymerase, and a plurality of catalytic molecules, each catalytic molecule comprising, 5' to 3', a first domain, a second domain, and a third domain wherein the first domain is bound to the second domain, and the third domain is an unpaired 3' toehold domain complementary to the unpaired 3' primer domain of one of the probe strands, and producing a reaction mixture comprising nucleic acid concatemers bound to secondary binding partners (e.g., secondary antibodies);

(e) combining the reaction mixture produced in step (d) with a plurality of signal strands, each signal strand linked to a different detectable molecule and comprising a domain complementary to the unpaired 3' primer domain of one of the probe strands, and producing concatemers labeled by a plurality of signal strands; and (f) optionally further comprising imaging the labeled concatemers.

37A. A multiplexed target detection method comprising:

(a) combining a sample containing a plurality of nucleic acid targets with a first plurality of probe strands, each probe strand of the first plurality comprising (i) an unpaired 5' target domain a complementary to one of the nucleic acid targets and (ii) an unpaired 3' primer domain b, and producing a reaction mixture comprising molecular targets bound to probe strands;

(b) combining the reaction mixture produced in step (a) with dNTPs, strand-displacing polymerase, and a first plurality of catalytic molecules, each catalytic molecule of the first plurality comprising, 5' to 3', domain $a_1$, domain x, domain $a_2$, domain $b_1$, domain $b_1^*$, domain $a_2^*$, domain $x^*$, domain $a_1^*$, domain $b_2^*$, and domain $a_3^*$, wherein domain $a_1$, domain x, domain $a_2$, and domain $b_1$ respectively bind to domain $b_1^*$, domain $a_2^*$, domain $x^*$, and domain $a_1^*$, and domains $b_2^*$ and domain $a_3^*$ form an unpaired 3' toehold domain complementary to the probe strand of the first plurality, and producing a reaction mixture comprising a first plurality of nucleic acid concatemers bound to molecular targets;

(c) combining the reaction mixture produced in step (b) with a second plurality of probe strands, each probe strand of the second plurality comprising (i) an unpaired 5' domain $x^*$ complementary to domain x of the catalytic molecules and (ii) an unpaired 3' primer domain b complementary to domains b1 and $b_2^*$ of the catalytic molecules, and producing a reaction mixture comprising concatemers bound to probe strands; and (d) combining the reaction mixture produced in step (c) with dNTPs, strand-displacing polymerase, and a second plurality of catalytic molecules, each catalytic molecule of the second plurality comprising, 5' to 3', domain $a_1$, domain x, domain $a_2$, domain $b_1$, domain $b_1^*$, domain $a_2^*$, domain $x^*$, domain $a_1^*$, domain $b_2^*$, and domain $a_3^*$, wherein domain $a_1$, domain x, domain $a_2$, and domain $b_1$ respectively bind to domain $b_1^*$, domain $a_2^*$, domain $x^*$, and domain $a_1^*$, and domains $b_2^*$ and domain $a_3^*$ form an unpaired 3' toehold domain complementary to the probe strand of the first plurality, and producing branched concatemers.

37B. The method of claim 32, further comprising (e) combining the reaction mixture produced in step (d) with a plurality of signal strands, each signal strand linked to a different detectable molecule and comprising a domain complementary to the unpaired 3' primer domain b of the probe strands of the first and/or second plurality of probe strands, and producing concatemers labeled by a plurality of signal strands, and optionally further comprising imaging the labeled concatemers.

38. The method of any one of paragraphs 34-37B, wherein the catalytic molecules are comprised of DNA.

39. The method any one of paragraphs 34-37B, wherein the catalytic molecules are comprised of RNA.

40. The method any one of paragraphs 34-39, wherein the first domain of each catalytic molecule is bound to the second domain of the same catalytic molecule.

41. The method of any one of paragraphs 34-40, wherein the first domain each catalytic molecule comprises a sequence wholly complementary to the second domain of the same catalytic molecule.

42. The method of any one of paragraphs 34-41, wherein the second domain of each catalytic molecule comprises a sequence identical to the third domain of the same catalytic molecule.

43. The method of any one of paragraphs 34-42, wherein each catalytic molecule further comprises a stopper molecule or modification that terminates polymerization located between the first and second domains of the same catalytic molecule.

44. The method of paragraph 43, wherein the molecule or modification that terminates polymerization is selected from a triethylene glycol (TEG), 18-atom hexa-ethylene glycol, adenylation, azide, digoxigenin, cholesteryl-TEG, 3-cyanovinylcarbazole (CNVK), iso-dG and iso-dC.

45. The method of paragraph 43, wherein the stopper molecule is guanine and the catalytic molecule is comprised of adenine, thymine and cytosine, or wherein the stopper molecule is cytosine and the catalytic molecule is comprised of adenine, thymine and guanine.

46. The method of any one of paragraphs 34-45, wherein each catalytic molecule is a catalytic hairpin molecule further comprising a loop domain located between the first and second domains.

47. The method of paragraph 46, wherein each catalytic hairpin molecule is comprised of a single strand of DNA having a length of 25-300 nucleotides.

48. The method of any one of paragraphs 34-47, wherein the reaction mixture comprising catalytic molecules comprises the catalytic molecules at a concentration of 1 nM to 1 μM.

49. The method of any one of paragraphs 34-48, wherein the probe strands are comprised of DNA.

50. The method of any one of paragraphs 34-49, wherein the probe strands are comprised of RNA.

51. The method of any one of paragraphs 34-50, wherein each probe strand has a length of 10-50 nucleotides.

52. The method of any one of paragraphs 34-51, wherein the target domain of each probe strand has a length of 5-25 nucleotides.

53. The method of any one of paragraphs 34-52, wherein the primer domain of each probe strand has a length of 5-25 nucleotides.

54. The method of any one of paragraphs 34-53, wherein the composition comprises the probe strands at a concentration of 1 nM to 1 μM.

55. The method of any one of paragraphs 34-54, wherein the protein or peptide targets are selected from antibodies, cytokines and growth factors.
56. The method of any one of paragraphs 34-55, wherein the detectable molecule of the signal strands is a fluorophore.
57. The method of any one of paragraphs 34-56, wherein each of the signal strands has a length of 10-30 nucleotides.
58. The method of any one of paragraphs 34-57, wherein the reaction mixture comprising signal strands comprises the signal strands at a concentration of 1 nM to 1 µM.
59. The method of any one of paragraphs 34-58, wherein the strand-displacing polymerase is selected from phi29 DNA polymerases, Bst DNA polymerases, and Bsu DNA polymerase, large fragment.
60. The method of any one of paragraphs 34-59, wherein the reaction mixtures comprise aqueous buffer, optionally phosphate buffered saline (PBS).
61. The method of any one of paragraphs 34-60, wherein the reaction mixture comprising dNTPs comprises dNTPs at a concentration of 1-500 µM.
62. The method of any one of paragraphs 34-61, wherein the reaction mixtures comprises MgSO4 at a concentration of 5-50 mM.
63. The method of any one of paragraphs 34-62, wherein:
the plurality of primary and/or secondary binding partners comprises 2-10,000 primary and/or secondary binding partners;
the plurality of probe strands comprises 2-10,000 probe strands;
the plurality of catalytic molecules comprises 2-10,000 catalytic molecules; and/or
the plurality of signal strands comprises 2-10,000 signal strands.
64. The method of any one of paragraphs 34-63, wherein the sample is a cell sample, bodily fluid sample, or fecal sample.
65. The method of any one of paragraphs 34-64, wherein the sample is a tissue sample.
66. The method of paragraph 64, wherein the tissue sample is a brain tissue sample.
67. The sample of paragraph 64, wherein the tissue sample is a tumor sample.
68. The sample of paragraph 64, wherein the bodily fluid sample is a serum, blood, or saliva sample.
68. A multiplexed target detection method, comprising:
(a) combining a sample containing a plurality of nucleic acid targets with a first plurality of probe strands, each probe strand of the first plurality comprising (i) an unpaired 5' target domain complementary to one of the nucleic acid targets and (ii) an unpaired 3' primer domain, and producing a reaction mixture comprising molecular targets bound to probe strands;
(b) combining the reaction mixture produced in step (a) with dNTPs, strand-displacing polymerase, and a first plurality of catalytic molecules, each catalytic molecule of the first plurality comprising, 5' to 3', a first domain, a second domain, and a third domain wherein the first domain is bound to the second domain, and the third domain is an unpaired 3' toehold domain complementary to the unpaired 3' primer domain of one of the probe strands, and producing a reaction mixture comprising a first plurality of nucleic acid concatemers bound to molecular targets;
(c) combining the reaction mixture produced in step (b) with a second plurality of probe strands, each probe strand of the second plurality comprising (i) an unpaired 5' domain complementary to a sequence of the concatemers and (ii) an unpaired 3' primer domain, and producing a reaction mixture comprising concatemers bound to probe strands;
(d) combining the reaction mixture produced in step (c) with dNTPs, strand-displacing polymerase, and a second plurality of catalytic molecules, each catalytic molecule of the second plurality comprising, 5' to 3', a first domain, a second domain, and a third domain wherein the first domain is bound to the second domain, and the third domain is an unpaired 3' toehold domain complementary to the unpaired 3' primer domain of one of the probe strands of the second plurality of probe strands, and producing a reaction mixture comprising nucleic acid concatemers of the first plurality of nucleic acid concatemers bound to a second plurality of nucleic acid concatemers;
(e) combining the reaction mixture produced in step (d) with a plurality of signal strands, each signal strand linked to a different detectable molecule and comprising a domain complementary to the unpaired 3' primer domain of one of the probe strands of the second plurality of probe strands, and producing concatemers labeled by a plurality of signal strands; and
(f) optionally further comprising imaging the labeled concatemers.
69. A composition, comprising:
(a) a catalytic molecule comprising, 5' to 3', a first domain, a second domain, and a third domain, wherein the first domain binds to the second domain, and the third domain is an unpaired 3' toehold domain;
(b) a probe strand comprising (i) an unpaired 5' target domain that binds specifically to a molecular target and (ii) an unpaired 3' primer domain that binds to the unpaired 3' toehold domain of the catalytic molecule; and
(c) an optional signal strand linked to a detectable molecule and comprising a domain that binds to the unpaired 3' primer domain of the probe strands.
70. The composition of paragraph 69, wherein the catalytic molecule is comprised of DNA.
71. The composition of paragraph 69 or 70, wherein the catalytic molecule is comprised of RNA.
72. The composition of paragraph 69, wherein the first domain of the catalytic molecule is bound to the second domain of the catalytic molecule.
73. The composition of any one of paragraphs 69-72, wherein the first domain of the catalytic molecule comprises a sequence wholly complementary to the second domain of the catalytic molecule.
74. The composition of any one of paragraphs 69-73, wherein the second domain of the catalytic molecule comprises a sequence identical to the third domain of the catalytic molecule.
75. The composition of any one of paragraphs 69-74, wherein the catalytic molecule further comprises a stopper molecule or modification that terminates polymerization located between the first and second domains.
76. The composition of paragraph 75, wherein the molecule or modification that terminates polymerization is selected from a triethylene glycol (TEG), 18-atom hexa-ethylene glycol, adenylation, azide, digoxigenin, cholesteryl-TEG, 3-cyanovinylcarbazole (CNVK), iso-dG and iso-dC.
77. The composition of paragraph 75, wherein the stopper molecule is guanine and the catalytic molecule is comprised of adenine, thymine and cytosine, or wherein the stopper molecule is cytosine and the catalytic molecule is comprised of adenine, thymine and guanine.
78. The composition of any one of paragraphs 69-77, wherein the catalytic molecule is a catalytic hairpin molecule further comprising a loop domain located between the first and second domains.
79. The composition of paragraph 78, wherein the catalytic hairpin molecule is comprised of a single strand of DNA having a length of 25-300 nucleotides.
80. The composition of any one of paragraphs 69-79, wherein the composition comprises the catalytic molecule at a concentration of 1 nM to 1 µM.
81. The composition of any one of paragraphs 69-80, wherein the probe strand is comprised of DNA.
82. The composition of any one of paragraphs 69-81, wherein the probe strand is comprised of RNA.
83. The composition of any one of paragraphs 69-82, wherein the probe strand has a length of 10-50 nucleotides.
84. The composition of any one of paragraphs 69-83, wherein the target domain of the probe strand has a length of 5-25 nucleotides.
85. The composition of any one of paragraphs 69-84, wherein the primer domain of the probe strand has a length of 5-25 nucleotides.
86. The composition of any one of paragraphs 69-85, wherein the composition comprises the probe strand at a concentration of 1 nM to 1 µM.
87. The composition of any one of paragraphs 69-86, wherein the molecular target is a nucleic acid target.
88. The composition of paragraph 87, wherein the target domain of the probe strand includes a nucleotide sequence complementary to the nucleic acid target.
89. The composition of paragraph 87 or 88, wherein the nucleic acid comprises DNA or RNA.
90. The composition of paragraph 89, wherein the nucleic acid is chromosomal DNA.
91. The composition of paragraph 89, wherein the nucleic acid is mRNA or miRNA.
92. The composition of any one of paragraphs 69-86, wherein the molecular target is a protein or peptide bound by a primary binding partner (e.g., an antibody) conjugated to a bridge strand.
93. The composition of paragraph 67, wherein the target domain of the probe strand includes a nucleotide sequence complementary to the bridge strand.
94. The composition of paragraph 92 or 93, wherein the protein is selected from antibodies, cytokines, and growth factors.
95. The composition of any one of paragraphs 69-94, wherein the detectable molecule of the signal strand is a fluorophore.
96. The composition of any one of paragraphs 69-95, wherein the signal strand has a length of 10-30 nucleotides.
97. The composition of any one of paragraphs 69-96, wherein the composition comprises the signal strand at a concentration of 1 nM to 1 µM.
98. The composition of any one of paragraphs 69-97 further comprising a strand-displacing polymerase.
99. The composition of paragraph 98, wherein the strand-displacing polymerase is selected from phi29 DNA polymerases, Bst DNA polymerases, and Bsu DNA polymerase, large fragment.
100. The composition of any one of paragraphs 69-99 further comprising a buffer, dNTPs and/or MgSO4.
101. The composition of paragraph 100, wherein the composition comprises phosphate buffered saline (PBS).
102. The composition of paragraph 100 or 101, wherein the composition comprises dNTP at a concentration of 1-500 µM.
103. The composition of any one of paragraphs 100-102, wherein the composition comprises MgSO4 at a concentration of 5-50 mM.
104. A composition, comprising:
(a) a plurality of catalytic molecules, each catalytic molecule comprising, 5' to 3', a first domain, a second domain, and a third domain, wherein the first domain binds to the second domain, and the third domain is an unpaired 3' toehold domain;
(b) a plurality of probe strands, each probe strand comprising (i) an unpaired 5' target domain that binds specifically to a molecular target and (ii) an unpaired 3' primer domain that binds to the unpaired 3' toehold domain of one of the catalytic molecules; and
(c) an optional plurality of signal strands, each signal strand linked to a different detectable molecule and comprising a domain that binds to the unpaired 3' primer domain of one of the probe strands.
105. The composition of paragraph 104, wherein:
the plurality of (a) comprises 2-10,000 of the catalytic molecules;
the plurality of (b) comprises 2-10,000 of the probe strands; and
the plurality of (c) comprises 2-10,000 of the signal strands.
106. A sample comprising a nucleic acid target to which a concatemer of tandem repeat sequence is bound, wherein a signal strand linked to a detectable label is bound to each sequence of the concatemer.
107. A sample comprising a protein target to which a primary binding partner (e.g., an antibody) is bound, wherein the primary binding partner (e.g., antibody) is linked to a concatemer of tandem repeat sequence, and a signal strand linked to a detectable label is bound to each sequence of the concatemer.
108. A sample comprising a protein target to which a primary binding partner (e.g., primary antibody) is bound, wherein a secondary binding partner (e.g., secondary antibody) is bound to the primary binding partner (e.g., primary antibody), the secondary binding partner (e.g., secondary antibody) is linked to a concatemer of tandem repeat sequence, and a signal strand linked to a detectable label is bound to each sequence of the concatemer.
109. The sample of any one of paragraphs 106-108, wherein the sample is a cell sample.
110. The sample of any one of paragraphs 106-108, wherein the sample is a tissue sample.
111. The sample of paragraph 110, wherein the tissue sample is a brain tissue sample.
112. The sample of paragraph 111, wherein the tissue sample is a tumor tissue sample.
113. A multiplexed target detection method comprising:
(a) combining a sample containing a plurality of nucleic acid targets with a first plurality of probe strands, each probe strand of the first plurality comprising (i) an unpaired 5' target domain a complementary to one of the nucleic acid targets and (ii) an unpaired 3' primer domain b, and producing a reaction mixture comprising molecular targets bound to probe strands;
(b) combining the reaction mixture produced in step (a) with dNTPs, strand-displacing polymerase, and a first plurality of catalytic molecules, each catalytic molecule of the first plurality comprising, 5' to 3', domain a1, domain x, domain a2, domain b1, domain b1*, domain a2*, domain x*, domain a1*, domain b2*, and domain a3*, wherein domain a1, domain x, domain a2, and domain b1 respectively bind to domain b1*, domain a2*, domain x*, and domain a1*, and domains b2* and domain a3* form an unpaired 3' toehold domain complementary to the probe strand of the first plurality, and producing a reaction mixture comprising a first plurality of nucleic acid concatemers bound to molecular targets;

(c) combining the reaction mixture produced in step (b) with a second plurality of probe strands, each probe strand of the second plurality comprising (i) an unpaired 5' domain x* complementary to domain x of the catalytic molecules and (ii) an unpaired 3' primer domain b complementary to domains b1 and b2* of the catalytic molecules, and producing a reaction mixture comprising concatemers bound to probe strands; and (d) combining the reaction mixture produced in step (c) with dNTPs, strand-displacing polymerase, and a second plurality of catalytic molecules, each catalytic molecule of the second plurality comprising, 5' to 3', domain a1, domain x, domain a2, domain b1, domain b1*, domain a2*, domain x*, domain a1*, domain b2*, and domain a3*, wherein domain a1, domain x, domain a2, and domain b1 respectively bind to domain b1*, domain a2*, domain x*, and domain a1*, and domains b2* and domain a3* form an unpaired 3' toehold domain complementary to the probe strand of the first plurality, and producing branched concatemers.

113. The method of paragraph 112, further comprising (e) combining the reaction mixture produced in step (d) with a plurality of signal strands, each signal strand linked to a different detectable molecule and comprising a domain complementary to the unpaired 3' primer domain b of the probe strands of the first and/or second plurality of probe strands, and producing concatemers labeled by a plurality of signal strands.

114. The method of paragraph 113, further comprising imaging the labeled concatemers.

EXAMPLES

Example 1

Example Workflow of Exchange Imaging Reaction

Figure 8:
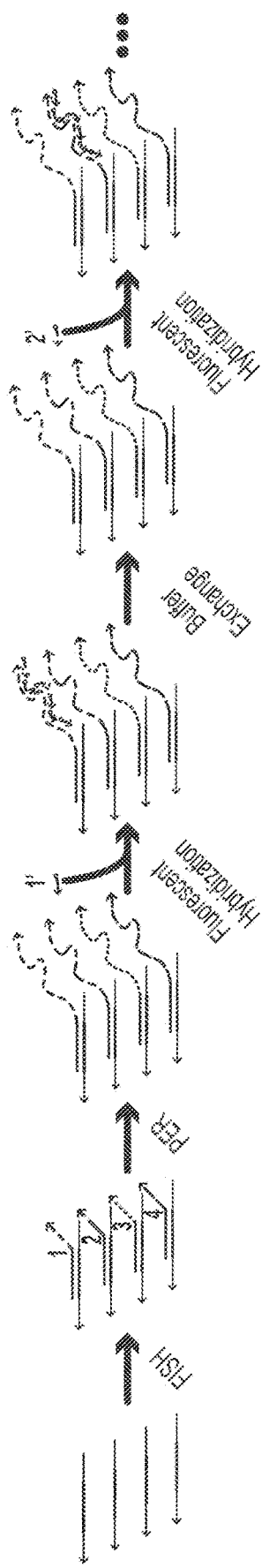
FIG. 8: Workflow for exchange imaging. Imaging multiple targets with a single laser can be achieved by alternating washing (buffer exchange) and fluorescent hybridization steps.

An example workflow of the exchange imaging strategy described in FIG. 7C is depicted in FIG. 8. Four targets are bound to four probes with different primer extension overhangs (domains 1-4). A fluorescent strand complementary to one target is hybridized and then imaged at a time, before a buffer exchange with low salt conditions is used to displace the fluorescent strand from its target.

In some instances, multiple PER hairpins are used per target to grow repetitive barcoded sequences, or to grow repetitive domains that are split across multiple hairpin synthesis steps. In some embodiments, the fluorescent oligonucleotides may be smaller in length than the repeated domain on the PER-synthesized scaffold. In some embodiments, these fluorescent oligonucleotides may be complementary to one or more of the repeated domain sequences.

Example 2

Single Primer Exchange Reaction

In this primer exchange reaction, primer binding domains having a length of 8-9 nucleotides were used to enable effective priming for extension and efficient spontaneous dissociation in last step at 37° C. A basic single primer exchange reaction was validated and characterized by incubating variable concentrations of hairpins (1 nM to 1 μM) together with 100 nM fluorophore-labeled primers with Bst Large Fragment polymerase and a mixture of nucleotides dATP, dTTP, and dCTP. The extended primer (concatemer) was visualized by gel electrophoresis (FIG. 9B). The length of the output constitutes a direct measure for evaluation of signal amplification level.

Example 3

Multiplexed Primer Exchange Reaction

Spectral multiplexing is used to establish the suitability of primer exchange reactions for simultaneous signal amplification on multiple targets. Four orthogonal primers, each labeled with a spectrally-distinct fluorophore are used, and all the extensions are run in parallel. Primers are designed to have low probabilities of binding either to themselves or to the primer binding sites on non-cognate hairpins at the operating temperature of 37° C. All primers feature the same sequence length (e.g., 9-nt) for cognate hairpin binding and have similar binding energies. All primers comprise sequences composed of three letters A, T, and C. These reaction parameters enable greater than 100-fold amplification and 4× spectral amplification.

Example 4

In Vitro PER-Based Signal Amplification

Figure 14A:
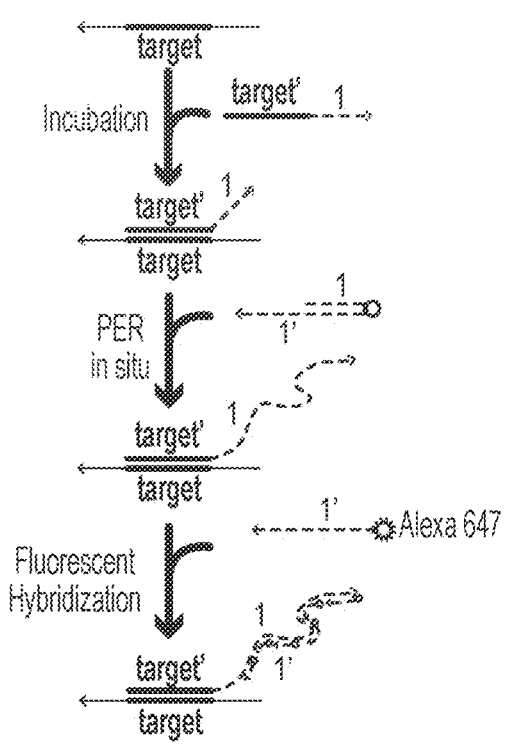
FIGS. 14A-14B: In situ vs. in vitro approaches.
Figure 14B:
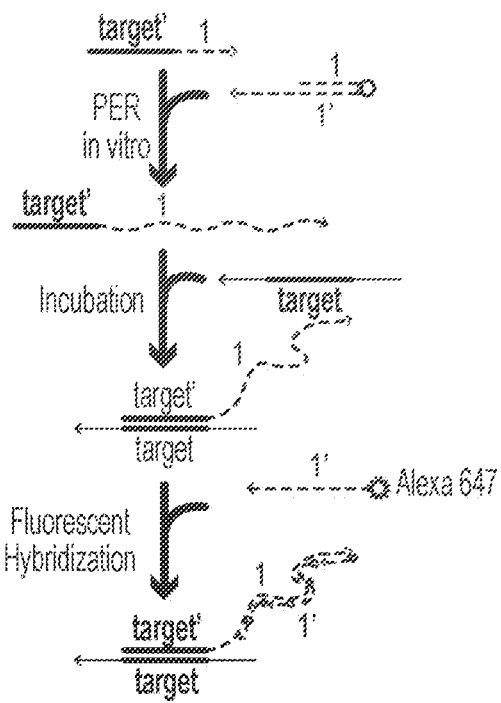

Experiments were carried out to examine amplification using in vitro-extended oligonucleotides. Instead of extending the oligonucleotides in situ, as described above, oligonucleotides were pre-extended in vitro. The overall scheme is illustrated in FIGS. 14A-14B.

PER was performed in vitro using a primer appended to a fluorescence in situ hybridization (FISH) probes. Then, the PER concatemer was used to label genomic target sites with DNA-FISH. The visualization was performed by hybridization of fluorescent signal strand to the concatemer. In these experiments, genomic repeat regions (such as major and minor satellite repeats in mouse cells or telomeres in human cells) were successfully visualized as robust test targets (FIG. 11A). Non-repeat regions were also targeted, which are hard to detect in absence of signal amplification. The primers appended on FISH probes (a mixture of 48 oligos that cover the target genomic region) were extended with in vitro PER and used for in situ labeling of a genomic sequence, XIST DNA, an only 2.7 kb long single-copy region on the X-chromosome of mouse embryonic fibroblasts (MEF) (FIG. 11B). Using stably-binding imagers (single-stranded nucleic acids linked to a fluorophore) of 20-nt length, the expected signal amplification for both assays 75-fold according to the gel results (FIG. 11C). Motivated by the high SNR obtained in these preliminary experiments, the compatibility of this approach was also validated with IF. For this purpose, the primers were appended with a 28-nt bridge sequence and PER was performed in vitro. The reaction mixture was then incubated with IF samples that were labeled secondary Ab conjugated to a sequence complementary to the bridge (FIG. 12A). The data targeting microtubules in mammalian cells demonstrates that PER offers higher signal in comparison to the secondary antibody staining alone with the same fluorophore (FIG. 12B).

Example 5

In Situ PER-Based Signal Amplification

The experiments with in vitro extended strands demonstrate signal amplification by PER for cell samples. Here, PER signal amplification is used to enhance sensitivity of IF in situ. The PER primer is presented on an antibody (Ab) through DNA-antibody conjugation. After labeling with the probes, the samples re incubated with PER components at 37° C., and the extended concatemer is visualized by hybridization of complementary fluorescent signal strands (FIG. 10B). Target proteins include those that mark cellular organelles with clear boundaries such as nucleoli, mitochondria or Golgi. In some experiments, an additional sequence domain is included on the antibody to image the same target with the same signal strand before and after extension, for precise quantification of SNR and fold-amplification.

To demonstrate in situ PER, experiments on FISH and IF samples were performed by respectively using FISH probes or secondary Ab carrying a primer sequence. With these experiments, the dependence of the amplification level and SNR on the hairpin concentration and absence of unspecific background were verified.

Figure 16:
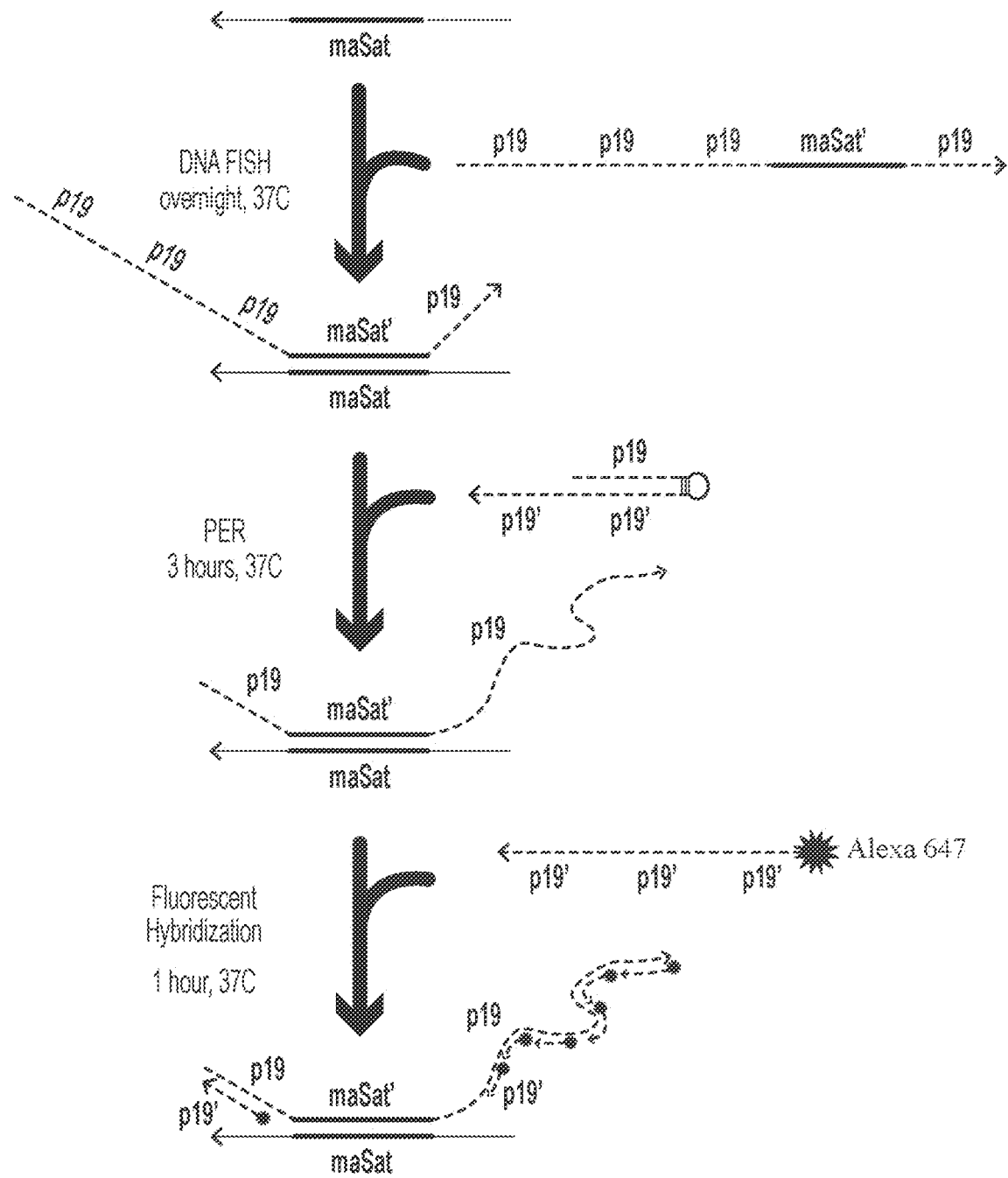
FIG. 16: Amplification strategy for rough amplification visualization. The major satellite probe contains a binding region for the Alexa 647-labeled p19' p19' p19' strand, so that fluorescence from samples with unamplified probes (without hairpins during PER incubation) can be compared to samples with amplified probes (with hairpins during PER incubation).

Major satellite repeat regions in MEF cells were targeted with FISH probes that carry a fluorophore on 5' end, and the PER primer sequence on the 3' (FIG. 16). Increasing levels of fluorescence were achieved by increasing the hairpin concentration. In the control condition without hairpin, PER did not take place and only the fluorescence coming from the probe itself was detected. Increasing levels of fluorescence were achieved by increasing the hairpin concentration from 500 nM to 1 μM (data not shown).

MEF cells were labeled with primary antibody targeting β-tubulin, followed by incubation with secondary antibodies either conjugated to Alexa488 fluorophore, or to PER primers. PER conditions were visualized by hybridization of Alexa647-conjugated signal strands (data now shown).

Example 6

In Situ PER-Based Signal Amplification

To be able to image thicker tissue sections without potential problems in diffusion and accessibility of DNA concatemers, in situ PER approach for tissue samples is established. Major challenges in tissues are the efficiency of PER in the tissue environment, the diffusion of PER components into the tissue and increased autofluorescence and unspecific background associated with PER and hybridizations. Whole-mount preparations of C. elegans were labeled with primer appended FISH probes targeting chromosome 2, and in situ extension by PER was applied. FISH was performed against chromosome 2 with probes carrying the primer site. In situ PER was followed by washing, hybridization of imagers and confocal imaging (data not shown).

Under these conditions, bright fluorescence signal throughout the full volume of the worms was observed (data not shown). For these experiments, the bridge sequences on the probes contain an additional stretch of unextended primer sequence. Using the same signal strand, the signal without any amplification is first imaged to establish a basal level. Then we the extended PER strands of known length are hybridized, and the same site is imaged with the same signal strand to quantify the signal after amplification. This strategy is used to adjust the hybridization efficiency (by varying signal strand length), diffusivity (by varying hybridization duration), binding stability (by varying wash conditions) and non-specificity (by varying blockers and hybridization temperature) of signal strands in tissue samples. Targets are labeled on <15 μm sections of human brain.

Further, the in vitro method was used to examine murine retinal tissue using RNA FISH. Signal was detected in the tissue sample (data not shown).

Example 7

Spectral Multiplexing In Vitro

Four orthogonal sequences are used in combination with IF to obtain simultaneous multiplexing using plate assays. In vitro extension and in situ detection strategies are used to verify orthogonality of detection in situ. Simultaneous in situ extensions are performed using four orthogonal primer sequences and the orthogonality of the in situ reaction is verified. Morphologically distinct cellular compartments and structures (such as nucleoli, mitochondria, Golgi, microtubules) are targeted by IF with orthogonally labeled Abs and negative controls are used, where each primary Ab is omitted.

Experiments of in situ orthogonality successfully demonstrated 2-color FISH labeling targeting major and minor satellite repeats appended with orthogonal primers that were extended in situ. FISH was performed against major and minor satellite repeats in MEF. FISH probes were extended in situ simultaneously and hybridized with orthogonal imagers carrying Alexa647 (minor) or Alexa565 (major) (data not shown).

Example 8

Immunostaining Experiments

Figure 13:
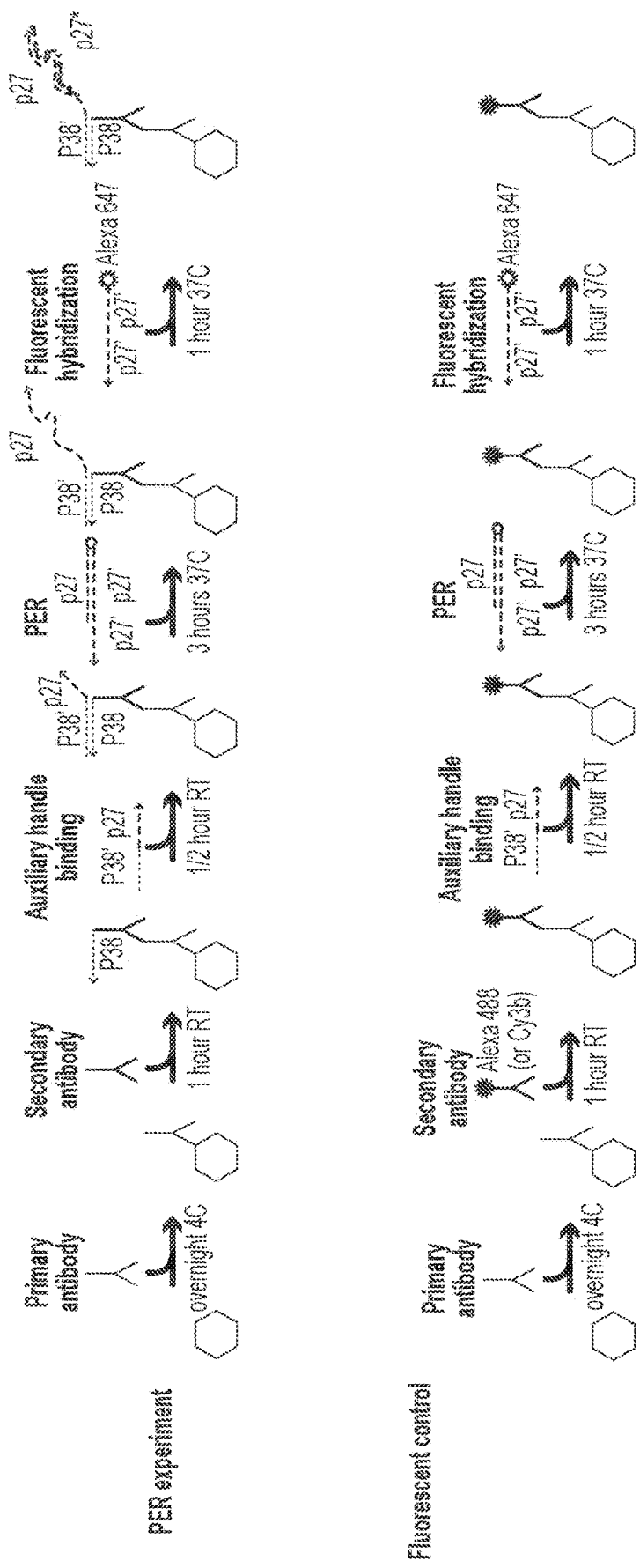
FIG. 13: IF strategy with conjugated secondary antibody. For the main amplification experiment, a primary antibody is first bound to its target and then a DNA-conjugated secondary antibody is bound to the primary antibody. A strand complementary to the conjugated P38 region was then bound with a projected p27 handle. PER amplification was performed on the p27 handle and visualized using complementary fluorescent 647 strands. The fluorescent control uses a fluorescent secondary antibody rather than a conjugated one.

Initial immunostaining experiments using PER amplification were performed using a secondary antibody with a DNA strand conjugated (FIG. 13). This "bridge" sequence, in this case P38, was used as a handle to bind a strand with the p27 primer handle projected. This handle was then extended with repeats of p27, to which fluorescent 647 strands were bound to visualize the signal. In the fluorescent control experiment, a fluorescent 488 secondary antibody was bound to the primary antibody, rather than the DNA-conjugated secondary.

Results from an example using a primary antibody targeting Beta-tubulin can be seen in FIG. 10. The top row shows the fluorescent secondary antibody (Alexa 488-labeled) signal in the 488 channel, and the bottom row shows the PER signal, which only shows a signal in the 647 channel, as expected.

Example 9

Quantification of the Signal Amplification Level

Figure 21A:
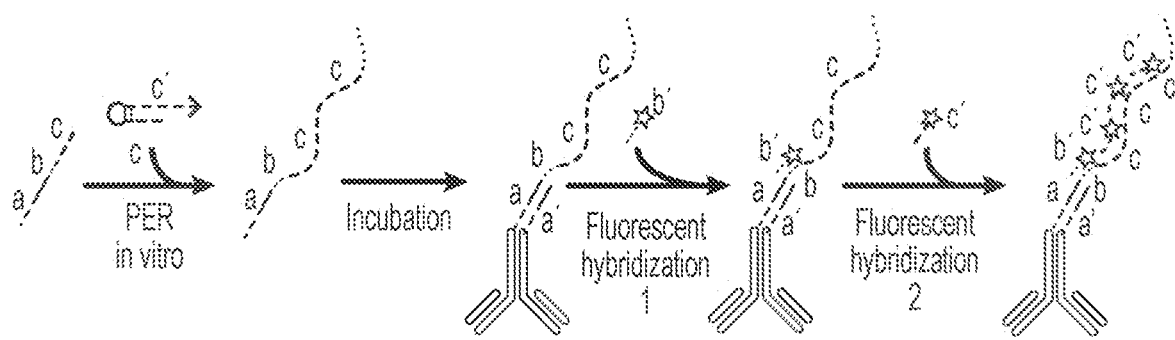
FIG. 21A: Workflow schematic of signal amplification. Images were acquired before and after 'fluorescent hybridization 2' to quantify the signal level change.

The quantification of the actual in situ signal amplification level was demonstrated through a comparison of the signal level before and after amplification in the same sample. This was achieved by including an extra binding site (P28) for an orthogonal fluorescent oligonucleotide in between the bridge complement sequence (B38*) and P27 primer sequence in the handle (FIG. 21A).

Figure 21B:
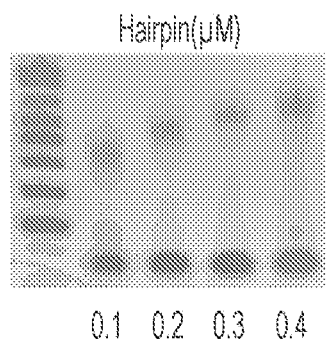
FIG. 21B: PAGE gel displays the concatemer (up to 1000 nt) elongated at different hairpin concentrations (0.1 µM, 0.2 µM, 0.3 µM, 0.4 µM).
Figure 21C:
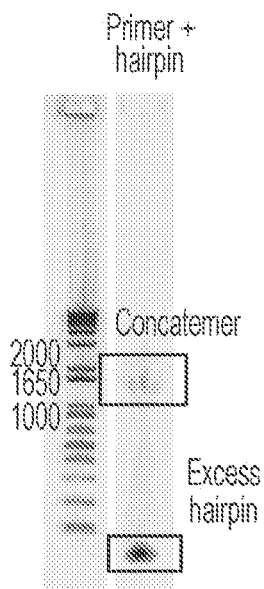
FIG. 21C: ~1.5 kb test concatemer with ~70 binding sites for the imager binding.
Figure 21D:
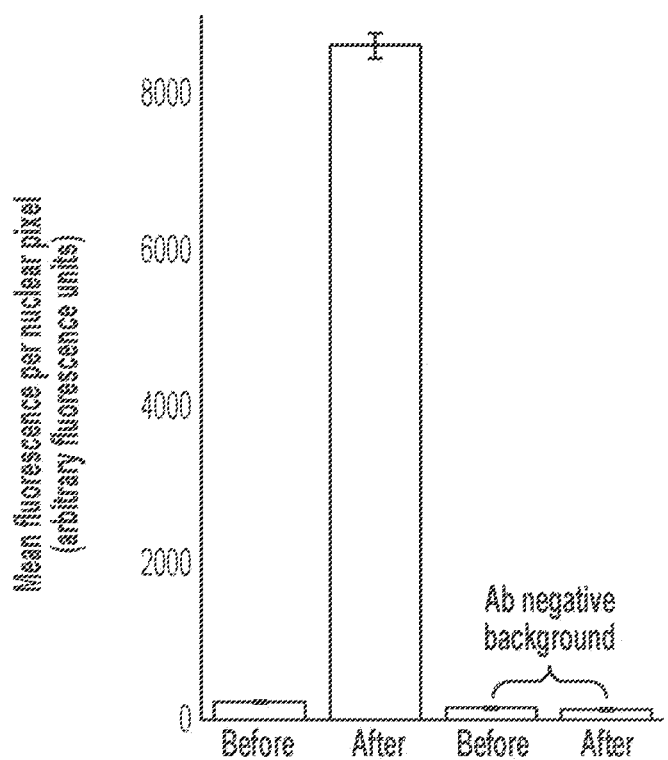
FIG. 21D: ~37-fold higher signal (fluorescent hybridization 2) was obtained comparison to unamplified case (fluorescent hybridization 1) using imager strands with Alexa647. No Ab background shows the negative controls where 1° Ab was omitted. Error bars are the standard error of the mean (n=150-180 cells).

A basic single primer exchange reaction was prepared by incubating hairpin together with 100 nM primer, Bst Large Fragment polymerase and a mixture of nucleotides (dATP, dTTP, and dCTP). The extended primer (concatemer) was visualized by gel electrophoresis (FIG. 21C). The length of the output visualized on a gel constitutes a direct measure of the signal amplification level. In this example, the 1.5 kb long concatemer was expected to yield a maximum 70-fold signal increase, which was calculated assuming the fluorescent strand hybridization length was 20 nt, all concatemers reached this maximum length, and all sites were occupied by fluorophores.

Figure 21E:
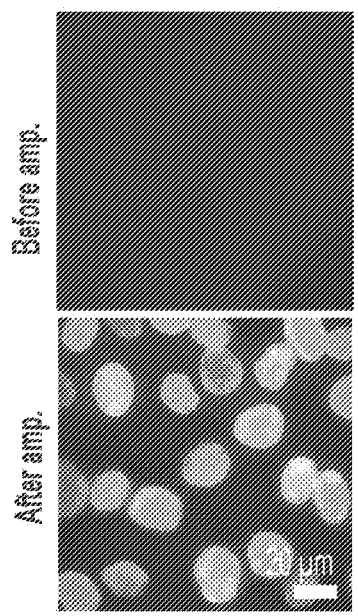
FIG. 21E: Representative images of the cells before and after amplification. Primer (B38 bridge complement+2× p27 site quantification of signal before amplification+p28 site for priming): CTAGATCGAACTATTCGAACACTAAATATTACATCATCATACATCATCATACAACTTAAC (SEQ ID NO:21); Hairpin: ACAACTTAACGGGCCTTTTGGCCCGTTAAGTTGTGTTAAGTTG/3InvdT/ (SEQ ID NO:22); Bridge sequence (B38) conjugated to the secondary antibody: /5ThioMC6-D/TATTTAGTGTTCGAATAGTTCGATCTAG (SEQ ID NO:23).

HeLa cells were fixed with 4% paraformaldehyde, quenched with 100 mM $NH_4Cl$, permeabilized with 0.1% Triton-X100, and blocked with 2% BSA in PBS. Immunostaining was performed using goat anti-Lamin B antibodies, followed by anti-goat secondary antibodies conjugated to the bridge sequence (B38). After washing off the excess antibodies and post-fixation, the pre-extended concatemer was hybridized to the bridges via the B38* sequence. Excess strands were washed off and samples were then incubated with Alexa647-conjugated fluorescent strands that bind the P28 site to measure the baseline signal level in absence of amplification. After first round of imaging, samples were incubated with Alexa647-conjugated fluorescent strands that bind P27 repeats to measure the amplified signal level. After washing the excess fluorescent oligonucleotides with PBS, the samples were imaged using an epifluorescence microscope. The maximum projections of the image stacks are shown in FIG. 21E. Quantification of the fluorescent signal demonstrate an approximately 37-fold higher signal under in situ imaging conditions, which is a substantial improvement in signal level.

Example 10

Multiplexed Imaging Via Signal Destruction

Imaging was validated with two strategies: formamide-induced signal dissociation and USER® cleavage-induced signal dissociation.

In the formamide case, AT-rich 20 mer fluorescent oligonucleotides were synthesized. The fluorescent oligonucleotides had melting temperatures well below room temperature with a 50% formamide in 1×PBS solution. These weak binding oligonucleotides were washed away in the formamide systems, leaving the FISH probes permanently bound. The fluorescent oligonucleotides were successfully washed away with formamide and then re-hybridized to the target in a 1×PBS solution (data not shown).

The USER® enzyme was also used to induce signal dissociation. The USER® enzyme, which cleaves uracil bases (neb.com/products/m5505-user-enzyme), was incorporated into DNA sequences. The enzyme was used to cleave the fluorescent signal strands into multiple short pieces that spontaneously dissociate from the concatemers, effectively washing away the fluorescent signal. The process was validated in cells. Images were taken of cells with 488-labeled probes and uracil-containing 647 fluorescent strands before and after 20 minutes of treatment with USER® diluted from stock by 1:20 in 1×PBS (data not shown).

Example 11

Two-Color Amplification

Figure 15A:
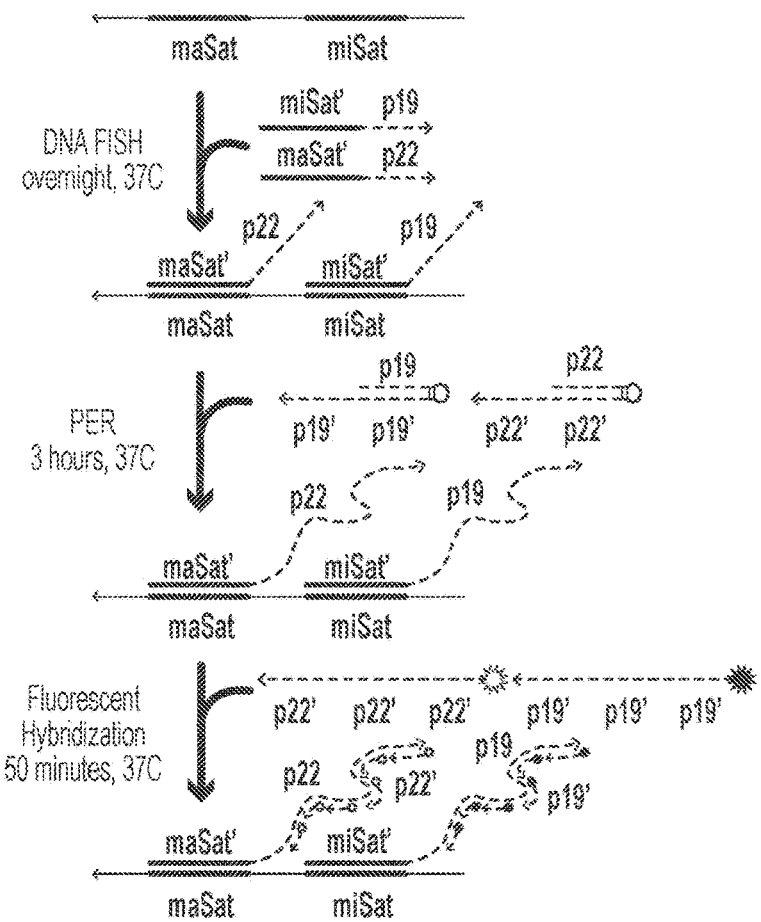
FIGS. 15A-15B: Two-color amplification.
Figure 15B:
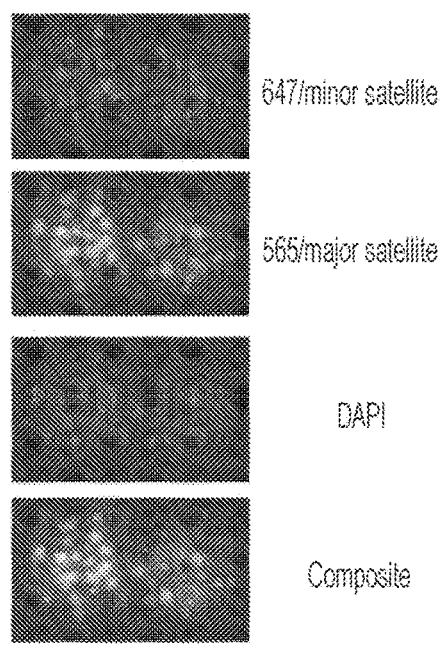

A two-color experiment was also performed on fixed immortalized mouse embryonic fibroblast cells using DNA FISH (FIG. 15A). In addition to the major satellite repeat region targeted in the initial experiment above, the minor satellite repeated region of the chromosomes was also targeted with a different color. This was done by attaching a different primer to the probes for the two different targets and using a different fluorophore on the complementary strands for the in situ synthesized telomeric strands. In this example, primers 19 and 22 were attached to probes targeting the minor satellite and major satellite regions, respectively. The p22' p22' p22' strand, which targeted the major satellite region, contained an ATTO 565 dye, and the p19' p19' p19' strand, which targeted the minor satellite region, contained an Alexa 647 dye. Both targets' primers were extended together with PER hairpins during a 3 hour incubation at 37° C. FIG. 15B shows the results with expected morphologies of the two targets in their respective proper fluorescence channels. Cells were also DAPI-stained as a control.

Example 12

Amplification Visualization

An experiment was designed to get a sense of how much amplification was achieved with the major satellite PER amplification (FIG. 16). A 5' handle was added to the major satellite probe for one Alexa 647-labeled complement to bind (in FIG. 16, this is a binding region of the Alexa 647-labeled p19' p19' p19' strand) while the PER hairpin concentration was varied in three different wells to visualize the increase in localized Alexa 647 signal under the three different PER conditions. The binding region allowed for fluorescence from samples with unamplified probes (i.e., without hairpins during PER incubation) to be compared to samples with amplified probes (i.e., with hairpins during PER incubation). Well 1 contained no hairpin during the 3 hour PER incubation and was therefore expected to have no telomerization on the 3' end of the probe (data not shown). Well 2 incubated 500 nM hairpin and Well 3 incubated 1 µM hairpin (data not shown). With increasing hairpin concentrations, increasing fluorescence values for cells imaged under the same microscope conditions were seen. This is consistent with there being amplification corresponding to PER synthesis, and the results were visualized under two different pixel contrast levels.

Example 13

Combination PER and DEI

Figure 19:
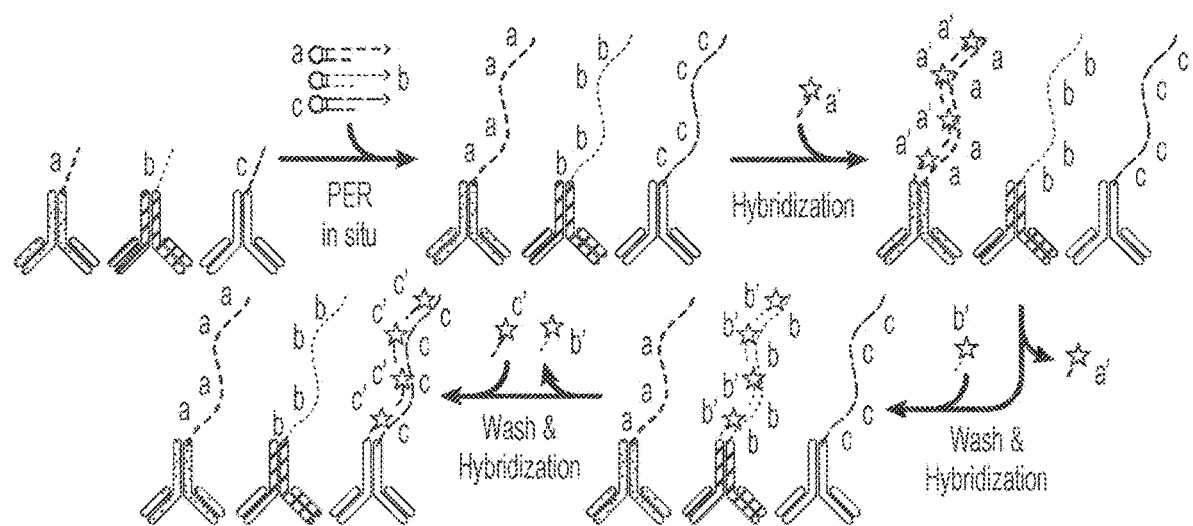
FIG. 19: Simultaneous in situ multiplexed signal amplification by PER and sequential multiplexed detection by DEI.

To date, there has been no published data that demonstrates rapid (achievable in hours) multiplexed (>10-color) detection of proteins (especially at low abundance levels) in thick tissue samples, for example, without expensive instrumentation. By combining primer exchange reactions (PER) with DNA exchange imaging (DEI) methods (see, e.g., WO 2015/138653, published 17 Sep. 2015, incorporated by reference herein), the present disclosure provides a means for accurate composition mapping of neuronal tissues, for example. In this Example, to achieve highly sensitive and multiplexed in situ immunofluorescence, immunofluorescence is performed with tens of primary antibodies conjugated to orthogonal PER primer sequences, the orthogonal PER primer sequences are extended simultaneously by in situ PER, and DNA exchange imaging is performed for sequential detection of all targets (FIG. 19). Thus, in this Example, a DEI-based multiplexing strategy is combined with PER amplification by using orthogonal sequence design to allow rapid multiplexed detection of rare targets in deep tissue samples.

To be able to perform multiplexed immunofluorescence using DEI and PER, staining is performed with primary antibodies that are conjugated directly with DNA. To show that PER can function as expected in the absence of signal amplification and labeling density enhancement that are provided by secondary antibodies, experiments with anti-α-tubulin primary antibody conjugated directly to DNA oligos (28-nt long) were performed, which yielded extensive labeling of the microtubules (data not shown). Additional experiments are performs using a diverse set of antibody-targeting proteins of different expression levels.

After each round of imaging, stably bound imager strands are removed.

Using different spectral channels, 4× multiplexing can be achieved (see above). To demonstrate higher levels of multiplexing a 3-tier system is establish, going from in silico, to in vitro, to in situ. For the in silico design of orthogonal sequences, an experimental pipeline to design 8 different primers is produced. First, a library of all 9-nt long primer sequences that bind to their full complements with a probability of 98.2%-99.2% is constructed. The binding probability is calculated as the probability of 100 nM strand binding to 100 nM complementary strand at 0° C., executing NUPACK tools (24, 25) from the command-line. From this library, sequences that contain a stretch of CCCC are filtered out, because the complement for these would need to carry GGGG in the hairpin, which has the undesired potential to form a quadruplex DNA structure. An optimization algorithm is then used to randomly create sets of n sequences from the library and replace them until a set is obtained that satisfies the orthogonality constraints. To qualify, all the primers in a the set should pass the following tests: (i) Homodimerization check: Self-binding probability is <20%. (ii) Heterodimerization check: Probability of binding to all primers is <20%. (iii) Cross-talk check: Binding to all other complementary sequences for the primers in the set is <0.08%. (iv) Reverse cross-talk check: binding of all complements to all primers in the set is <0.08%. This ensures doubling the effective weighting of this orthogonality constraint and averaging out small thermodynamics differences that might arise depending on which orientation of strands was chosen. (v) Universal sequence binding: Binding probability of all primers to the selected hairpin loop sequence (in this example: 'GCCTTTTG') is <20%. Then the selected random primer sets were subject to single-stranded constraint that we have established empirically. According to this, 50-nt sequences are built concatenating the primer sequence (followed by an A base) 5 times. These 50 mers are completely single-stranded (fully unpaired) at least 0.06% of the time at 0° C. Using this pipeline, 8 orthogonal primer sequences were designed in <2 hours of computation time. With further analysis of the design criteria, tens of orthogonal sequences can be designed to enable high-levels of PER-enhanced multiplexed in situ imaging. To create a set of ~50 orthogonal strands, other methods such as Simulated Annealing and Genetic Algorithms may be used.

Figure 20:
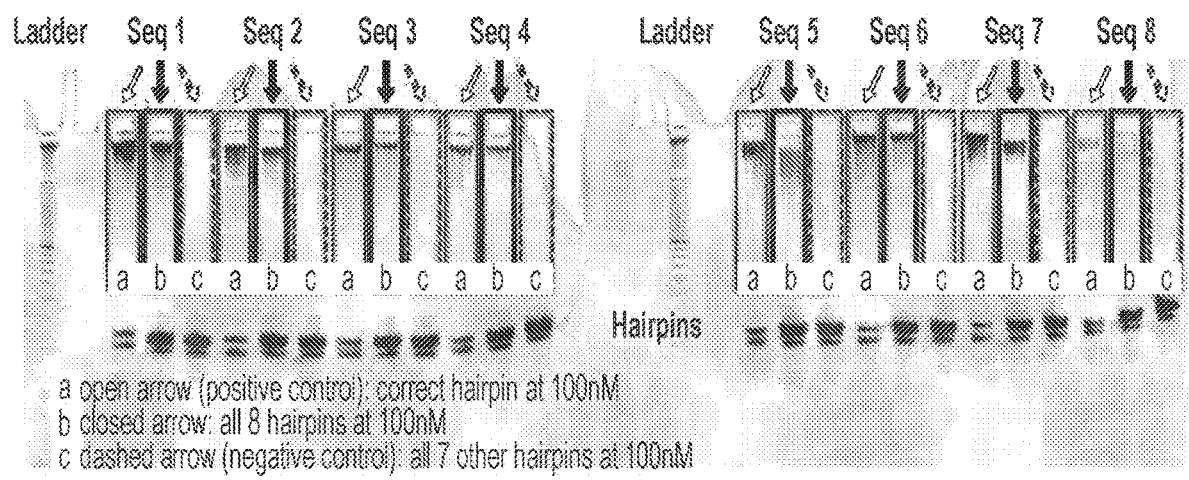
FIG. 20: In vitro PER with 8 orthogonal strands. Reaction products were visualized on 15% denaturing gel after 2 hour incubation at 37° C. Dense bands at the top showing the extended product correspond to 1.5 kb, visualized by SYBR™ Gold staining. The lower dense bands show the excess hairpins.

Following in silico design, the selected sequences are evaluated in vitro. Gel assays are used to perform crosstalk check between the reactions when PER is performed simultaneously for all the primers. Initially, PER was performed in vitro by mixing each primer sequences with its complementary hairpin (positive control), the hairpins cognate to all 8 primers or with all primers except the complementary hairpin for the particular primer (negative control). The products from each reaction were analyzed by gel electrophoresis (FIG. 20). This experimental scheme is used for high-throughput validation of orthogonality for 50 in silico-designed strands.

To quantitatively check for crosstalk at the level of imagers at high-throughput, a spectrally barcoded nanorod origami platform is used (see, e.g., WO 2015/138653, published 17 Sep. 2015). In addition to the 3 fluorescent spots, a 4th spectral channel (deep red) and an additional spot position is used to present the primer sequence. Origami structures barcoded for each primer sequence (~50 species) are mixed together and immobilized on the mica surface (which protects the immobilized origami backbone from the action of the strand displacing polymerase). They are all extended simultaneously by PER providing all the hairpins. Then, sequentially each complementary imager is added, TIRF imaging is performed, and imagers are displaced (by USER enzyme) and washed off, and the new imagers are added until all primer-imager sequence pairs are imaged. Starting with a pool of 50 sequences, the top 30 are chosen for in situ validation.

Orthogonal sequences confirmed in vitro are validated in situ using a fast fluorescence assay on multi-well plates with cells. A distinct cellular structure (such as mitochondria or microtubules) is targeted by immunofluorescence, with an antibody presenting a bridge oligo for primer binding. Orthogonal primer sequences carrying the same bridge binding sequence are hybridized to each well. Following a similar scheme to the gel assays, for each primer sequence there are three wells: the positive control (only the correct complementary hairpin is added), the negative control (all hairpins except the complementary) and experimental condition (all hairpins are added). PER is performed for each well simultaneously followed by incubation with all imagers. Unbound imagers are washed off and the level of the fluorescence signal is evaluated to detect any undesired binding. Sequences verified with these methods are conjugated to the primary antibodies marking neuronal and cytokine targets.

Example 14

Control of Concatemer Length Extension

Experiments were performed to investigate the effect of concatemer length on signal amplification. A basic signal primer exchange reaction was prepared by incubating variable concentrations of hairpins (0.1 to 0.4 0.4 µM) together with 100 nM primer, Bst Large Fragment polymerase and a mixture of nucleotides (dATP, dTTP, and dCTP). The extended primer (concatemer) was then visualized by gel electrophoresis (FIG. 21B). The length of the output visualized on a gel represented a direct measure for the expected signal amplification level. The tight control and programmability of the extension level is shown. Concatemer length can also be controlled by other parameters such as incubation time or dNTP concentration.

Example 15

Branched PER Signal Amplification

This Example demonstrates different branched structures and the resulting signal amplification. PER strands can be applied in a cascade fashion to form branched structures through the hybridization of additional concatemers onto the primary concatemer. Formation of the branches can be performed by simultaneous or sequential application of the pre-concatemers to the target. Branched concatemers may also be formed by direct in situ PER. The creation of branches increases the number of binding sites for the fluorescent oligonucleotides, enabling further signal amplification.

Figure 22B:
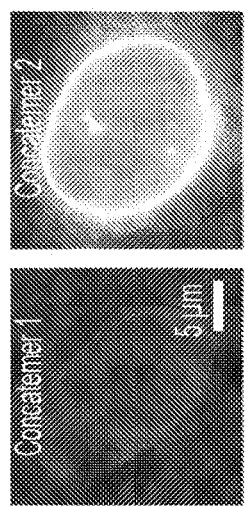
FIG. 22B: Pre-extended concatemers were applied on HeLa cells immunolabeled for Lamin B sequentially and branched structure was assembled in situ.

Branched structures were sequentially assembled as follows. HeLa cells were fixed with 4% paraformaldehyde, quenched with 100 mM $NH_4Cl$, permeabilized with 0.1% Triton-X100 and blocked with 2% BSA in PBS. Immunostaining was performed using goat anti-Lamin B antibodies, followed by anti-goat secondary antibodies conjugated to the bridge sequence (B38). After washing off excess the antibodies and post-fixation, pre-extended Concatemer 1 (P30) was hybridized to the bridges via the B38* sequence. Excess strands were washed off, and a second hybridization was performed with Concatemer 2. Concatemer 2 was pre-extended using a primer strand with 3 repeats of the binding sites of P30, followed by a P25 priming site. Pre-extensions were performed in vitro with 100 nM primer hairpin incubated with hairpin, Bst Large Fragment polymerase and a mixture of nucleotides (dATP, dTTP, and dCTP). Excess strands were washed off at 37° C. Samples were then incubated with Alexa647-conjugated fluorescent strands that bind P30 repeats (to detect Concatemer 1, no branching) or P25 repeats (to detect Concatemer 2, after branching). After washing the excess fluorescent oligonucleotides with PBS, the samples were imaged using an epifluorescence microscope. The maximum projections of the image stacks are shown in FIGS. 22A-22B. Quantification of the fluorescent signal yields ~5-fold higher amplification with branching compared to no branching.

Figures 22C, 22D, 22E:
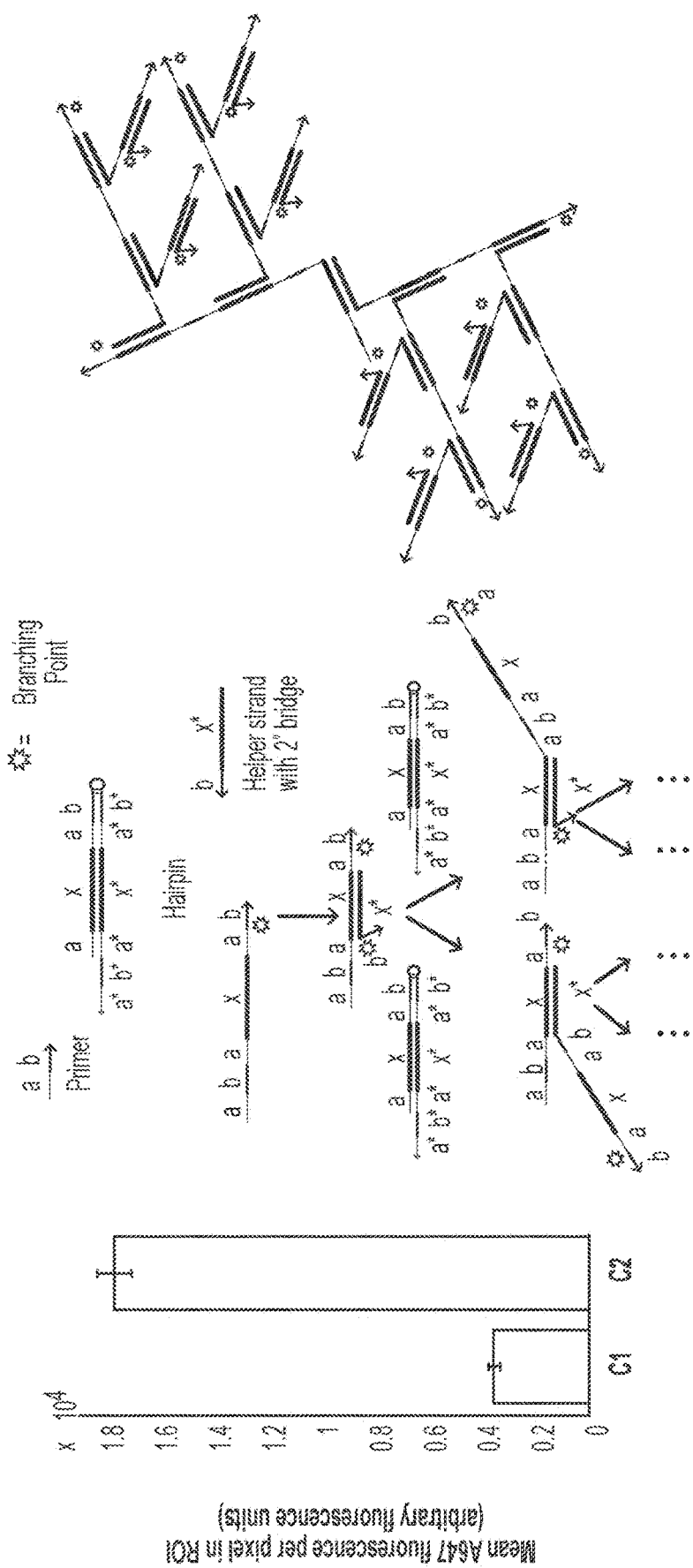
FIG. 22C: Quantification of signal improvement via branching with second concatemer (C2) vs. first concatemer alone (C1).
FIG. 22D: In situ dendritic growth mechanism: The triggered synthesis of a dendrimer with exponential growth kinetics uses a single stranded helper strand, which mediates branching, in addition to the hairpin.
FIG. 22E: An example of autonomous in situ synthesis of dendritic structure. Bridge sequence (B38) conjugated to the secondary antibody: /5ThioMC6-D/TATTTAGTGTTCGAATAGTTCGATCTAG (SEQ ID NO:24); For concatemer 1: Primer (B38 bridge complement+2× p27 site for basal signal quantification+p28 site for priming): CTAGATCGAACTATTCGAACACTAAATATTACATCATCATACATCATCATACAACTTAAC (SEQ ID NO:25); Hairpin: ACAACTTAACGGGCCTTTTGGCCCGTTAAGTTGTGTTAAGTTG/3InvdT/ (SEQ ID NO:26); Concatemer 2: Primer (3× p28 site for hybridization to Concatemer 1+2× p30 site for quantification of signal before second round of amplification+p25 site for priming): GTTAAGTTGTGTTAAGTTGTGTTAAGTTGTAAATACTCTCAAATACTCTCTTCCAATAATA (SEQ ID NO:27); Hairpin: ACCAATAATAGGGCCTTTTGGCCCTATTATTGGTTATTATTGG/3InvdT/ (SEQ ID NO: 28); Fluorescent strand 1 (p30*): /5Alex647N/TTGAGAGTATTTGAGAGTATTT/3InvdT/ (SEQ ID NO: 29); Fluorescent strand 2 (p25*): /5Alex647N/TTTATTATTGGTTATTATTGGT/3InvdT/ (SEQ ID NO:30).

Branches can also be built by other forms of assembly such as dendritic growth as shown schematically in FIGS. 22D-22E.

Figure 23:
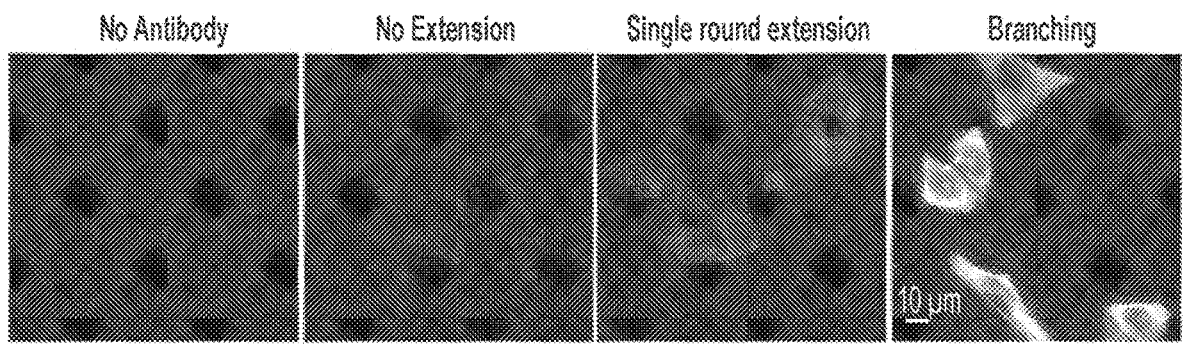
FIG. 23: HeLa cells stained for alpha-tubulin (using DNA-conjugated primary antibodies), demonstrating an example of branched amplification. Bridge sequence conjugated to the primary antibody: /5ThioMC6-AATTCTATGACACCGCCACGCCCTATATCCTCGCAATAACCC (SEQ ID NO:31); Concatemer 1: Fluorescent Primer (Fluorophore+bridge complement+p30 priming site): /5ATTO565N/TTTGGGTTATTGCGAGGATATAGGGCGTGGCGGTGTCATAGAATTTTTTTAATACTCTC (SEQ ID NO:32); Hairpin: AAATACTCTCGGGCCTTTTGGCCCGAGAGTATTTGAGAGTATT/3InvdT/ (SEQ ID NO:33); Fluorescent strand (p30*): /5ATTO565N/TTGAGAGTATTTGAGAGTATTT/3InvdT/ (SEQ ID NO:42); Concatemer 2: Primer (3× p30 site for hybridization to Concatemer 1+p33 site for priming): GAGAGTATTTGAGAGTATTTGAGAGTATTTTTCCTTCTATT (SEQ ID NO:34); Hairpin: ACCTTC- TATTGGGCCTTTTGGCC-
CAATAGAAGGTAATAGAAGG/3InvdT/ (SEQ ID NO:35); Fluorescent (p33*): /5ATTO565N/ TTAATAGAAGGTAATAGAAGGT/3InvdT/ (SEQ ID NO:36).

Branched PER signal amplification was also examined using cells stained directly with primary antibodies. As described above, HeLa cells were fixed with 4% paraformaldehyde, quenched with 100 mM $NH_4Cl$, permeabilized with 0.1% Triton-X100 and blocked with 2% BSA in PBS. Immunostaining was performed using rat anti-alpha tubulin antibodies conjugated to a 42-nt bridge sequence (B0). After washing off the excess antibodies and post-fixation, pre-extended Concatemer 1 (P30) was hybridized to the bridges via the B38* sequence for 4 h at 37° C. Excess strands were washed off, and a second hybridization was performed with Concatemer 2 overnight at 37° C. Concatemer 2 was pre-extended using a primer strand with 3 repeats of P30 binding sites, followed by a P33 priming site. Pre-extensions were performed in vitro with 100 nM primer hairpin incubated with hairpin, Bst Large Fragment polymerase and a mixture of nucleotides (dATP, dTTP, and dCTP). Excess strands were washed off at 37° C. Samples were then incubated for 100 min at 37° C. with 2 µM Alexa565-conjugated fluorescent strands that bind P33 repeats. After washing the excess fluorescent oligos with PBS, the samples were imaged using an epifluorescence microscope. The maximum projections of the image stacks are shown in FIG. 23. The no antibody control demonstrates the absence of background staining in samples where the primary antibody was omitted but all the other steps were applied. The no extension control shows samples hybridized with the unextended primer instead of the concatemer. The single round extension sample was only hybridized with Concatemer 1, and was visualized by 2 µM Alexa565-conjugated fluorescent strands that bind P30 repeats.

Example 16

Signal Amplification in Formalin Fixed Paraffin-Embedded (FFPE) Samples

This Example demonstrates the applicability of the signal amplification method for FFPE-samples commonly used in medical tissue analysis and archival, where an excess of molecules may render the FFPE preparation procedure difficult. Incubation times for antibodies and DNA strands can be shortened substantially for faster diagnostic applications.

Figure 24:
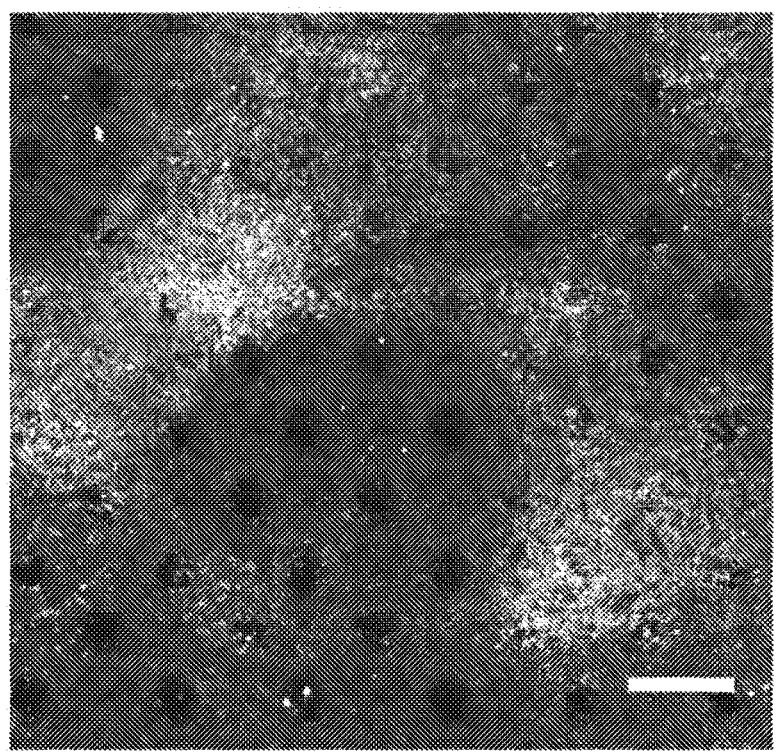
FIG. 24: Immunostaining of FFPE samples. 4 μm thick tonsil samples stained T-cell marker CD3 labeling interfollicular T cell zone surrounding the germinal center (using DNA-conjugated secondary antibodies). Scale bar 200 μm. Primer (bridge complement/B38*+p27 for priming): CTA-GATCGAACTATTCGAACACTAAATATTCATCATCAT (SEQ ID NO:37); Hairpin (27): ACATCAT-CATGGGCCTTTTGGCCCATGATGATGTATGATGATG/3InvdT/ (SEQ ID NO:38); Bridge sequence (B38) conjugated to the secondary antibody: /5ThioMC6-D/TATTTAGTGTTCGAATAGTTCGATCTAG (SEQ ID NO:39); Fluorescent (p27*): /5Alex647N/TTATGAT-GATGTATGATGATGT/3InvdT/ (SEQ ID NO:40).

In the experiment, 4 µm-thick human tonsil samples were formalin-fixed and paraffin-embedded using standard protocols. After antigen retrieval, samples were blocked and permeabilized with PBS containing 2% bovine serum albumin and 0.3% Triton-X100. Primary antibody staining was performed with rabbit anti-human CD3 antibodies at 4° C. After washing excess antibodies, the samples were incubated with anti-rabbit secondary antibodies conjugated to the B38 bridge sequence. After washing excess antibodies, the samples were post-fixed with 4% paraformaldehyde in PBS for 10 min and quenched with 100 mM ammonium chloride in PBS for 5 min and washed with PBS containing 0.3% Triton. The PER concatemers used for the amplifications were pre-extended using 100 nM P27 primer with which contains the complementary bridge binding handle on the 5' end. The reaction was performed with 0.5 µM hairpin, Bst Large Fragment polymerase, and a mixture of nucleotides (dATP, dTTP, and dCTP) for 1 hour. The polymerase was then heat-inactivated and 1:10 dilution of the reaction mixture used for hybridization onto the FFPE sample at 37° C. overnight. Excess strands were washed away with PBS containing 0.3% Triton at 37° C. Samples were then incubated for 2 hours with 1 µM fluorescent strands. After washing with PBS, the samples were imaged using a confocal microscope. As shown in FIG. 24, the CD3-positive T-cells in the interfollicular T-cell zone were visualized around the germinal centers as expected for tonsil samples.

REFERENCES

[1] Choi, Harry M T, et al. "Programmable in situ amplification for multiplexed imaging of mRNA expression." Nature biotechnology 28.11 (2010): 1208-1212.
[2] Lizardi, Paul M., et al. "Mutation detection and single-molecule counting using isothermal rolling-circle amplification." Nature genetics 19.3 (1998): 225-232.
[3] Schönhuber, W., et al. "Improved sensitivity of whole-cell hybridization by the combination of horseradish peroxidase-labeled oligonucleotides and tyramide signal amplification." Applied and Environmental Microbiology 63.8 (1997): 3268-3273.
[4] Blackburn, Elizabeth H., and Kathleen Collins. "Telomerase: an RNP enzyme synthesizes DNA." Cold Spring Harbor perspectives in biology 3.5 (2011): a003558.
[5] DeLong, Edward F., Gene S. Wickham, and Norman R. Pace. "Phylogenetic stains: Ribosomal RNA-based probes for the identification of single cells." Science 243.4896 (1989): 1360.
[6] Amann, Rudolf I., Lee Krumholz, and David A. Stahl. "Fluorescent-oligonucleotide probing of whole cells for determinative, phylogenetic, and environmental studies in microbiology." Journal of bacteriology 172.2 (1990): 762-770.

[7] Kazane, Stephanie A., et al. "Site-specific DNA-antibody conjugates for specific and sensitive immuno-PCR." Proceedings of the National Academy of Sciences 109.10 (2012): 3731-3736.
[8] Yildirim, Eda, et al. "X-chromosome hyperactivation in mammals via nonlinear relationships between chromatin states and transcription." Nature structural & molecular biology 19.1 (2012): 56-61.
[9] Beliveau, Brian J., et al. "Versatile design and synthesis platform for visualizing genomes with Oligopaint FISH probes." Proceedings of the National Academy of Sciences 109.52 (2012): 21301-21306.
[10] Beliveau, Brian J., et al. "Single-molecule super-resolution imaging of chromosomes and in situ haplotype visualization using Oligopaint FISH probes." Nature communications 6 (2015).
[11] Casanova, Miguel, et al. "Heterochromatin reorganization during early mouse development requires a single-stranded noncoding transcript." Cell reports 4.6 (2013): 1156-1167.
[12] Jungmann, Ralf, et al. "Multiplexed 3D cellular super-resolution imaging with DNA-PAINT and Exchange-PAINT." Nature methods 11.3 (2014): 313.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed:

1. A multiplexed target detection method, comprising:
(a) combining a sample containing a plurality of nucleic acid targets with a plurality of probe strands, each probe strand comprising (i) an unpaired 5' target domain complementary to one of the nucleic acid targets and (ii) an unpaired 3' primer domain, and producing a first reaction mixture comprising molecular targets bound to probe strands;
(b) combining the first reaction mixture produced in step (a) with dNTPs, strand-displacing polymerase, and a plurality of catalytic molecules, each catalytic molecule comprising, 5' to 3', a first domain, a second domain, and a third domain wherein the first domain is bound to the second domain, and the third domain is an unpaired 3' toehold domain complementary to the unpaired 3' primer domain of one of the probe strands, and producing a second reaction mixture comprising nucleic acid concatemers bound to molecular targets; and
(c) combining the second reaction mixture produced in step (b) with a plurality of signal strands, each signal strand linked to a different detectable molecule and comprising a domain complementary to the unpaired 3' primer domain of one of the probe strands, and producing labeled concatemers labeled by a plurality of signal strands.

2. A multiplexed target detection method, comprising:
(a) combining a plurality of probe strands with dNTPs, strand-displacing polymerase, and a plurality of catalytic molecules, wherein each probe strand comprises (i) an unpaired 5' target domain complementary to a nucleic acid target of a plurality of nucleic acid targets and (ii) an unpaired 3' primer domain, and wherein each catalytic molecule comprises, 5' to 3', a first domain, a second domain, and a third domain wherein the first domain is bound to the second domain, and the third domain is an unpaired 3' toehold domain complementary to the unpaired 3' primer domain of one of the probe strands, and producing a first reaction mixture comprising nucleic acid concatemers bound to probe strands;
(b) combining the first reaction mixture produced in step (a) with a sample containing the plurality of nucleic acid targets and producing a second reaction mixture comprising nucleic acid concatemers bound to molecular targets; and
(c) combining the second reaction mixture produced in step (b) with a plurality of signal strands, wherein each signal strand is linked to a different detectable molecule and comprises a domain complementary to the unpaired 3' primer domain of one of the probe strands, and producing labeled concatemers labeled by a plurality of signal strands.

3. The method of claim 1, wherein the catalytic molecules are comprised of DNA and/or RNA.

4. The method of claim 1, wherein the first domain of each catalytic molecule is bound to the second domain of the same catalytic molecule, wherein the second domain of each catalytic molecule comprises a sequence identical to the third domain of the same catalytic molecule, and/or wherein the first domain each catalytic molecule comprises a sequence wholly complementary to the second domain of the same catalytic molecule.

5. The method of claim 1, wherein each catalytic molecule further comprises a stopper molecule or modification that terminates polymerization located between the first and second domains of the same catalytic molecule.

6. The method of claim 5, wherein the stopper molecule or modification that terminates polymerization is selected from a triethylene glycol (TEG), 18-atom hexa-ethylene glycol, adenylation, azide, digoxigenin, cholesteryl-TEG, 3-cyanovinylcarbazole (CNVK), iso-dG and iso-dC, wherein the stopper molecule is guanine and the catalytic molecule is comprised of adenine, thymine and cytosine, or wherein the stopper molecule is cytosine and the catalytic molecule is comprised of adenine, thymine and guanine.

7. The method of claim 1, wherein each catalytic molecule is a catalytic hairpin molecule further comprising a loop domain located between the first and second domains.

8. The method of claim 7, wherein each catalytic hairpin molecule is comprised of a single strand of DNA having a length of 25-300 nucleotides.

9. The method of claim 1, wherein the probe strands are comprised of DNA and/or RNA.

10. The method of claim 1, wherein each probe strand has a length of 10-50 nucleotides, the target domain of each probe strand has a length of 5-25 nucleotides, and/or the primer domain of each probe strand has a length of 5-25 nucleotides.

11. The method of claim 1, wherein the nucleic acid target comprises DNA and/or RNA.

12. The method of claim 1, wherein the nucleic acid target is chromosomal DNA, mRNA, or miRNA.

13. The method of claim 1, wherein the detectable molecule of the signal strands is a fluorophore.

14. The method of claim 1, wherein each of the signal strands has a length of 10-30 nucleotides.

15. The method of claim 1, wherein the strand-displacing polymerase is selected from phi29 DNA polymerases, Bst DNA polymerases, and Bsu DNA polymerase, large fragment.

16. The method of claim 1, wherein:
the plurality of probe strands comprises 2-10,000 of the probe strands;
the plurality of catalytic molecules comprises 2-10,000 of the catalytic molecules; and
the plurality of signal strands comprises 2-10,000 of the signal strands.

17. The method of claim 1, wherein the sample is a cell sample or a tissue sample.

18. A multiplexed target detection method comprising:
(a) combining a sample containing a plurality of nucleic acid targets with a first plurality of probe strands, each probe strand of the first plurality comprising (i) an unpaired 5' target domain a complementary to one of the nucleic acid targets and (ii) an unpaired 3' primer domain b, and producing a reaction mixture comprising molecular targets bound to probe strands;
(b) combining the reaction mixture produced in step (a) with dNTPs, strand-displacing polymerase, and a first plurality of catalytic molecules, each catalytic molecule of the first plurality comprising, 5' to 3', domain $a_1$, domain x, domain $a_2$, domain $b_1$, domain $b_1$*, domain $a_2$*, domain x*, domain $a_1$*, domain $b_2$*, and domain $a_3$*, wherein domain $a_1$, domain x, domain $a_2$, and domain $b_1$ respectively bind to domain $b_1$*, domain $a_2$*, domain x*, and domain $a_1$*, and domains $b_2$* and domain $a_3$* form an unpaired 3' toehold domain complementary to the probe strand of the first plurality, and producing a reaction mixture comprising a first plurality of nucleic acid concatemers bound to molecular targets;
(c) combining the reaction mixture produced in step (b) with a second plurality of probe strands, each probe strand of the second plurality comprising (i) an unpaired 5' domain x* complementary to domain x of the catalytic molecules and (ii) an unpaired 3' primer domain b complementary to domains $b_1$ and $b_2$* of the catalytic molecules, and producing a reaction mixture comprising concatemers bound to probe strands; and (d) combining the reaction mixture produced in step (c) with dNTPs, strand-displacing polymerase, and a second plurality of catalytic molecules, each catalytic molecule of the second plurality comprising, 5' to 3', domain $a_1$, domain x, domain $a_2$, domain $b_1$, domain $b_1$*, domain $a_2$*, domain x*, domain $a_1$*, domain $b_2$*, and domain $a_3$*, wherein domain $a_1$, domain x, domain $a_2$, and domain $b_1$ respectively bind to domain $b_1$*, domain $a_2$*, domain x*, and domain $a_1$*, and domains $b_2$* and domain $a_3$* form an unpaired 3' toehold domain complementary to the probe strand of the first plurality, and producing branched concatemers.

19. The method of claim 18, further comprising:
(e) combining the reaction mixture produced in step (d) with a plurality of signal strands, each signal strand linked to a different detectable molecule and comprising a domain complementary to the unpaired 3' primer domain b of the probe strands of the first and/or second plurality of probe strands, and producing labeled concatemers labeled by a plurality of signal strands.

20. The method of claim 1, further comprising:
(d) imaging the labeled concatemers.

21. The method of claim 2, further comprising:
(d) imaging the labeled concatemers.

22. The method of claim 19, further comprising:
(f) imaging the labeled concatemers.

* * * * *

SEQUENCE LISTING

```
<160> NUMBER OF SEQ ID NOS: 42

<210> SEQ ID NO 1
<211> LENGTH: 10
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: modified by /5Cy5/

<400> SEQUENCE: 1
ttctcttatt                                                            10

<210> SEQ ID NO 2
<211> LENGTH: 43
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (43)..(43)
<223> OTHER INFORMATION: modified by /3InvdT/

<400> SEQUENCE: 2
actaaattca gggcctttg gccctgaatt tagtaataag aga                        43

<210> SEQ ID NO 3
<211> LENGTH: 43
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (43)..(43)
<223> OTHER INFORMATION: modified by /3InvdT/

<400> SEQUENCE: 3
atatcccata gggcctttg gccctatggg atattgaatt tag                        43
```

<210> SEQ ID NO 4
<211> LENGTH: 43
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (43)..(43)
<223> OTHER INFORMATION: modified by /3InvdT/

<400> SEQUENCE: 4
attacactac gggccttttg gcccgtagtg taattatggg ata        43

<210> SEQ ID NO 5
<211> LENGTH: 43
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (43)..(43)
<223> OTHER INFORMATION: modified by /3InvdT/

<400> SEQUENCE: 5
atattaaacc gggccttttg gcccggttta atatgtagtg taa        43

<210> SEQ ID NO 6
<211> LENGTH: 43
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (43)..(43)
<223> OTHER INFORMATION: modified by /3InvdT/

<400> SEQUENCE: 6 atcattttc gggccttttg gcccgaaaaa tgatggttta ata        43

<210> SEQ ID NO 7
<211> LENGTH: 43
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (43)..(43)
<223> OTHER INFORMATION: modified by /3InvdT/

<400> SEQUENCE: 7
atctcttatt gggccttttg gcccaataag agataataag aga        43

<210> SEQ ID NO 8
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: modified by /5ATTO565N/
<220> FEATURE:
<221> NAME/KEY: misc_feature
<222> LOCATION: (22)..(22)
<223> OTHER INFORMATION: modified by /3InvdT/

<400> SEQUENCE: 8
ttaataagag ataataagag at                                                 22

<210> SEQ ID NO 9
<211> LENGTH: 55
<212> TYPE: DNA
<213> ORGANISM: Artificial sequence
<220> FEATURE:
<223> OTHER INFORMATION: Synthetic polynucleotide

<400> SEQUENCE: 9
ccactgtagg acgtggaata tggcaagaaa actgaaaatc atggttcatc atcat           55

<210> SEQ ID NO 10
<211> LENGTH: 43
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (43)..(43)
<223> OTHER INFORMATION: modified by /3InvdT/

<400> SEQUENCE: 10
acatcatcat gggccttttg gcccatgatg atgtatgatg atg                        43

<210> SEQ ID NO 11
<211> LENGTH: 43
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (43)..(43)
<223> OTHER INFORMATION: modified by /3InvdT/

<400> SEQUENCE: 11
accaataata gggccttttg gccctattat tggttattat tgg                        43

<210> SEQ ID NO 12
<211> LENGTH: 39
<212> TYPE: DNA
<213> ORGANISM: Artificial sequence
<220> FEATURE:
<223> OTHER INFORMATION: Synthetic polynucleotide

<400> SEQUENCE: 12
ctagatcgaa ctattcgaac actaaatatt ccaataata                             39

<210> SEQ ID NO 13
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: modified by /5ThioMC6-D/

<400> SEQUENCE: 13
tatttagtgt tcgaatagtt cgatctag                                         28

<210> SEQ ID NO 14

```
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: modified by /5Alex647N/
<220> FEATURE:
<221> NAME/KEY: misc_feature
<222> LOCATION: (22)..(22)
<223> OTHER INFORMATION: modified by /3InvdT/

<400> SEQUENCE: 14
tttattattg gttattattg gt                                              22

<210> SEQ ID NO 15
<211> LENGTH: 53
<212> TYPE: DNA
<213> ORGANISM: Artificial sequence
<220> FEATURE:
<223> OTHER INFORMATION: Synthetic polynucleotide

<400> SEQUENCE: 15
agatgagtga gttacactga aaaacacatt cgttggaaac ggtttctctt att            53

<210> SEQ ID NO 16
<211> LENGTH: 55
<212> TYPE: DNA
<213> ORGANISM: Artificial sequence
<220> FEATURE:
<223> OTHER INFORMATION: Synthetic polynucleotide

<400> SEQUENCE: 16
ccactgtagg acgtggaata tggcaagaaa actgaaaatc atggttttac actac          55

<210> SEQ ID NO 17
<211> LENGTH: 43
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (43)..(43)
<223> OTHER INFORMATION: modified by /3InvdT/

<400> SEQUENCE: 17
atctcttatt gggccttttg gcccaataag agataataag aga                       43

<210> SEQ ID NO 18
<211> LENGTH: 43
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (43)..(43)
<223> OTHER INFORMATION: modified by /3InvdT/

<400> SEQUENCE: 18
attacactac gggccttttg gcccgtagtg taatgtagtg taa                       43

<210> SEQ ID NO 19
<211> LENGTH: 32
<212> TYPE: DNA
<213> ORGANISM: Artificial sequence
```

```
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: modified by /5Alex647N/
<220> FEATURE:
<221> NAME/KEY: misc_feature
<222> LOCATION: (32)..(32)
<223> OTHER INFORMATION: modified by /3InvdT/

<400> SEQUENCE: 19
ttaataagag ataataagag ataataagag at                                    32

<210> SEQ ID NO 20
<211> LENGTH: 32
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: modified by /5ATTO565N/
<220> FEATURE:
<221> NAME/KEY: misc_feature
<222> LOCATION: (32)..(32)
<223> OTHER INFORMATION: modified by /3InvdT/

<400> SEQUENCE: 20
ttgtagtgta atgtagtgta atgtagtgta at                                    32

<210> SEQ ID NO 21
<211> LENGTH: 60
<212> TYPE: DNA
<213> ORGANISM: Artificial sequence
<220> FEATURE:
<223> OTHER INFORMATION: Synthetic polynucleotide

<400> SEQUENCE: 21
ctagatcgaa ctattcgaac actaaatatt acatcatcat acatcatcat acaacttaac      60

<210> SEQ ID NO 22
<211> LENGTH: 43
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (43)..(43)
<223> OTHER INFORMATION: modified by /3InvdT/

<400> SEQUENCE: 22
acaacttaac gggccttttg gcccgttaag ttgtgttaag ttg                        43

<210> SEQ ID NO 23
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: modified by /5ThioMC6-D/

<400> SEQUENCE: 23
tatttagtgt tcgaatagtt cgatctag                                         28
```

<210> SEQ ID NO 24
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: modified by /5ThioMC6-D/

<400> SEQUENCE: 24
tatttagtgt tcgaatagtt cgatctag                                28

<210> SEQ ID NO 25
<211> LENGTH: 60
<212> TYPE: DNA
<213> ORGANISM: Artificial sequence
<220> FEATURE:
<223> OTHER INFORMATION: Synthetic polynucleotide

<400> SEQUENCE: 25
ctagatcgaa ctattcgaac actaaatatt acatcatcat acatcatcat acaacttaac    60

<210> SEQ ID NO 26
<211> LENGTH: 43
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (43)..(43)
<223> OTHER INFORMATION: modified by /3InvdT/

<400> SEQUENCE: 26
acaacttaac gggcctttttg gcccgttaag ttgtgttaag ttg                    43

<210> SEQ ID NO 27
<211> LENGTH: 61
<212> TYPE: DNA
<213> ORGANISM: Artificial sequence
<220> FEATURE:
<223> OTHER INFORMATION: Synthetic polynucleotide

<400> SEQUENCE: 27
gttaagttgt gttaagttgt gttaagttgt aaatactctc aaatactctc ttccaataat    60
a                                                                   61

<210> SEQ ID NO 28
<211> LENGTH: 43
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (43)..(43)
<223> OTHER INFORMATION: modified by /3InvdT/

<400> SEQUENCE: 28
accaataata gggcctttttg gccctattat tggttattat tgg                    43

<210> SEQ ID NO 29
<211> LENGTH: 22
<212> TYPE: DNA
<213> ORGANISM: Artificial sequence -continued

```
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: modified by /5Alex647N/
<220> FEATURE:
<221> NAME/KEY: misc_feature
<222> LOCATION: (22)..(22)
<223> OTHER INFORMATION: modified by /3InvdT/

<400> SEQUENCE: 29
ttgagagtat ttgagagtat tt                                                  22

<210> SEQ ID NO 30
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: modified by /5Alex647N/
<220> FEATURE:
<221> NAME/KEY: misc_feature
<222> LOCATION: (22)..(22)
<223> OTHER INFORMATION: modified by /3InvdT/

<400> SEQUENCE: 30
tttattattg gttattattg gt                                                  22

<210> SEQ ID NO 31
<211> LENGTH: 42
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: modified by /5ThioMC6/

<400> SEQUENCE: 31
aattctatga caccgccacg ccctatatcc tcgcaataac cc                            42

<210> SEQ ID NO 32
<211> LENGTH: 60
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: modified by /5ATTO565N/

<400> SEQUENCE: 32
tttgggttat tgcgaggata tagggcgtgg cggtgtcata gaattttttt taatactctc         60

<210> SEQ ID NO 33
<211> LENGTH: 43
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (43)..(43)
<223> OTHER INFORMATION: modified by /3InvdT/
```

<400> SEQUENCE: 33
aaatactctc gggccttttg gcccgagagt atttgagagt att         43

<210> SEQ ID NO 34
<211> LENGTH: 41
<212> TYPE: DNA
<213> ORGANISM: Artificial sequence
<220> FEATURE:
<223> OTHER INFORMATION: Synthetic polynucleotide

<400> SEQUENCE: 34
gagagtattt gagagtattt gagagtattt ttccttctat t         41

<210> SEQ ID NO 35
<211> LENGTH: 43
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (43)..(43)
<223> OTHER INFORMATION: modified by /3InvdT/

<400> SEQUENCE: 35
accttctatt gggccttttg gcccaataga aggtaataga agg         43

<210> SEQ ID NO 36
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: modified by /5ATTO565N/
<220> FEATURE:
<221> NAME/KEY: misc_feature
<222> LOCATION: (22)..(22)
<223> OTHER INFORMATION: modified by /3InvdT/

<400> SEQUENCE: 36
ttaatagaag gtaatagaag gt         22

<210> SEQ ID NO 37
<211> LENGTH: 39
<212> TYPE: DNA
<213> ORGANISM: Artificial sequence
<220> FEATURE:
<223> OTHER INFORMATION: Synthetic polynucleotide

<400> SEQUENCE: 37
ctagatcgaa ctattcgaac actaaatatt catcatcat         39

<210> SEQ ID NO 38
<211> LENGTH: 43
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (43)..(43)
<223> OTHER INFORMATION: modified by /3InvdT/

<400> SEQUENCE: 38
acatcatcat gggccttttg gcccatgatg atgtatgatg atg         43

<210> SEQ ID NO 39
<211> LENGTH: 28
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: modified by /5ThioMC6-D/

<400> SEQUENCE: 39
tatttagtgt tcgaatagtt cgatctag                                        28

<210> SEQ ID NO 40
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: modified by /5Alex647N/
<220> FEATURE:
<221> NAME/KEY: misc_feature
<222> LOCATION: (22)..(22)
<223> OTHER INFORMATION: modified by /3InvdT/

<400> SEQUENCE: 40
ttatgatgat gtatgatgat gt                                              22

<210> SEQ ID NO 41
<211> LENGTH: 33
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: modified by /5ATTO488N/

<400> SEQUENCE: 41
ttgcgaggaa aactgaaaaa ggtttctctt att                                  33

<210> SEQ ID NO 42
<211> LENGTH: 22
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: modified by /5ATTO565N/
<220> FEATURE:
<221> NAME/KEY: misc_feature
<222> LOCATION: (22)..(22)
<223> OTHER INFORMATION: modified by /3InvdT/

<400> SEQUENCE: 42
ttgagagtat ttgagagtat tt                                              22